United States Patent
Nishimae et al.

(10) Patent No.: US 10,584,126 B2
(45) Date of Patent: Mar. 10, 2020

(54) 1-FUNCTIONALIZED DIBENZOFURANS AND DIBENZOTHIOPHENES FOR ORGANIC LIGHT EMITTING DIODES (OLEDS)

(71) Applicant: Idemitsu Kosan Co., Ltd., Chiyoda-ku (JP)

(72) Inventors: Yuichi Nishimae, Basel (CH); Julia Kohlstedt, Loerrach (DE); Thomas Schaefer, Liestal (CH); Hideaki Nagashima, Basel (CH)

(73) Assignee: Idemitsu Kosan Co., Ltd., Chiyoda-ku (JP)

( * ) Notice: Subject to any disclaimer, the term of this patent is extended or adjusted under 35 U.S.C. 154(b) by 176 days.

(21) Appl. No.: 15/535,898

(22) PCT Filed: Dec. 15, 2015

(86) PCT No.: PCT/IB2015/059614
§ 371 (c)(1),
(2) Date: Jun. 14, 2017

(87) PCT Pub. No.: WO2016/097983
PCT Pub. Date: Jun. 23, 2016

(65) Prior Publication Data
US 2017/0362241 A1    Dec. 21, 2017

(30) Foreign Application Priority Data

Dec. 15, 2014  (EP) .................................... 14197952

(51) Int. Cl.
| | | |
|---|---|---|
| *H01L 51/50* | (2006.01) | |
| *C07D 487/04* | (2006.01) | |
| *H01L 51/00* | (2006.01) | |
| *C09K 11/06* | (2006.01) | |

(52) U.S. Cl.
CPC ............ *C07D 487/04* (2013.01); *C09K 11/06* (2013.01); *H01L 51/0072* (2013.01); *H01L 51/0073* (2013.01); *C09K 2211/185* (2013.01); *H01L 51/0085* (2013.01); *H01L 51/5016* (2013.01); *H01L 51/5096* (2013.01)

(58) Field of Classification Search
None
See application file for complete search history.

(56) References Cited

U.S. PATENT DOCUMENTS

| | | | | |
|---|---|---|---|---|
| 2004/0164292 | A1* | 8/2004 | Tung ................. | G02F 1/133603 257/40 |
| 2012/0241681 | A1* | 9/2012 | Schaefer ............. | C07D 487/04 252/500 |
| 2013/0092922 | A1 | 4/2013 | Stoessel et al. | |
| 2013/0341602 | A1 | 12/2013 | Hikime et al. | |
| 2014/0027755 | A1 | 1/2014 | Mujica-Fernaud et al. | |
| 2014/0209885 | A1* | 7/2014 | Tada ...................... | C09K 11/06 257/40 |
| 2014/0252280 | A1 | 9/2014 | Schaefer et al. | |
| 2015/0171340 | A1† | 6/2015 | Lee | |
| 2015/0207083 | A1 | 7/2015 | Schaefer et al. | |
| 2015/0228908 | A1* | 8/2015 | Lee ..................... | H01L 51/0067 257/40 |
| 2015/0243907 | A1 | 8/2015 | Wolleb et al. | |
| 2018/0086763 | A1* | 3/2018 | Raimann ............ | H01L 51/5016 |

FOREIGN PATENT DOCUMENTS

| | | |
|---|---|---|
| DE | 10 2012 000 064 A1 | 7/2012 |
| EP | 2 878 599 A1 | 6/2015 |
| EP | 2 993 215 A1 | 3/2016 |
| GB | 1180743 | 2/1970 |
| JP | 2012-49518 A | 3/2012 |
| JP | 2013069905 A † | 4/2013 |
| KR | 10-2010-0031736 A † | 3/2010 |
| KR | 20130142967 A † | 12/2013 |
| KR | 10-2014-0025445 A † | 3/2014 |
| WO | WO 2011/160757 A1 | 12/2011 |

(Continued)

OTHER PUBLICATIONS

International Search Report dated Mar. 2, 2016 in PCT/IB2015/059614.

Marko Zupan, et al., "Fluorination with $XeF_2$.[1] 44. Effect of Geometry and Heteroatom on the Regioselectivity of Fluorine Introduction into an Aromatic Ring", The Journal of Organic Chemistry, vol. 63 No. 3, XP055189670, Feb. 1, 1998, pp. 878-880.

Bin Xiao, et al., "Synthesis of Dibenzofurans via Palladium-Catalyzed Phenol-Directed C—H Activation/C—O Cyclization" Journal of the American Chemical Society, vol. 133 No. 24, XP055189880, Jun. 22, 2011, pp. 9250-9253.

Katharine Geramita, et al., "2,7-Substituted Hexafluoroheterofluorenes as Potential Building Blocks for Electron Transporting Materials", The Journal of Organic Chemistry, vol. 74 No. 2, XP055189883, Jan. 16, 2009, pp. 820-829.

(Continued)

*Primary Examiner* — Gregory D Clark
(74) *Attorney, Agent, or Firm* — Oblon, McClelland, Maier & Neustadt, L.L.P.

(57) ABSTRACT

The present invention relates to compounds of formula(I), a process for their production and their use in electronic devices, especially electroluminescent devices. When used as charge transport material and/or host material for phosphorescent emitters in electroluminescent devices, the compounds of formula I may provide improved efficiency and reduced driving voltage of electroluminescent devices.

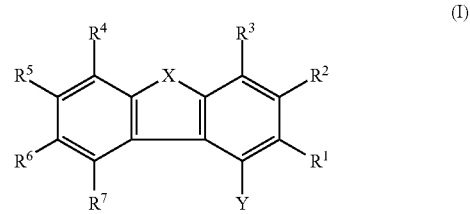

(I)

8 Claims, No Drawings

(56) References Cited

FOREIGN PATENT DOCUMENTS

| WO | WO 2012/130709 A1 | 10/2012 |
|----|-------------------|---------|
| WO | WO 2012/139692 A1 | 10/2012 |
| WO | 13077362 A1 † | 5/2013 |
| WO | WO 2013/068376 A1 | 5/2013 |
| WO | WO 2014/009317 A1 | 1/2014 |
| WO | WO 2014/044722 A1 | 3/2014 |
| WO | WO 2014/097813 A1 † | 6/2014 |

OTHER PUBLICATIONS

Julia Ponce Gonzalez, et al., "Synthesis of Fluorinated Fused Benzofurans and Benzothiophenes: Smiles-type Rearrangement and Cyclisation of Perfluoro(het)aryl Ethers and Sulfides", Organic & Biomolecular Chemistry, vol. 9 No. 7, XP055189885, Jan. 1, 2011, pp. 2294-2305.

Rui Che, et al., "Synthesis of Dibenzothiophenes by Pd-Catalyzed Dual C—H Activation from Diaryl Sulfides", Chemistry-A European Journal, vol. 20 No. 24, XP055189886, May 14, 2014, pp. 7258-7261.

Herzke Dorte, et al., "Physical-Chemical Properties of Polyflurinated Dibenzo-p-dioxins and Dibenzofurans", Organohalogen Compounds, vol. 41, Jan. 1, 1999, pp. 171-174 with cover page.

P. J. N. Brown, et al., "Aromatic Polyfluoro-Comounds-XXXVIII[1] 1,2,3,4-Tetrafluorodibenzofuran and Some Nucleophilic Replacement Reactions", Tetrahedron, vol. 23 No. 10, XP055250067, Jan. 1, 1967, pp. 4041-4045.

Karel Šindelář, et al., "Fluorinated Tricyclic Neuroleptics with Prolonged Action: 3-Fluprp-*-Trifluoromethyl Derivatives of 10-(4-Methylpiperazino)- and 10-[4-(2-Hydroxyethyl)Piperazino]-10,11-Dihydrodibenzo-[b,f]Thiepin", Collection of Czechoslovak Chemical Communications, vol. 46 No. 1, XP002347168, Jan. 1, 1981, pp. 118-140.

Misbahul Ain Khan, et al., Tetracyclic Heteroaromatic Systems. Part-II. Benzimidazo [1,2-a] Benzimidazoles, Pakistan Journal of Scientific and Industrial Research, vol. 43 No. 3, 2000, pp. 168-170.

Pedro Molina, et al., "Synthetic Applications of C,C-Bis (Iminophosphoranes): Preparation of [5+5] Rigid Bicyclic Guanidines and 1,3,6-Benzothiadiazepino [3,2-a] benzimidazole Derivatives", Tetrahedron, vol. 50 No. 33, 1994, pp. 10029-10036.

I.V. Kolesnikova, et al., "Reaction of N-Pentafluorophenylcarbonimidoyl Dichloride with Primary Amines", Zhurnal Organicheskoi Khimii, vol. 25, 1989, pp. 1523-1529 with cover page.

Reddouane Achour, et al., "Syntheses Des Benzimidazolo [1,2-a] Benzimidazoles a Partir Des Benzodiazepine-1, 5 ones-2", Bulletin des Societes Chimiques Belges, vol. 96 No. 10, 1987, pp. 787-792 (with English abstract).

André J. Hubert, et al., "Thermolyse and Photolyse von Bensotriazolyl-(1)-Derivaten", Chemische Berichte, vol. 103, Apr. 1970, pp. 228-2835.

Xiaoqiang Wang, et al., "Copper-Catalyzed Aerobic Oxidative Intramolecular C—H Amination Leading to Imidazobenzimidazole Derivatives", Organic Letters, vol. 14 No. 2, 2012, pp. 452-455.

Parthasarathi Subramanian, et al., "A Unified Strategy Towards N-Aryl Heterocycles by a One-Pot Copper-Catalyzed Oxidative C—H Amination of Azoles", European Journal of Organic Chemistry, 2014, pp. 5986-5997.

\* cited by examiner
† cited by third party

1-FUNCTIONALIZED DIBENZOFURANS AND DIBENZOTHIOPHENES FOR ORGANIC LIGHT EMITTING DIODES (OLEDS)

The present invention relates to compounds of formula I, a process for their production and their use in electronic devices, especially electroluminescent devices. When used as hole transport material in electroluminescent devices, the compounds of formula I may provide improved efficiency, stability, manufacturability, or spectral characteristics of electroluminescent devices.

DE102012000064 describes compounds of formula

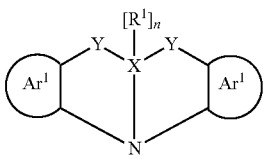

(1)

and their use in organic light emitting devices (OLEDs). Among others X can be C. If X is C, n is 1.

WO2012139692 relates to electronic devices which comprise an anode, a cathode and at least one organic layer, where the organic layer comprises one or more substituted benzene compounds of formula

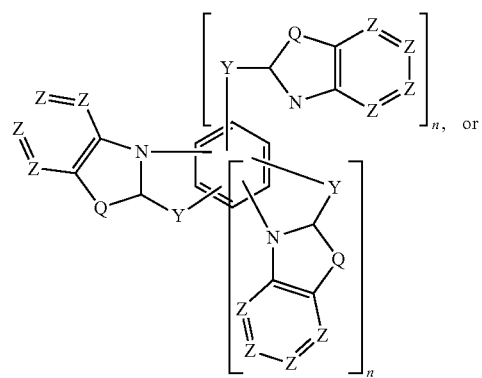

(I)

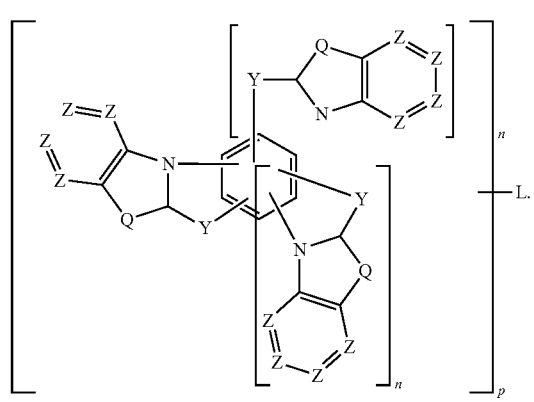

(II)

Y can be S and n can be 0 or 1, Z is $CR^1$ or N. $R^1$ can be an aromatic or hetero aromatic ring system.

Khan, Misbahul Ain; Ribeiro, Vera Lucia Teixeira, Pakistan Journal of Scientific and Industrial Research 43 (2000) 168-170 describes the synthesis of benzimidazo[1,2-a]benzimadozoles

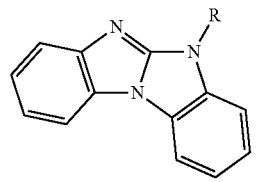

(R = H, Me, Et)

by trialkyl phosphite-induced deoxygenation and thermolysis of 1-(o-nitrophenyl)- and 1-(o-azidophenyl)benzimidazoles.

Pedro Molina et al. Tetrahedron (1994) 10029-10036 reports that aza Wittig-type reaction of bis(iminophosphoranes), derived from bis(2-aminophenyl)amine with two equivalents of isocyanate directly provided benzimidazo[1,2-a]benzimidazole derivatives.

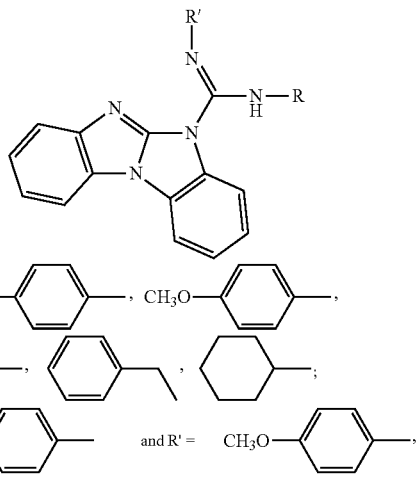

(R = R' = $H_3C$—⌬—, $CH_3O$—⌬—,

F—⌬—, ⌬—CH₂—, ⌬—cyclohexyl;

R = $H_3C$—⌬— and R' = $CH_3O$—⌬—,

R = isopropyl and R' = ethyl)

Kolesnikova, I. V.; Zhurnal Organicheskoi Khimii 25 (1989) 1689-95 describes the synthesis of 5H-benzimidazo[1,2-a]benzimidazole 1,2,3,4,7,8,9,10-octafluoro-5-(2,3,4,5,6-pentafluorophenyl).

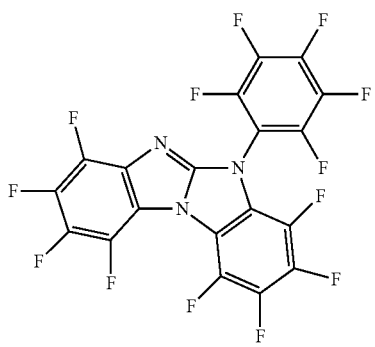 [SMILES: Fc1c(F)c(F)c(-n2c3c(F)c(F)c(F)c(F)c3n3c4c(F)c(F)c(F)c(F)c4nc23)c(F)c1F]

Achour, Reddouane; Zniber, Rachid, Bulletin des Societes Chimiques Belges 96 (1987) 787-92 describes the synthesis of benzimidazobenzimidazoles

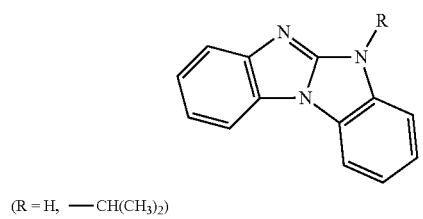

(R = H, —CH(CH$_3$)$_2$)

which were prepared from benzimidazolinone derivatives.

Hubert, Andre J.; Reimlinger, Hans, Chemische Berichte 103 (1970) 2828-35 describes the synthesis of benzimidazobenzimidazoles

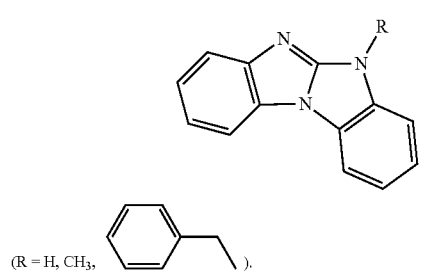

(R = H, CH$_3$, 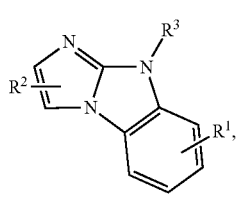 ).

X. Wang et al. *Org. Lett.* 2012, 14, 452-455 discloses a highly efficient copper-catalyzed synthesis for compounds of formula

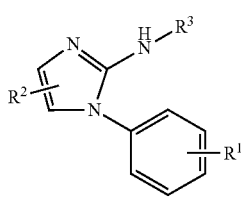

wherein compounds of formula

[structure]

are reacted in the presence of copper acetate (Cu(OAc)$_2$)/PPh$_3$/1,10-phenathroline/sodium acetate and oxygen in m-xylene (1 atm) at elevated temperature [published on web: Dec. 29, 2011]. Among others the following compounds can be prepared by the described synthesis method:

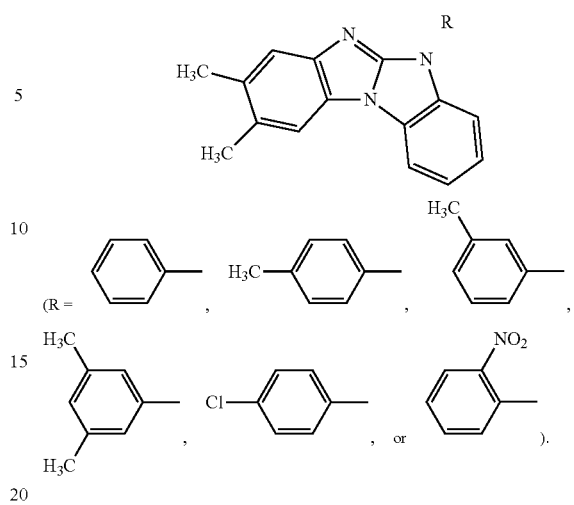

In *Eur. J. Org. Chem.* 2014, 5986-5997 a new synthesis of benzimidazolo[1,2-a]benzimidazole is described.

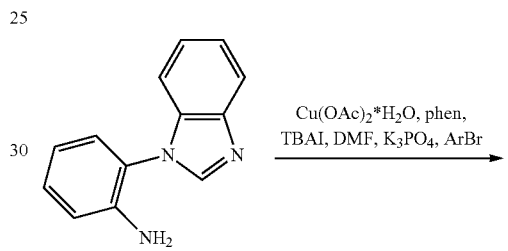

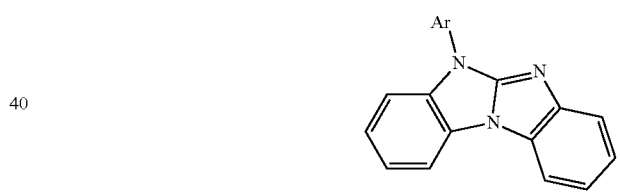

WO2011/160757 relates to an electronic device comprising an anode, cathode and at least one organic layer which contains a compound of formulae

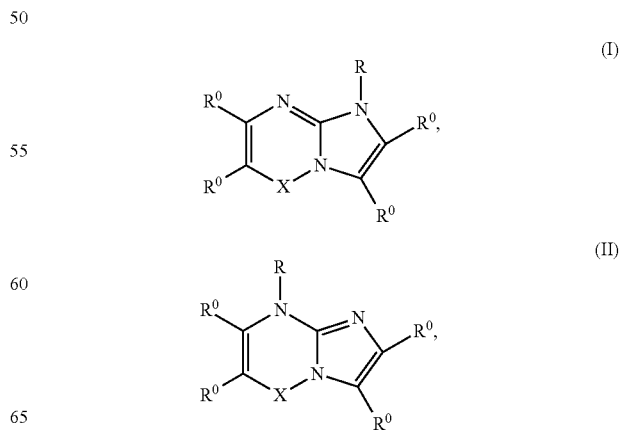

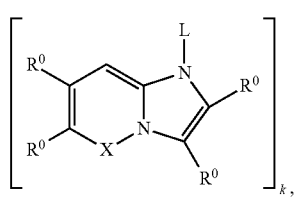
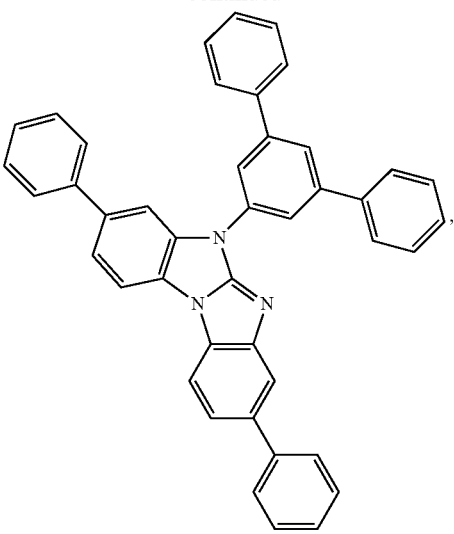
wherein X may be a single bond and L may be a divalent group. The following 4H-Imidazo[1,2-a]imidazole compounds are explicitly disclosed:
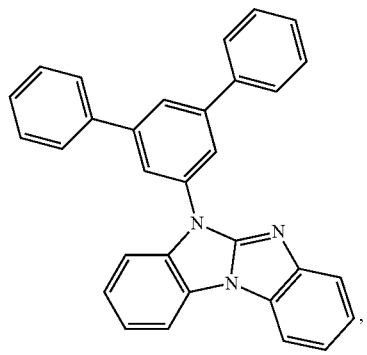
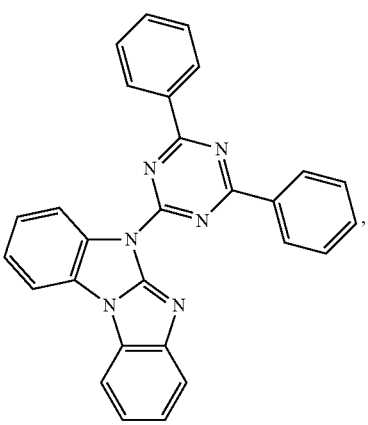
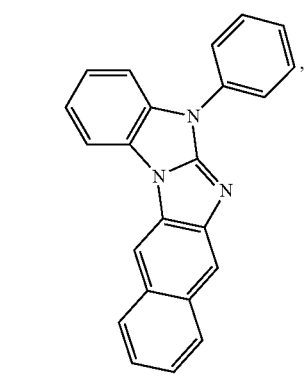
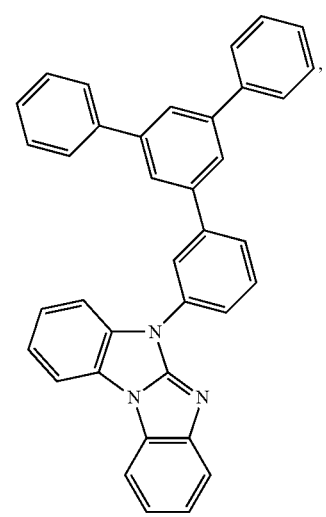
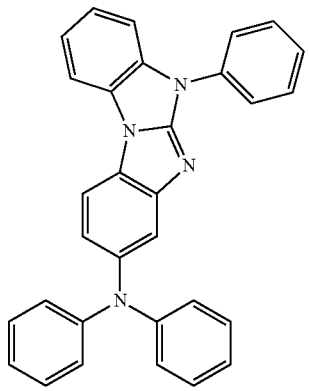

-continued

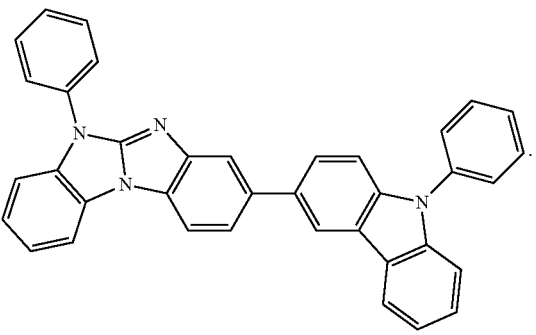

WO2012/130709 relates to 4H-Imidazo[1,2-a]imidazoles,

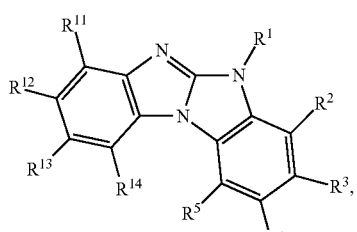

such as, for example,

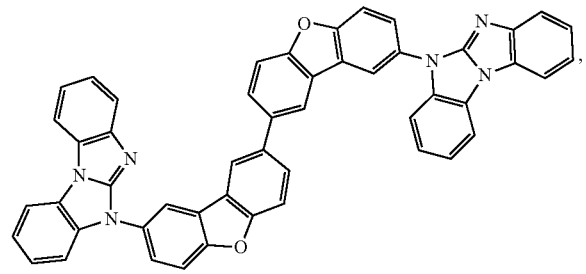

(A-1)

a process for their production and their use in electronic devices, especially electroluminescent devices.

WO2013/068376 describes 4H-imidazo[1,2-a]imidazoles of formula

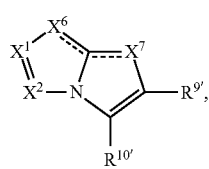

wherein $X^6$ is —N= and $X^7$ is —NR$^6$—, or $X^7$ is =N— and $X^6$ is —NR$^6$—, $R^6$ is a group of formula

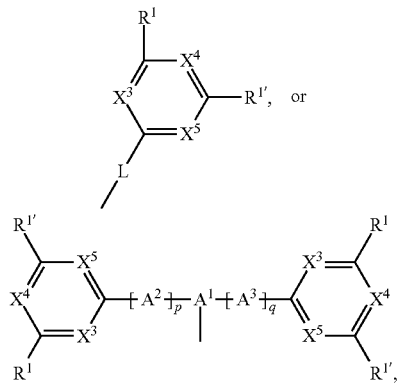

such as, for example,

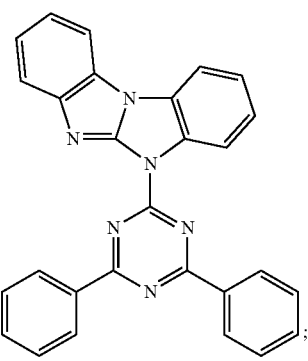 [SMILES: c1ccc(-c2nc(-c3ccccc3)nc(-n3c4ccccc4n4c5ccccc5nc34)n2)cc1]

a process for their production and their use in electronic devices, especially electroluminescent devices.

WO2014/009317 relates to compounds of formula

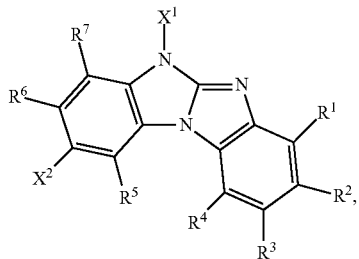

(I)

especially compounds of formula

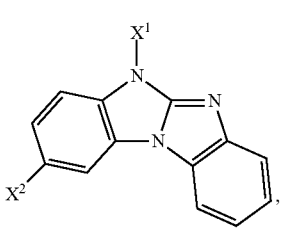

(Ia)

such as, for example,

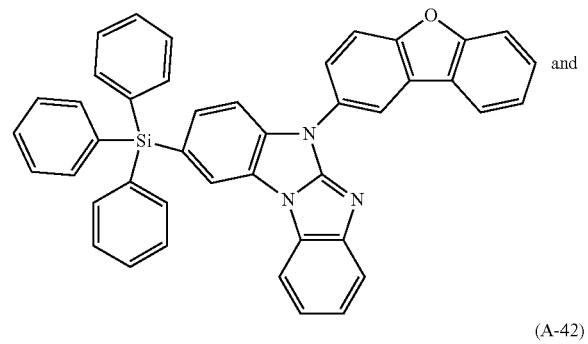
(B-1)

and

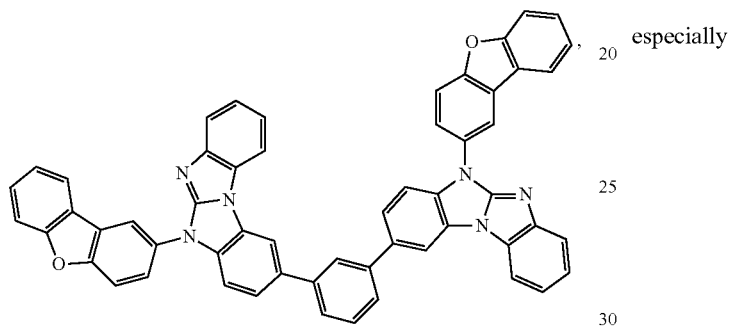
(A-42)

a process for their production and their use in electronic devices, especially electroluminescent devices. The 2,5-disubstituted benzimidazo[1,2-a]benzimidazole derivatives are suitable hole transporting materials, or host materials for phosphorescent emitters.

WO2014/044722 relates to compounds of formula

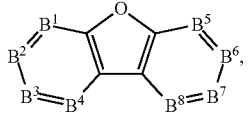
(I)

which are characterized in that they substituted by benzimidazo[1,2-a]benzimidazo-5-yl and/or benzimidazo[1,2-a]benzimidazo-2,5-ylene groups and in that at least one of the substituents $B^1$, $B^2$, $B^3$, $B^4$, $B^5$, $B^6$, $B^7$ and $B^8$ represents N, a process for their production and their use in electronic devices, especially electroluminescent devices.

European patent application no. 13191100.0 relates to compounds of formula

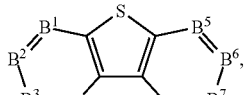
(I)

which are characterized in that they are substituted by benzimidazo[1,2-a]benzimidazo-5-yl and/or benzimidazo[1,2-a]benzimidazo-2,5-ylene groups and in that at least one of the substituents $B^1$, $B^2$, $B^3$, $B^4$, $B^5$, $B^6$, $B^7$ and $B^8$ represents N; a process for their production and their use in electronic devices, especially electroluminescent devices.

European patent application no. 14162667.1 relates to compounds of the formula

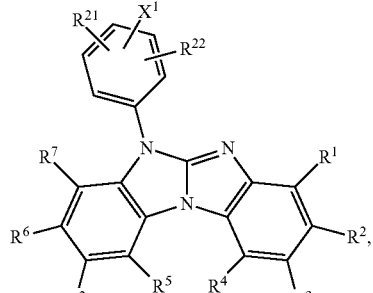
(I)

especially

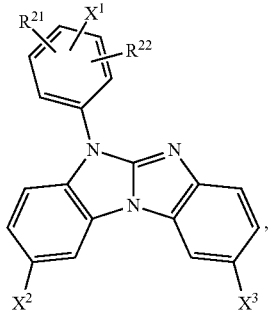
(Ia)

wherein $X^1$ is H, a group of formula

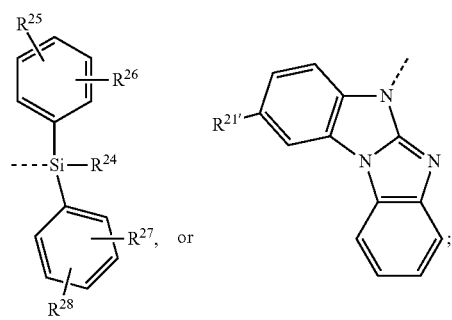

$X^2$ and $X^3$ are independently of each other H, or a group of formula

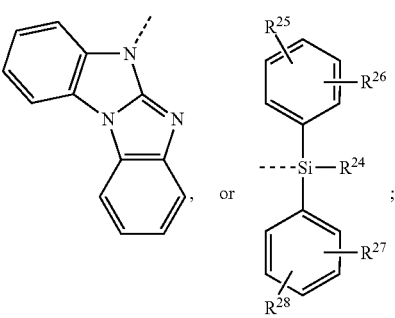

wherein at least one of X¹, X² and X³ is a group of formula

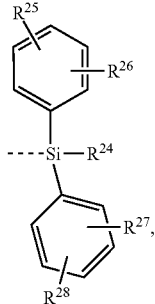

or comprises a group of formula

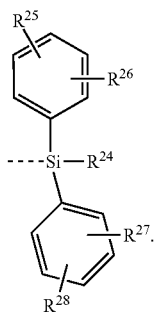

Benzimidazo[1,2-a]benzimidazo-5-yl and benzimidazo[1,2-a]benzimidazo-2-ylsubstituted benzimidazolo[2,1-b][1,3]benzothiazole derivatives are described in PCT/EP2014/066174. Azabenzimidazo[2,1-a]benzimidazoles for electronic applications are described in European patent application no. 14183598.3.

JP201249518 relates to a material for an organic electroluminescent element, which is a compound represented by general formula

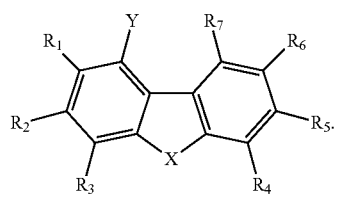

US2013341602 (JP2013243266) relates to an organic electroluminescence device which is constituted from organic layers including at least a light-emitting layer which are interposed between an anode and a cathode, wherein at least one layer of the above organic layers contains a blue phosphorescent organic metal complex having a structure represented by Formula (1) and a compound represented by the following Formula

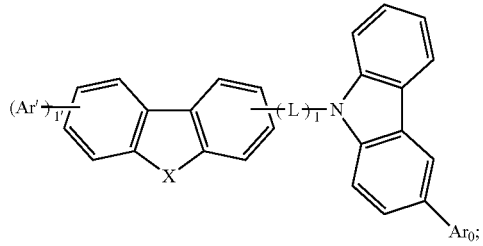

wherein X represents an oxygen atom or a sulfur atom; L represents a single bond or a linkage group derived from an aromatic hydrocarbon ring or an aromatic heterocycle; Ar₀ and Ar' each represent independently an aromatic hydrocarbon ring or an aromatic heterocycle; l represents an integer of 0 to 3, and l' represents an integer of 0 to 4. Among others the following compound is disclosed:

Accordingly, it is an object of the present invention, with respect to the aforementioned prior art, to provide further materials suitable for use in OLEDs and further applications in organic electronics. More particularly, it should be possible to provide charge transport materials, charge/exciton blocker materials and matrix materials for use in OLEDs. The materials should be suitable especially for OLEDs which comprise at least one phosphorescence emitter, especially at least one green emitter or at least one blue emitter. Furthermore, the materials should be suitable for providing OLEDs which ensure good efficiencies, good operative lifetimes and a high stability to thermal stress, and a low use and operating voltage of the OLEDs.

Certain 1-functionalized dibenzofurans and dibenzothiophenes are found to be suitable for use in organo-electroluminescent devices. In particular, said derivatives are suitable charge transport materials, or host materials for phosphorescent emitters with low driving voltage, good efficiency and good operative lifetimes.

Accordingly, said object has been solved by compounds of the formula

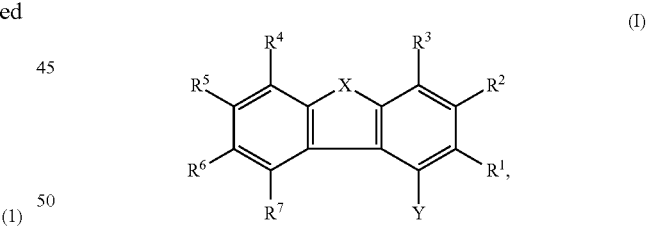

wherein
X is O or S;
Y is a group of formula $-[Ar^1]_a-[Ar^2]_b-[Ar^3]_c-A^1$;
A¹ is a group of formula

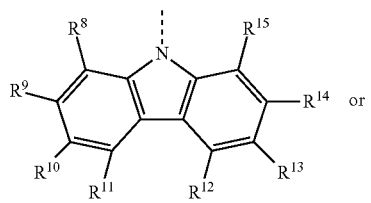

-continued

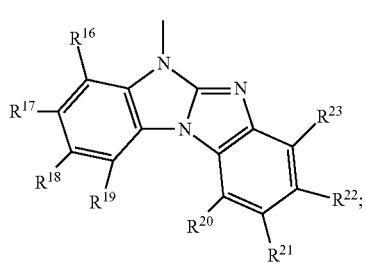

(Xb)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are independently of each other H, F, CN, $NO_2$, $Si(R^{24})(R^{25})(R^{26})$, $P(O)(R^{27})(R^{28})$, $N(R^{30})(R^{31})$, a $C_1$-$C_{25}$alkyl group, which can optionally be substituted by E, and or interrupted by D, a $C_3$-$C_{18}$cycloalkyl group, which can optionally be substituted by G, or a group of formula —$[Ar^4]_d$—$[Ar^5]_e$—$[Ar^6]_f$-$A^2$, a is 0, or 1, b is 0, or 1, c is 0, or 1, d is 0, or 1, e is 0, or 1, f is 0, or 1, $Ar^1$, $Ar^2$, $Ar^3$, $Ar^4$, $Ar^5$ and $Ar^6$ are independently of each other a $C_6$-$C_{24}$arylene group, which can optionally be substituted by G, a $C_2$-$C_{30}$heteroarylene group, which can optionally be substituted by G, $A^2$ is H, F, CN, $NO_2$, $Si(R^{24})(R^{25})(R^{26})$, $P(O)(R^{27})(R^{28})$, $N(R^{30})(R^{31})$, a $C_1$-$C_{25}$alkyl group, which can optionally be substituted by E, and or interrupted by D, a $C_3$-$C_{18}$cycloalkyl group, which can optionally be substituted by G, a $C_6$-$C_{24}$aryl group, which can optionally be substituted by G, a $C_2$-$C_{30}$heteroaryl group, which can optionally be substituted by G;

$R^{24}$, $R^{25}$, $R^{26}$, $R^{27}$, and $R^{28}$ are independently of each other a $C_1$-$C_{25}$alkyl group, a $C_6$-$C_{24}$aryl group, which can optionally be substituted by G, or a $C_2$-$C_{30}$heteroaryl group, which can optionally be substituted by G;

$R^{30}$ and $R^{31}$ are independently of each other a $C_6$-$C_{24}$aryl group, which can optionally be substituted by G, or a $C_2$-$C_{30}$heteroaryl group, which can optionally be substituted by G;

D is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—,

E is —$OR^{69}$, —$SR^{69}$, —$NR^{65}R^{66}$, —$COR^{68}$, —$COOR^{67}$, —$CONR^{65}R^{66}$, —CN, F, or $NO_2$;

G is E, or a $C_1$-$C_{18}$alkyl group, a $C_3$-$C_{18}$cycloalkyl group, a $C_6$-$C_{24}$aryl group, a $C_6$-$C_{24}$aryl group, which is substituted by F, —CN, $C_1$-$C_{18}$alkyl, or $C_1$-$C_{18}$alkyl which is interrupted by O; a $C_2$-$C_{50}$heteroaryl group, or a $C_2$-$C_{50}$heteroaryl group, which is substituted by F, —CN, $C_1$-$C_{18}$alkyl, $C_1$-$C_{18}$alkyl which is interrupted by O;

$R^{63}$ and $R^{64}$ are independently of each other H, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring;

$R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{68}$ is H; a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl;

with the proviso that in case $A^1$ is a group of formula (Xa), at least one of $R^1$, $R^2$, $R^3$, $R^4$, $R^5$, $R^6$ and $R^7$ is a group of formula —$[Ar^4]_d$—$[Ar^5]_e$—$[Ar^6]_f$-$A^2$, wherein $A^2$ is a group of formula (Xb).

The substitution of 4-position of carbazole results in materials that are highly suitable for devices that emit green, or blue light. Moreover, the introduction of at least one benzimidazo[1,2-a]benzimidazo-2-yl structure to materials leads to the improvement of thermally stabilities and carrier transport properties of materials. Those properties give rise to devices which result in lower voltages, higher external quantum efficiencies (EQE), and device lifetime.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices, such as, for example, organic light-emitting diodes (OLEDs).

Accordingly, a further subject of the present invention is directed to an electronic device, comprising a compound according to the present invention. The electronic device is preferably an electroluminescent device.

The compounds of formula I can in principal be used in any layer of an EL device, but are preferably used as host, charge transport and/or charge/exciton blocking material. Particularly, the compounds of formula I are used as host material for green, especially blue light emitting phosphorescent emitters.

Hence, a further subject of the present invention is directed to a charge transport layer, comprising a compound of formula I according to the present invention.

A further subject of the present invention is directed to an emitting layer, comprising a compound of formula I according to the present invention. In said embodiment a compound of formula I is preferably used as host material in combination with a phosphorescent emitter.

A further subject of the present invention is directed to a charge/exciton blocking layer, comprising a compound of formula I according to the present invention.

D is preferably —CO—, —COO—, —S—, —SO—, —$SO_2$—, —O—, —$NR^{65}$—, wherein $R^{65}$ is $C_1$-$C_{18}$alkyl, such as methyl, ethyl, n-propyl, iso-propyl, n-butyl, isobutyl, or sec-butyl, or $C_6$-$C_{14}$aryl, such as phenyl, tolyl, naphthyl, or biphenylyl, or $C_2$-$C_{30}$heteroaryl, such as, for example, benzimidazo[1,2-a]benzimidazo-2-yl

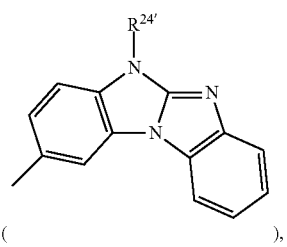

(   ), carbazolyl, dibenzofuranyl, which can be unsubstituted or substituted especially by $C_6$-$C_{10}$aryl, or $C_6$-$C_{10}$aryl, which is substituted by $C_1$-$C_4$alkyl; or $C_2$-$C_{13}$heteroaryl.

E is preferably —$OR^{69}$; —$SR^{69}$; —$NR^{65}R^{66}$; —$COR^{67}$; —$COOR^{67}$; —$CONR^{65}R^{66}$; or —CN; wherein $R^{65}$, $R^{66}$, $R^{67}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl.

G is preferably —$OR^{31}$; —$SR^{31}$; —$NR^{32}R^{33}$; a $C_1$-$C_{18}$alkyl group, a $C_6$-$C_{14}$aryl group, a $C_6$-$C_{14}$aryl group, which is substituted by F, or $C_1$-$C_{18}$alkyl; a $C_2$-$C_{13}$heteroaryl group, or a $C_2$-$C_{13}$heteroaryl group, which is substituted by F, or $C_1$-$C_{18}$alkyl; wherein $R^{31}$, $R^{32}$, $R^{33}$ and $R^{34}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl.

A $C_2$-$C_{13}$heteroaryl group is for example, benzimidazo[1,2-a]benzimidazo-5-yl

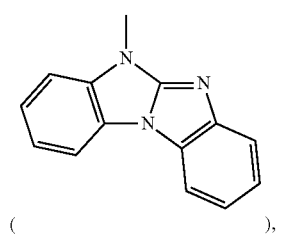 [SMILES: Cn1c2ccccc2n2c3ccccc3nc12]

(   ), benzimidazo[1,2-a]benzimidazo-2-yl

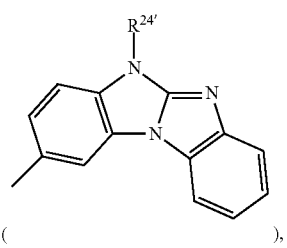

(   ), benzimidazolo[2,1-b][1,3]benzothiazolyl, carbazolyl, dibenzofuranyl, or dibenzotihophenyl, which can be unsubstituted or substituted, especially by $C_6$-$C_{10}$aryl, or $C_6$-$C_{10}$aryl, which is substituted by $C_1$-$C_4$alkyl; or $C_2$-$C_{13}$heteroaryl.

Compounds of formula (I) are preferred, wherein $R^1$, $R^2$, $R^3$, $R^4$, $R^5$, $R^6$ and $R^7$ are independently of each other H, or a group of formula $[Ar^4]_d$—$[Ar^5]_e$—$[Ar^6]_f$-$A^2$, wherein d, e, f, $Ar^4$, $Ar^5$, $Ar^6$ and $A^2$ are defined above, or below.

Compound of formula

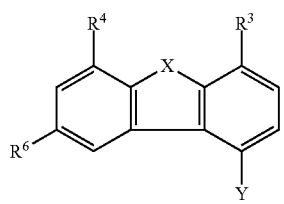

(Ia)

are more preferred, wherein $R^3$, $R^4$ and $R^6$, Y and X are defined above, or below.

Compounds of formula

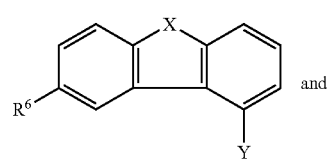

(Ia-1)

and

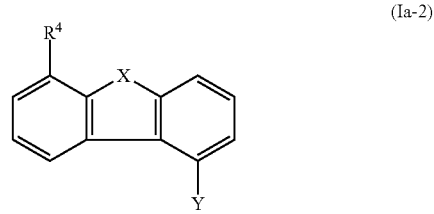

(Ia-2)

are even more preferred, wherein $R^4$, $R^6$, Y and X are defined above, or below.

Y is a group of formula —$[Ar^1]_a$—$[Ar^2]_b$—$[Ar^3]_c$-$A^1$.

a is 0, or 1, b is 0, or 1 and c is 0, or 1, especially a is 0, or 1, b is 0, or 1 and c is 0, very especially a is 0, or 1, b is 0 and c is 0. In a particularly preferred embodiment a, b and c are 0.

$Ar^1$, $Ar^2$ and $Ar^3$ are independently of each other a $C_6$-$C_{24}$arylene group, which can optionally be substituted by G, a $C_2$-$C_{30}$heteroarylene group, which can optionally be substituted by G, The $C_6$-$C_{24}$arylene groups, $Ar^1$, $Ar^2$ and $Ar^3$, which optionally can be substituted by G, are typically phenylene, 4-methylphenylene, 4-methoxyphenylene, naphthylene, especially 1-naphthylene, or 2-naphthylene, biphenylylene, terphenylylene, pyrenylene, 2- or 9-fluorenylene, phenanthrylene, or anthrylene, which may be unsubstituted or substituted.

The $C_2$-$C_{30}$heteroarylene groups, $Ar^1$, $Ar^2$ and $Ar^3$, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated-electrons such as, for example, benzofuro[2,3-b]pyridylene

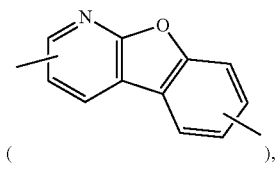

(   ), benzothiopheno[2,3-b]pyridylene

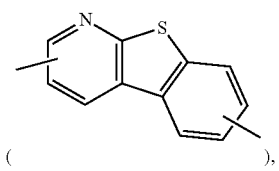

pyrido[2,3-b]indolylene

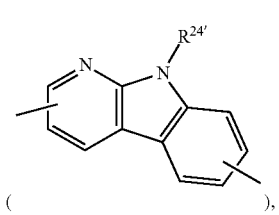

benzofuro[2,3-c]pyridylene

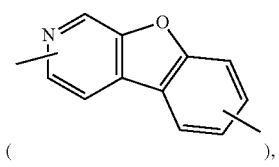

benzothiopheno[2,3-c]pyridylene

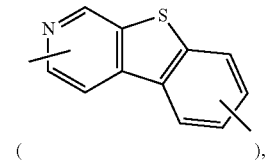

pyrido[2,3-c]indolylene

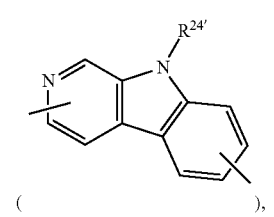

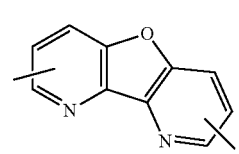

furo[3,2-b:4,5-b']dipyridylene, benzofuro[3,2-b]pyridylene

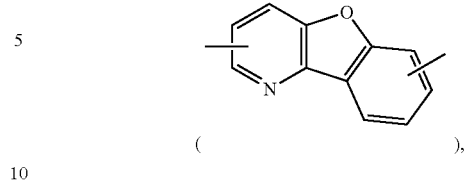

benzothiopheno[3,2-b]pyridylene

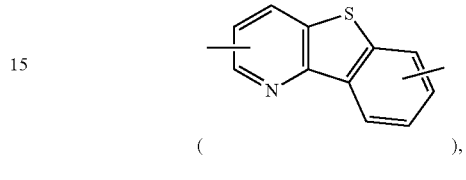

thieno[3,2-b:4,5-b']dipyridylene

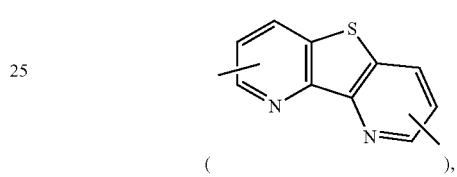

pyrrolo[3,2-b:4,5-b']dipyridylene

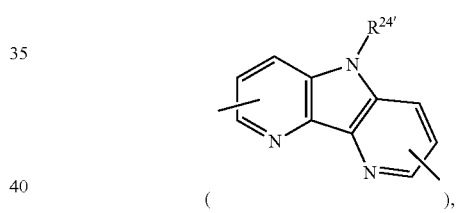

thienylene, benzothiophenylene, thianthrenylene, furylene, furfurylene, 2H-pyranylene, benzofuranylene, isobenzofuranylene, dibenzofuranylene

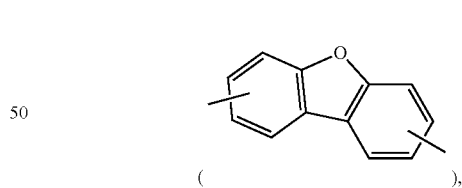

dibenzothiophenylene

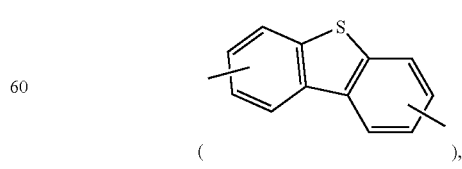

phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene

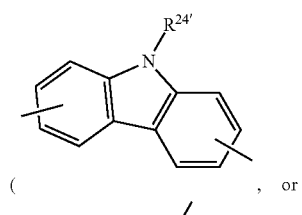

( , or

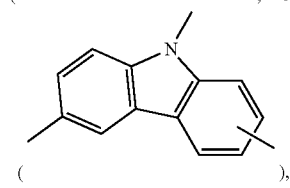

( ), benzimidazo[1,2-a]benzimidazo-2,5-ylene

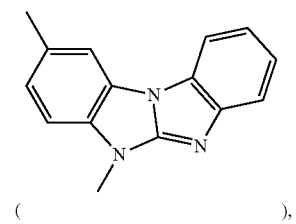 [SMILES: Cc1ccc2c(c1)n1c3ccccc3nc1n2C]

( ), benzimidazo-1,2-ylene

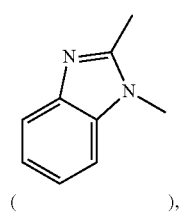

( ), or phenoxazinylene, which can be unsubstituted or substituted. $R^{24'}$ is a $C_6$-$C_{24}$aryl group, or a $C_2$-$C_{30}$heteroaryl group, which can optionally be substituted by G, wherein G is as defined in above.

Preferred $C_6$-$C_{24}$arylene groups are 1,3-phenylene, 1,4-phenylene, 3,3'-biphenylylene, 3,3'-m-terphenylene, 2- or 9-fluorenylene, phenanthrylene, which may be unsubstituted or substituted, especially by $C_6$-$C_{10}$aryl, $C_6$-$C_{10}$aryl which is substituted by $C_1$-$C_4$alkyl; or $C_2$-$C_{14}$heteroaryl.

Preferred $C_2$-$C_{30}$heteroarylene groups are pyridylene, triazinylene, pyrimidinylene, benzofuro[2,3-b]pyridylene, benzothiopheno[2,3-b]pyridylene, pyrido[2,3-b]indolylene, benzofuro[2,3-c]pyridylene, benzothiopheno[2,3-c]pyridylene, pyrido[2,3-c]indolylene, furo[3,2-b:4,5-b']dipyridylene, thieno[3,2-b:4,5-b']dipyridylene, pyrrolo[3,2-b:4,5-b']dipyridylene, dibenzofuranylene, dibenzothiophenylene, carbazolylene and benzimidazo[1,2-a]benzimidazo-2,5-ylene, benzofuro[3,2-b]pyridylene, indolylene, benzothiopheno[3,2-b]pyridylene, or benzimidazo-1,2-ylene, which can be unsubstituted or substituted, especially by $C_6$-$C_{14}$aryl, $C_6$-$C_{14}$aryl which is substituted by $C_1$-$C_4$alkyl; or $C_2$-$C_{13}$heteroaryl.

The $C_6$-$C_{24}$arylene and $C_2$-$C_{30}$heteroarylene groups may be substituted by G.

G is preferably $C_1$-$C_{18}$alkyl, such as methyl, ethyl, n-propyl, iso-propyl, n-butyl, isobutyl, sec-butyl, hexyl, octyl, or 2-ethyl-hexyl, —$CF_3$, a $C_6$-$C_{14}$aryl group, a $C_6$-$C_{14}$aryl group, which is substituted by F, or $C_1$-$C_{18}$alkyl; a $C_2$-$C_{13}$heteroaryl group, or a $C_2$-$C_{13}$heteroaryl group, which is substituted by F, or $C_1$-$C_{18}$alkyl.

Benzimidazo[1,2-a]benzimidazo-5-yl, benzimidazo[1,2-a]benzimidazo-2-yl, carbazolyl and dibenzofuranyl are examples of a $C_2$-$C_{13}$heteroaryl group. Phenyl, 1-naphthyl and 2-naphthyl are examples of a $C_6$-$C_{14}$aryl group.

Most preferred, $Ar^1$, $Ar^2$ and $Ar^3$ are a group of formula

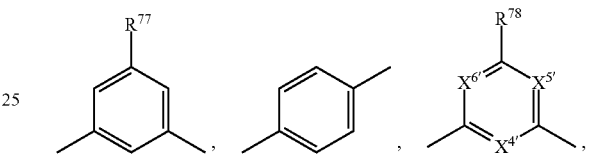

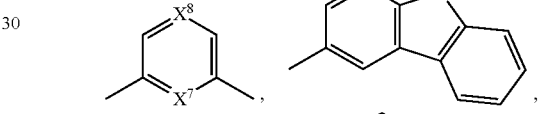

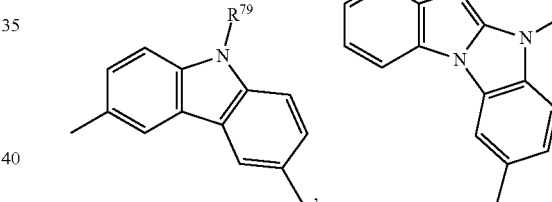

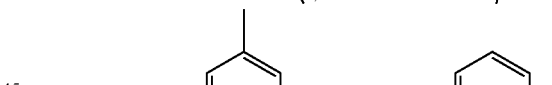

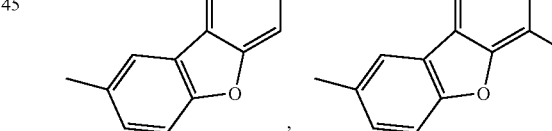

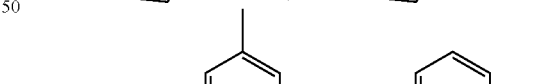

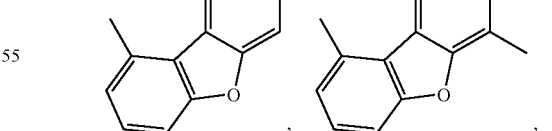

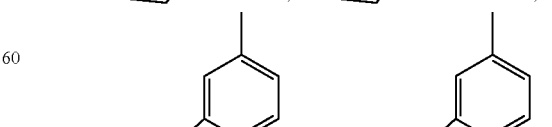

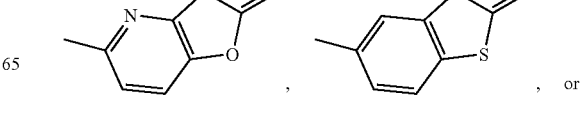

, or

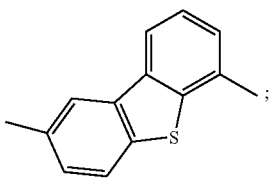

wherein

X⁴', X⁶', X⁶', X⁷ and X⁸ are independently of each other N, or CH, with the proviso that at least one of X⁴', X⁵' and X⁶' represents N;

R⁷⁷ and R⁷⁸ are independently of each other H, or a phenyl group, and

R⁷⁹ is a phenyl group, or a group of formula

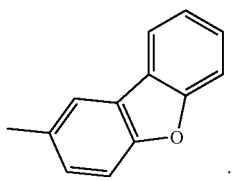

A¹ is a group of formula (Xa), or (Xb).

A¹ is preferably a group of formula

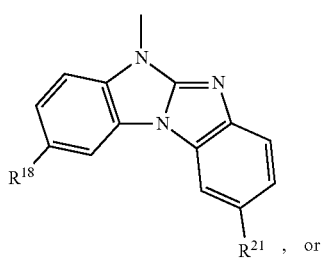 (Xa-1)

, or

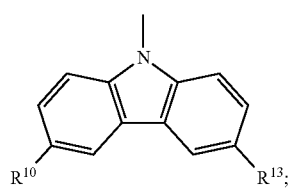 (Xb-1)

wherein

R¹⁰, R¹³, R¹⁸, and R²¹ are independently of each other H, a group of formula

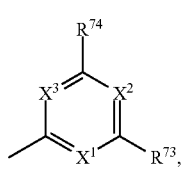, or

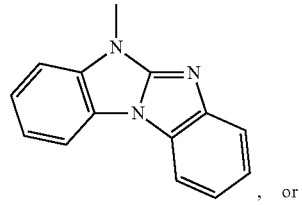

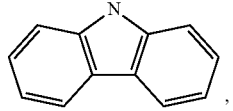, wherein

X¹, X² and X³ are independently of each other N, or CH, with the proviso that at least one of X¹, X² and X³ represent N, and R⁷³ and R⁷⁴ are independently of each other H, or a phenyl group.

Among the groups of formula A¹ those are more preferred, wherein R¹⁰, R¹³, R¹⁸ and R²¹ are independently of each other H,

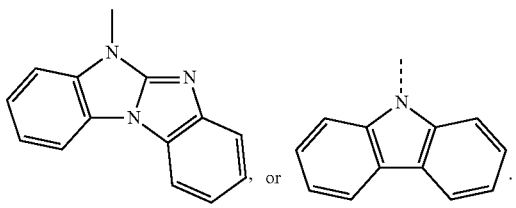

In the group of formula —[Ar⁴]_d—[Ar⁵]_e—[Ar⁶]_f-A² the following preferences apply:

d is 0, or 1, e is 0, or 1 and f is 0, or 1, especially d is 0, or 1, e is 0, or 1 and f is 0.

Ar⁴, Ar⁵ and Ar⁶ are independently of each other a C₆-C₂₄arylene group, which can optionally be substituted by G, a C₂-C₃₀heteroarylene group, which can optionally be substituted by G, The C₆-C₂₄arylene groups, Ar⁴, Ar⁵ and Ar⁶, which optionally can be substituted by G, are typically phenylene, 4-methylphenylene, 4-methoxyphenylene, naphthylene, especially 1-naphthylene, or 2-naphthylene, biphenylylene, terphenylylene, pyrenylene, 2- or 9-fluorenylene, phenanthrylene, or anthrylene, which may be unsubstituted or substituted.

The C₂-C₃₀heteroarylene groups, Ar⁴, Ar⁵ and Ar⁶, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated-electrons such as, for example, benzofuro[2,3-b]pyridylene ( 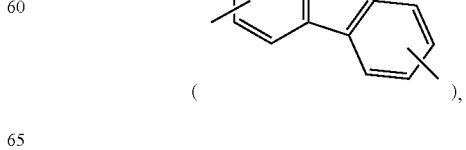 ), benzothiopheno[2,3-b]pyridylene

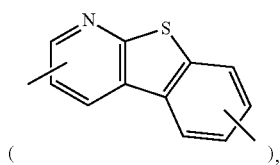
( ), pyrido[2,3-b]indolylene

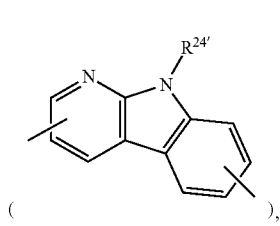
( ), benzofuro[2,3-c]pyridylene

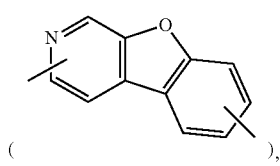
( ), benzothiopheno[2,3-c]pyridylene

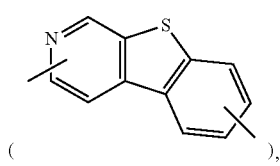
( ), pyrido[2,3-c]indolylene

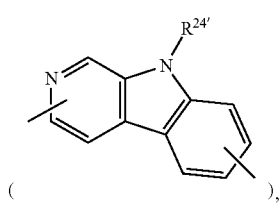
( ),

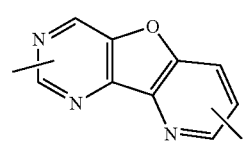

furo[3,2-b:4,5-b']dipyridylene, benzofuro[3,2-b]pyridylene

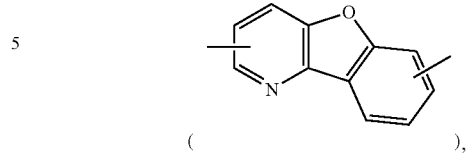
( ), benzothiopheno[3,2-b]pyridylene

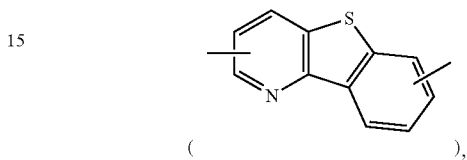
( ), thieno[3,2-b:4,5-b']dipyridylene

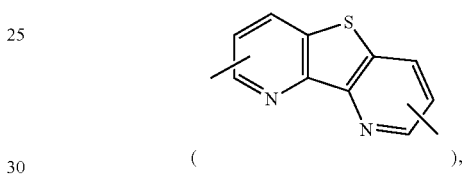
( ), pyrrolo[3,2-b:4,5-b']dipyridylene

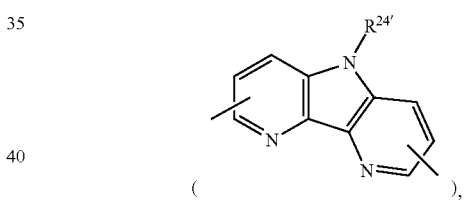
( ), thienylene, benzothiophenylene, thianthrenylene, furylene, furfurylene, 2H-pyranylene, benzofuranylene, isobenzofuranylene, dibenzofuranylene

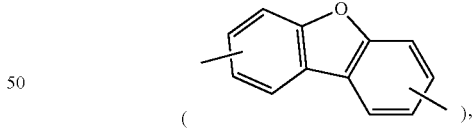
( ), dibenzothiophenylene

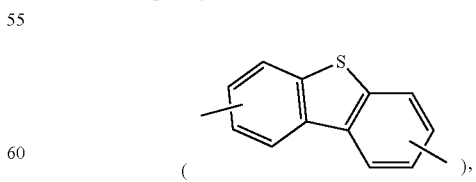
( ), phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene

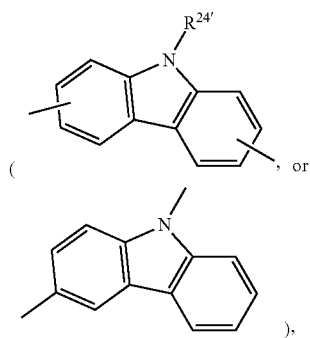

benzimidazo[1,2-a]benzimidazo-2,5-ylene

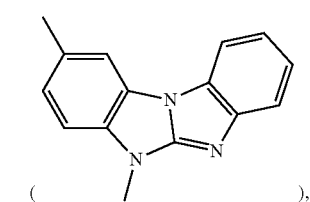 [SMILES: Cc1ccc2c(c1)n1c3ccccc3nc1n2C]

benzimidazo-1,2-ylene

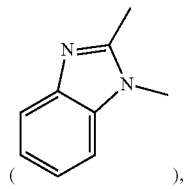

or phenoxazinylene, which can be unsubstituted or substituted. $R^{24'}$ is a $C_6$-$C_{24}$aryl group, or a $C_2$-$C_{30}$heteroaryl group, which can optionally be substituted by G, wherein G is as defined in above.

Preferred $C_6$-$C_{24}$arylene groups are 1,3-phenylene, 1,4-phenylene, 3,3'-biphenylylene, 3,3'-m-terphenylene, 2- or 9-fluorenylene, phenanthrylene, which may be unsubstituted or substituted, especially by $C_6$-$C_{10}$aryl, $C_6$-$C_{10}$aryl which is substituted by $C_1$-$C_4$alkyl; or $C_2$-$C_{14}$heteroaryl.

Preferred $C_2$-$C_{30}$heteroarylene groups are pyridylene, triazinylene, pyrimidinylene, benzofuro[2,3-b]pyridylene, benzothiopheno[2,3-b]pyridylene, pyrido[2,3-b]indolylene, benzofuro[2,3-c]pyridylene, benzothiopheno[2,3-c]pyridylene, pyrido[2,3-c]indolylene, furo[3,2-b:4,5-b']dipyridylene, thieno[3,2-b:4,5-b']dipyridylene, pyrrolo[3,2-b:4,5-b']dipyridylene, dibenzofuranylene, dibenzothiophenylene, carbazolylene and benzimidazo[1,2-a]benzimidazo-2,5-ylene, benzofuro[3,2-b]pyridylene, indolylene, benzothiopheno[3,2-b]pyridylene, or benzimidazo-1,2-ylene, which can be unsubstituted or substituted, especially by $C_6$-$C_{14}$aryl, $C_6$-$C_{14}$aryl which is substituted by $C_1$-$C_4$alkyl; or $C_2$-$C_{13}$heteroaryl.

The $C_6$-$C_{24}$arylene and $C_2$-$C_{30}$heteroarylene groups may be substituted by G.

G is preferably $C_1$-$C_{18}$alkyl, such as methyl, ethyl, n-propyl, iso-propyl, n-butyl, isobutyl, sec-butyl, hexyl, octyl, or 2-ethyl-hexyl, —$CF_3$, a $C_6$-$C_{14}$aryl group, a $C_6$-$C_{14}$aryl group, which is substituted by F, or $C_1$-$C_{18}$alkyl; a $C_2$-$C_{13}$heteroaryl group, or a $C_2$-$C_{13}$heteroaryl group, which is substituted by F, or $C_1$-$C_{18}$alkyl.

Benzimidazo[1,2-a]benzimidazo-5-yl, benzimidazo[1,2-a]benzimidazo-2-yl, carbazolyl and dibenzofuranyl are examples of a $C_2$-$C_{13}$heteroaryl group. Phenyl, 1-naphthyl and 2-naphthyl are examples of a $C_6$-$C_{14}$aryl group.

Preferably, $Ar^4$, $Ar^5$ and $Ar^6$ are independently of each other

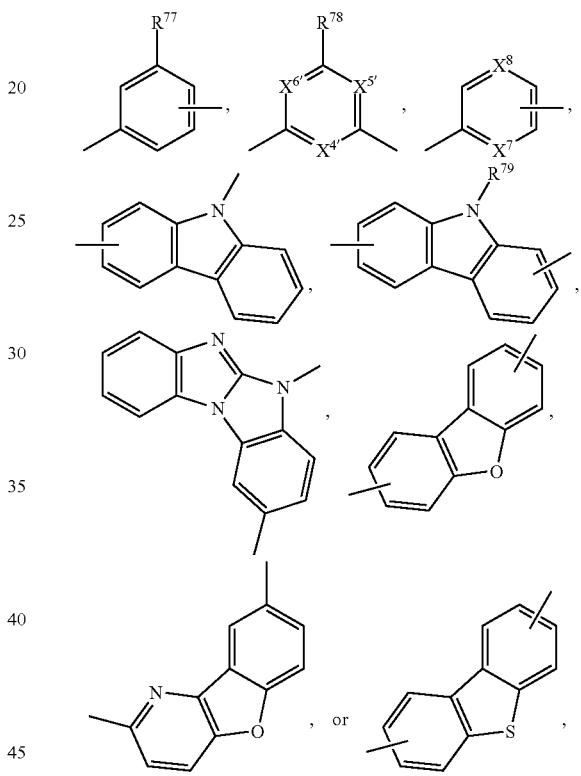

wherein $X^{4'}$, $X^{5'}$, $X^{6'}$, $X^7$ and $X^8$ are independently of each other N, or CH, with the proviso that at least one of $X^{4'}$, $X^{5'}$ and $X^{6'}$ represents N;

$R^{77}$ and $R^{78}$ are independently of each other H, or a phenyl group, and $R^{76}$ is a phenyl group, or a group of formula

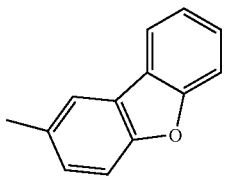

$Ar^4$, $Ar^5$ and $Ar^6$ are more preferably selected from the group of formula

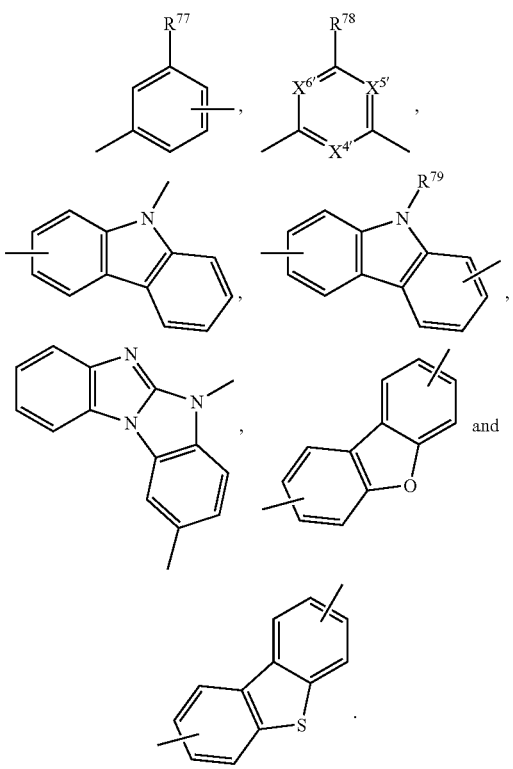

Most preferred $Ar^4$, $Ar^5$ and $Ar^6$ are a group of formula

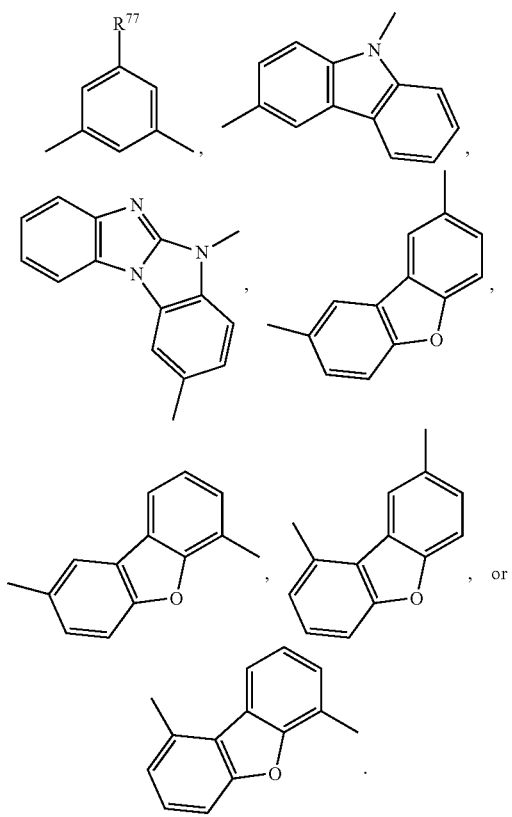

$A^2$ is H, F, $NO_2$, $Si(R^{24})(R^{25})(R^{26})$, $P(O)(R^{27})(R^{28})$, $N(R^{30})(R^{31})$, a $C_1$-$C_{25}$alkyl group, which can optionally be substituted by E, and or interrupted by D, a $C_3$-$C_{18}$cycloalkyl group, which can optionally be substituted by G, a $C_6$-$C_{24}$aryl group, which can optionally be substituted by G, a $C_2$-$C_{30}$heteroaryl group, which can optionally be substituted by G;

$R^{24}$, $R^{25}$, $R^{26}$, $R^{27}$ and $R^{28}$ are independently of each other a $C_1$-$C_{25}$alkyl group, a $C_6$-$C_{24}$aryl group, which can optionally be substituted by G, or a $C_2$-$C_{30}$heteroaryl group, which can optionally be substituted by G;

$R^{30}$ and $R^{31}$ are independently of each other a $C_6$-$C_{24}$aryl group, which can optionally be substituted by G, or a $C_2$-$C_{30}$heteroaryl group, which can optionally be substituted by G;

The $C_6$-$C_{24}$aryl group $A^2$, which optionally can be substituted by G, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, or triphenylenyl (especially triphenylen-2-yl), which may be unsubstituted or substituted.

The $C_2$-$C_{30}$heteroaryl group $A^2$, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated π-electrons such as 9H-pyrido[2,3-b]indolyl, benzofuro[2,3-b]pyridyl, benzothiopheno[2,3-b]pyridyl, 9H-pyrido[2,3-c]indolyl, benzofuro[2,3-c]pyridyl, benzothiopheno[2,3-c]pyridyl, furo[3,2-b:4,5-b']dipyridyl, pyrrolo[3,2-b:4,5-b']dipyridyl, thieno[3,2-b:4,5-b']dipyridyl, thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, benzimidazo[1,2-a]benzimidazo-5-yl, benzimidazo[1,2-a]benzimidazo-2-yl, benzimidazolo[2,1-b][1,3]benzothiazolyl, carbazolyl, 9-phenylcarbazolyl, azabenzimidazo[1,2-a]benzimidazolyl, or phenoxazinyl, which can be unsubstituted or substituted.

The $C_6$-$C_{24}$aryl and $C_2$-$C_{30}$heteroaryl groups may be substituted by G.

G is preferably $C_1$-$C_{18}$alkyl, such as methyl, ethyl, n-propyl, iso-propyl, n-butyl, isobutyl, sec-butyl, hexyl, octyl, or 2-ethyl-hexyl; —$CF_3$, a $C_6$-$C_{14}$aryl group, a $C_6$-$C_{14}$aryl group, which is substituted by F, or $C_1$-$C_{18}$alkyl; a $C_2$-$C_{13}$heteroaryl group, or a $C_2$-$C_{13}$heteroaryl group, which is substituted by F, or $C_1$-$C_{18}$alkyl.

Preferred $C_2$-$C_{30}$heteroaryl groups are pyridyl, triazinyl, pyrimidinyl, especially 9H-pyrido[2,3-b]indolyl, benzofuro[2,3-b]pyridyl, benzothiopheno[2,3-b]pyridyl, 9H-pyrido[2,3-c]indolyl, benzofuro[2,3-c]pyridyl, benzothiopheno[2,3-c]pyridyl, furo[3,2-b:4,5-b']dipyridyl, pyrrolo[3,2-b:4,5-b']dipyridyl, thieno[3,2-b:4,5-b']dipyridyl, benzimidazo[1,2-a]benzimidazo-5-yl

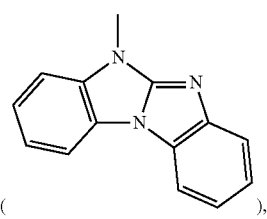 [SMILES: Cn1c2ccccc2n2c3ccccc3nc12]

benzimidazo[1,2-a]benzimidazo-2-yl

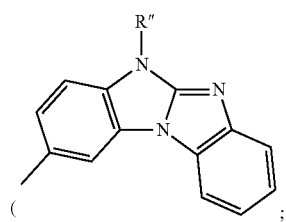

R'' is C$_6$-C$_{10}$aryl, or C$_6$-C$_{10}$aryl, which is substituted by C$_1$-C$_4$alkyl; or C$_2$-C$_{14}$heteroaryl), benzimidazolo[2,1-b][1,3]benzothiazolyl

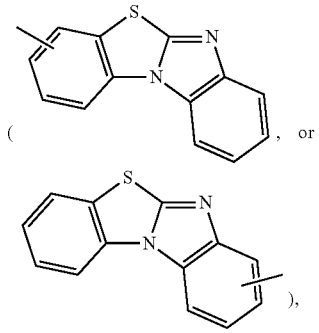

carbazolyl, dibenzofuranyl, or dibenzothiophenyl, which can be unsubstituted or substituted especially by C$_6$-C$_{10}$aryl, or C$_6$-C$_{10}$aryl, which is substituted by C$_1$-C$_4$alkyl; or C$_2$-C$_{14}$heteroaryl.

Preferably, A$^2$ is H, a group of formula (Xa), (Xb),

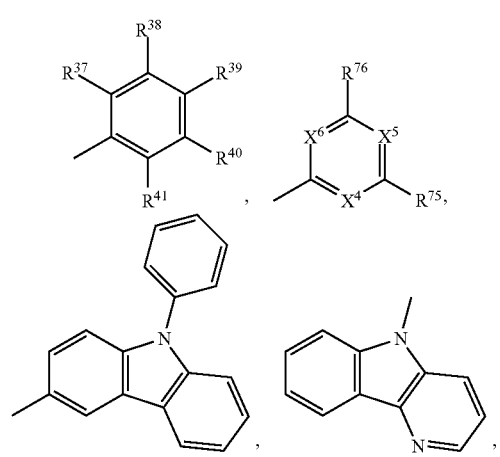

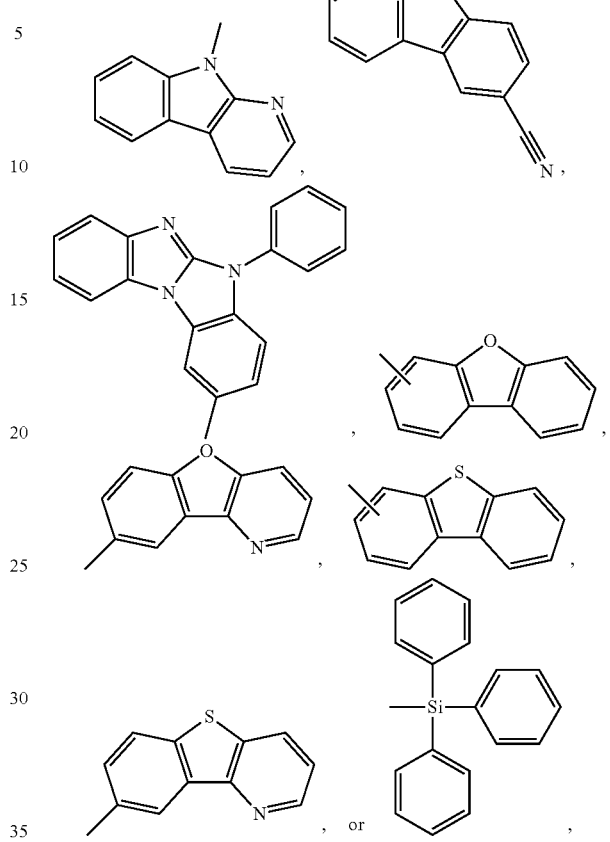

wherein
X$^4$, X$^5$ and X$^6$ are independently of each other N, or CH, with the proviso that at least one of
X$^4$, X$^5$ and X$^6$ represent N;
R$^{37}$, R$^{38}$, R$^{39}$, R$^{40}$ and R$^{41}$ are independently of each other H, or a phenyl group, and
R$^{75}$ and R$^{76}$ are independently of each other H, or a phenyl group.

Most preferred, A$^2$ is H, a group of formula (Xb-1)

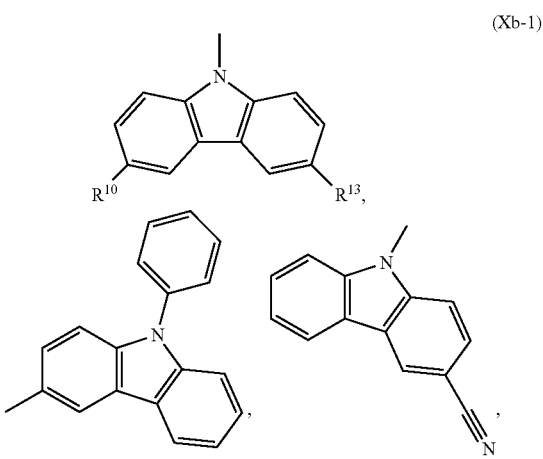

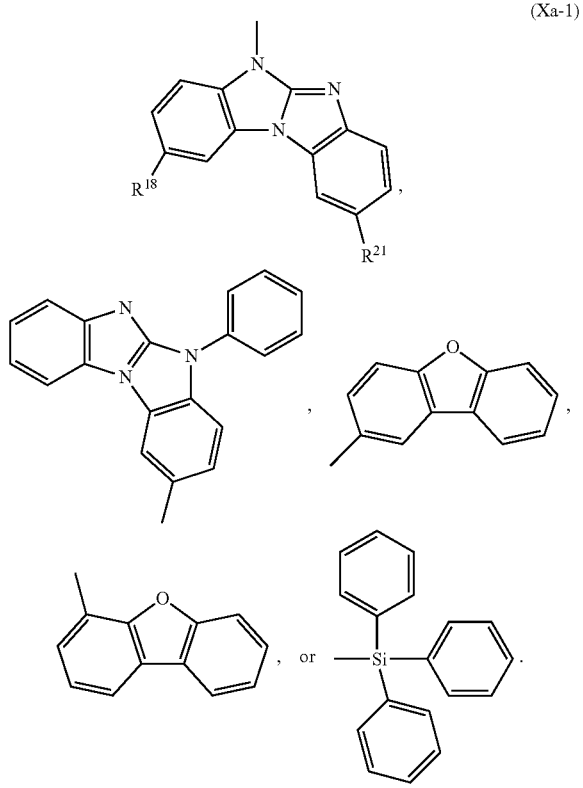

(Xa-1)

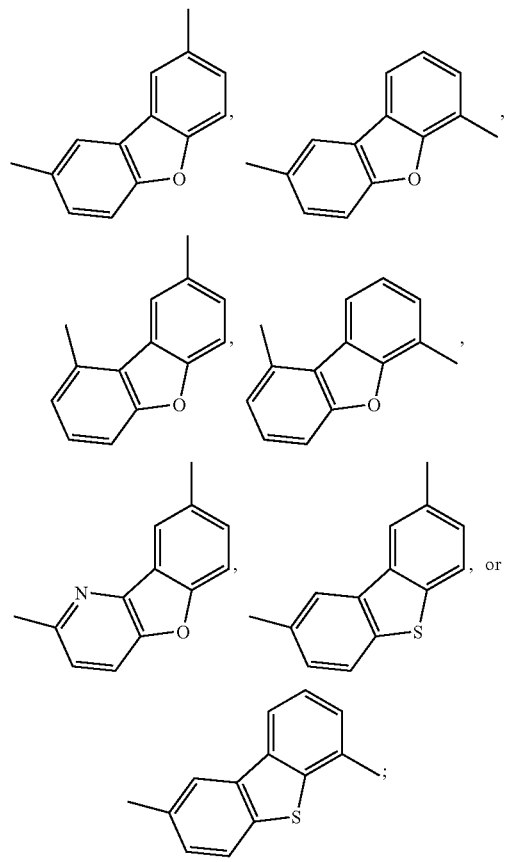

wherein

X⁴', X⁵', X⁶', X⁷ and X⁸ are independently of each other N, or CH, with the proviso that at least one of X⁴', X⁵' and X⁶' represents N;

R⁷⁷ and R⁷⁸ are independently of each other H, or a phenyl group, and

R⁷⁶ is a phenyl group, or a group of formula

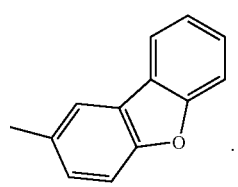

A² is H, a group of formula

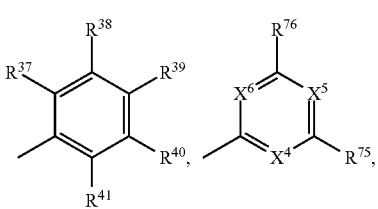

Groups of formula —[Ar⁴]$_d$—[Ar⁵]$_e$—[Ar⁶]$_f$-A² are preferred, wherein d is 0, or 1, e is 0, or 1, f is 0, or 1, Ar⁴, Ar⁵ and Ar⁶ are independently of each other

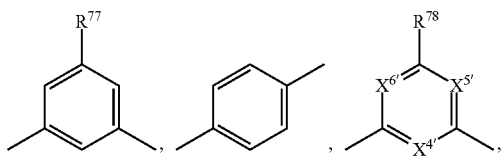

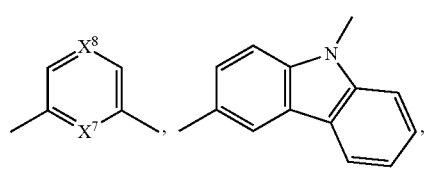

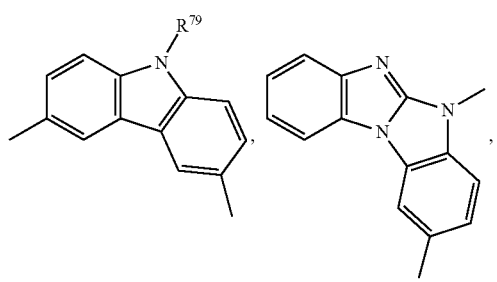

-continued

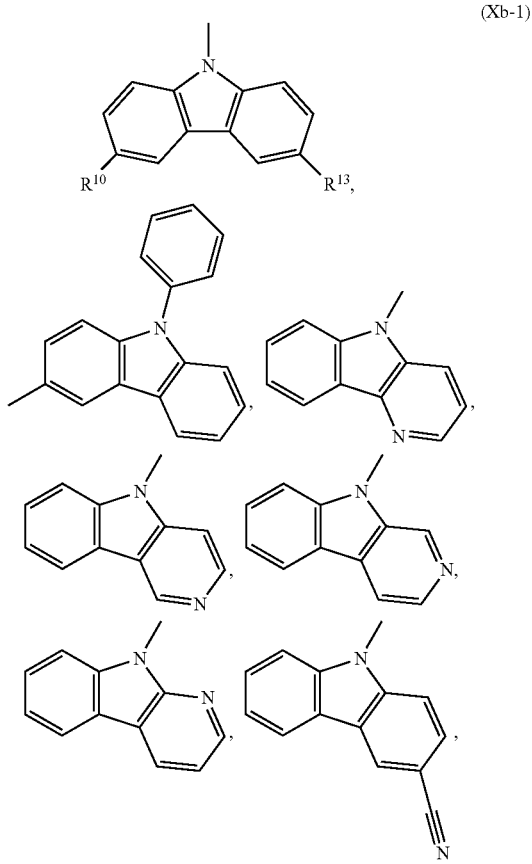

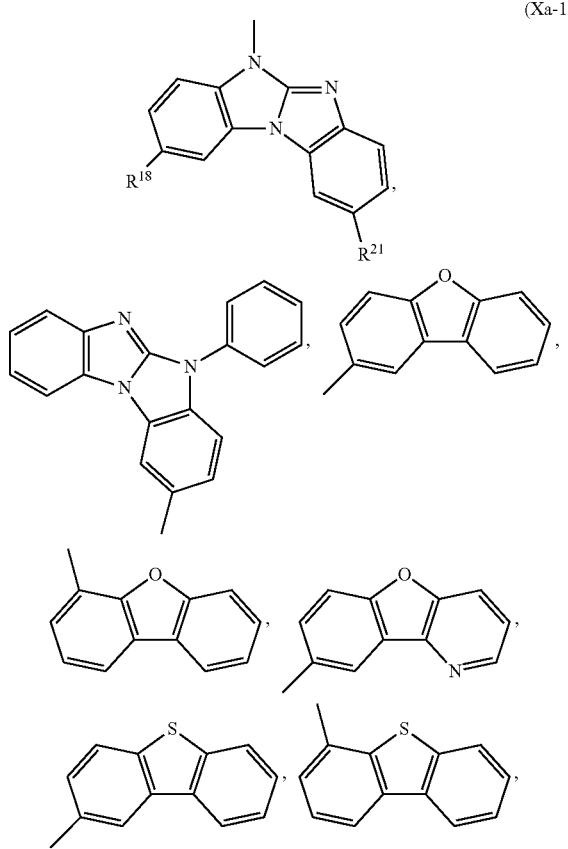

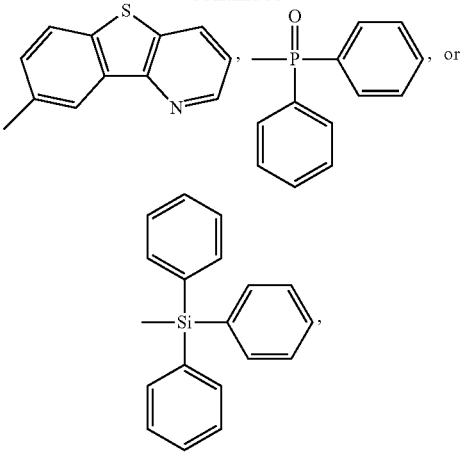

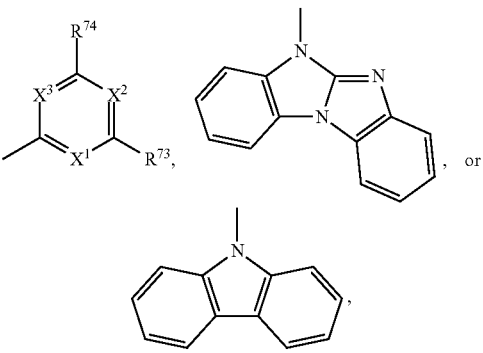

wherein
$X^4$, $X^5$ and $X^6$ are independently of each other N, or CH, with the proviso that at least one of
$X^4$, $X^5$ and $X^6$ represent N;
$R^{37}$, $R^{38}$, $R^{39}$, $R^{40}$ and $R^{41}$ are independently of each other H, or a phenyl group, and
$R^{75}$ and $R^{76}$ are independently of each other H, or a phenyl group.
$R^{10}$, $R^{13}$, $R^{18}$ and $R^{21}$ are independently of each other H, a group of formula wherein $X^1$, $X^2$ and $X^3$ are independently of each other N, or CH, with the proviso that at least one of $X^1$, $X^2$ and $X^3$ represent N, and
$R^{73}$ and $R^{74}$ are independently of each other H, or a phenyl group.

The group of formula $-[Ar^4]_d-[Ar^5]_e-[Ar^6]_f-A^2$ is more preferably H, or a group of formula (XIa)

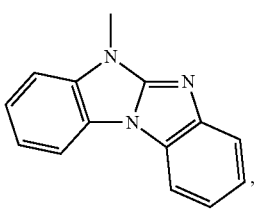 [SMILES: Cn1c2ccccc2n2c3ccccc3nc12]

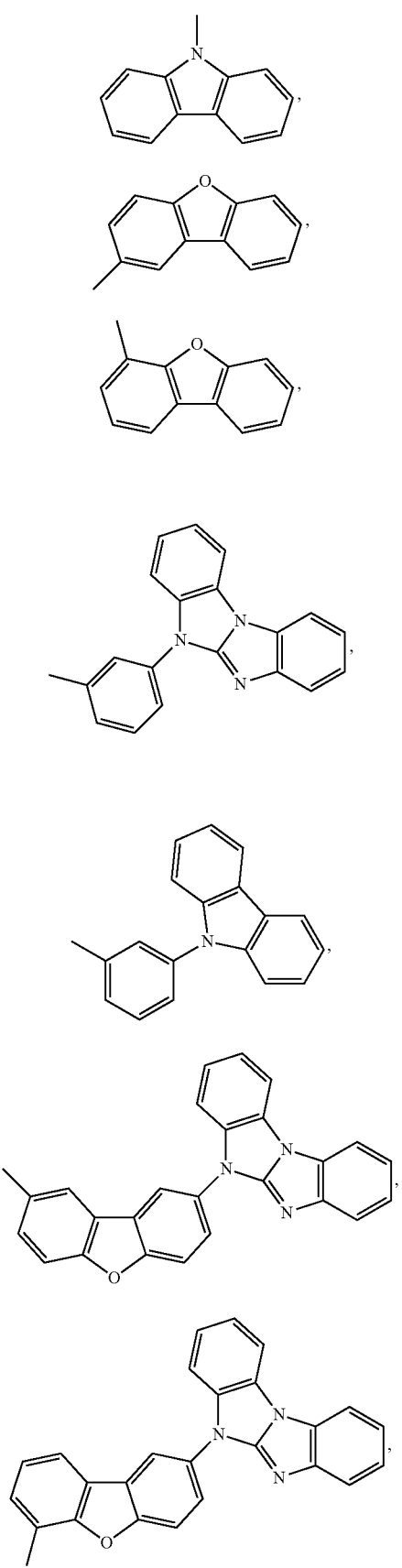
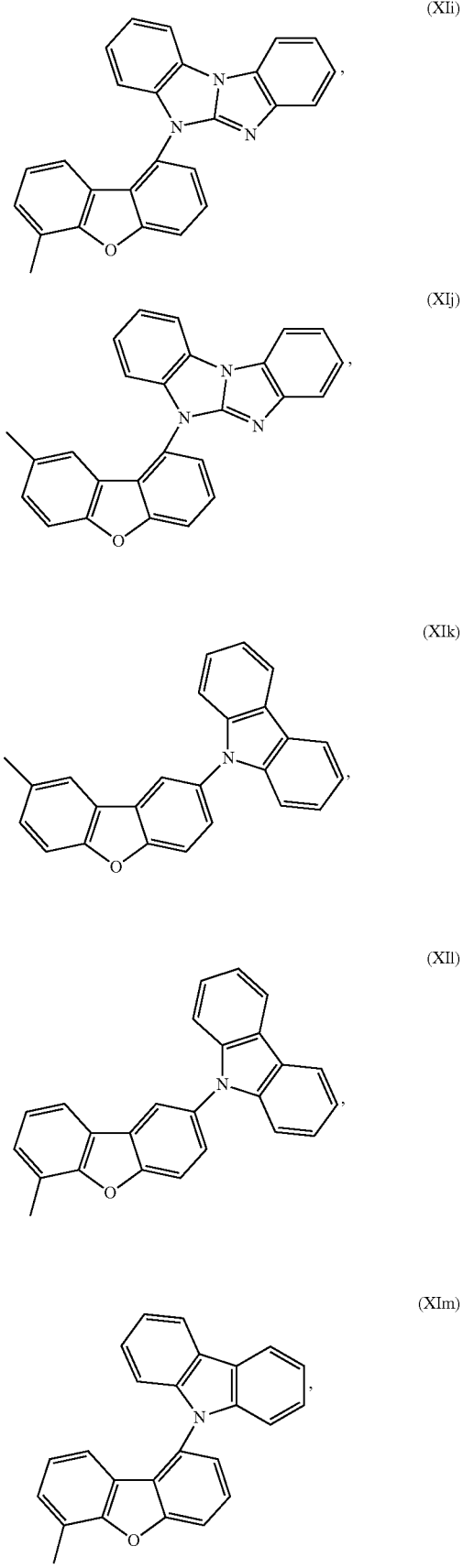

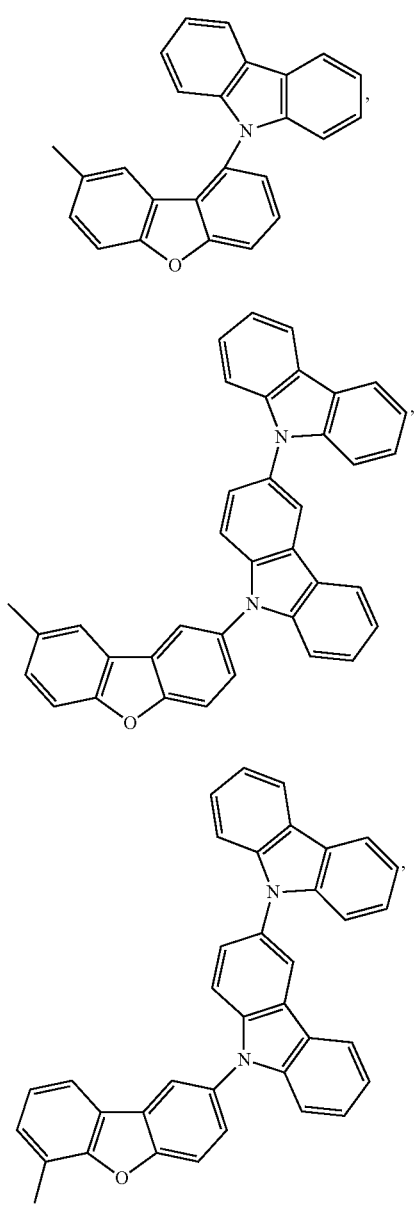
(XIn)
(XIo)
(XIp)
(XIq)
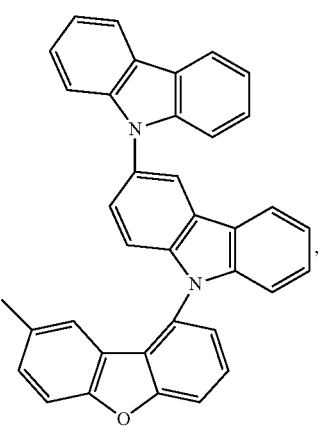
(XIr)
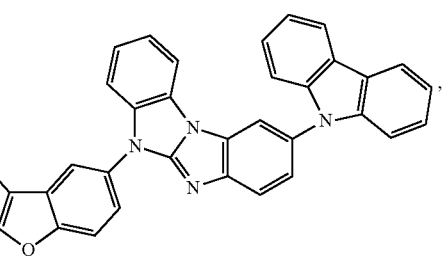
(XIs)
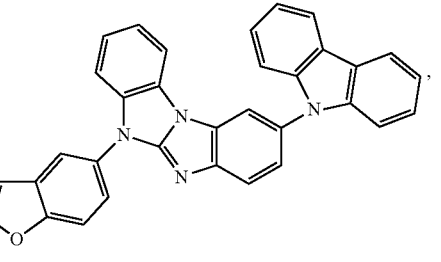
(XIt)
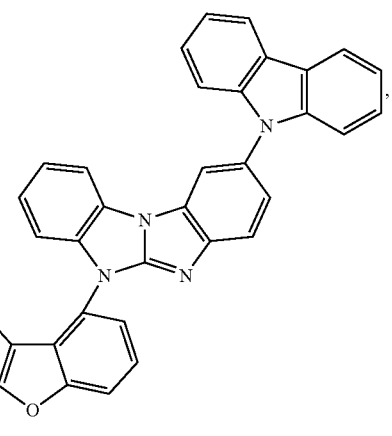
(XIu)

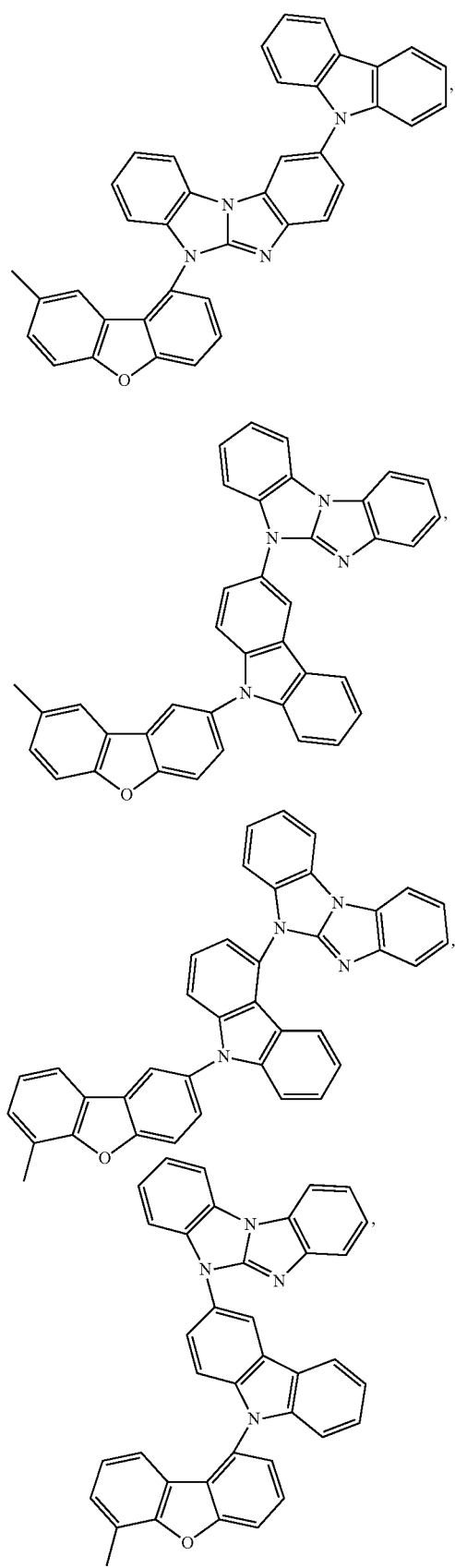
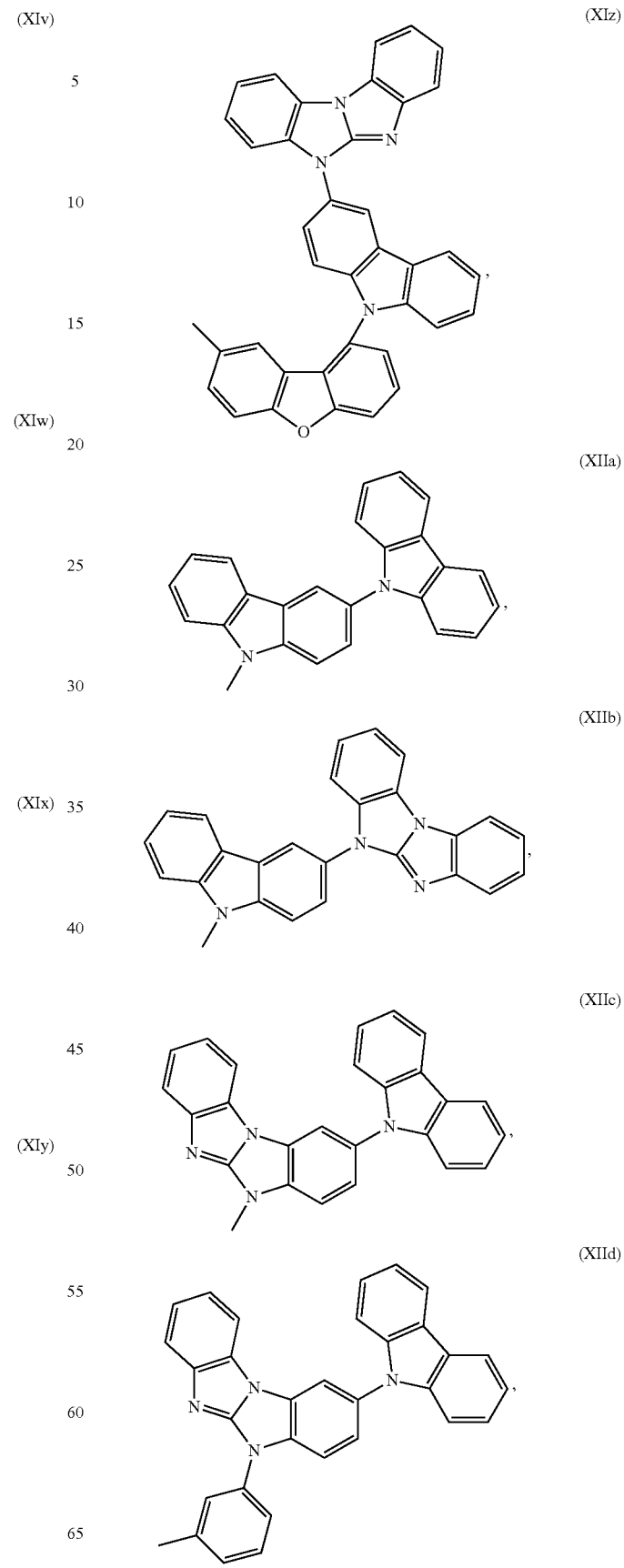

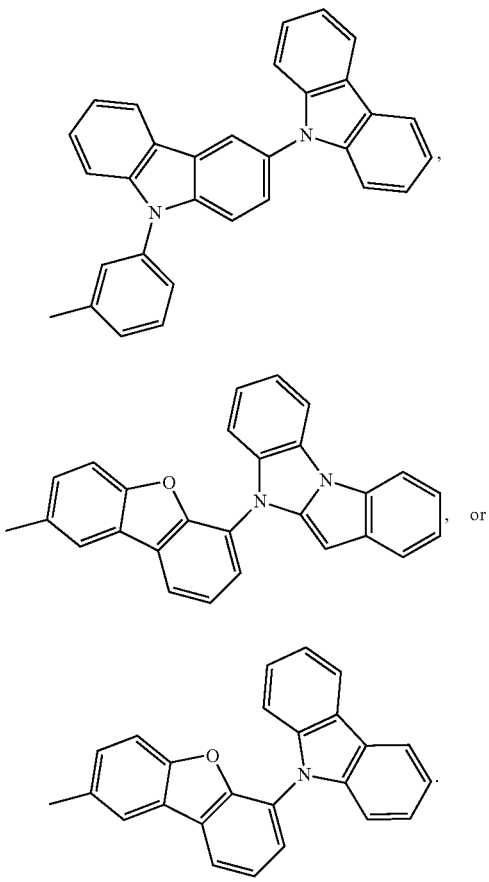

H, groups of formula (XIa), (XIb), (XIc), (XId), (XIe), (XIf), (XIg), (XIj), (XIk), (XIn), (XIo), (XIs), (XIw), (XIIa), (XIIb), (XIIc), (XIIe), (XIIf) and (XIIg) are most preferred.

Compounds of formula (I), wherein X is O, are more preferred than compounds of formula (I), wherein X is S.

Specific examples of the compound represented by the formula (I) are given below. The compound represented by the formula (I) is not limited to the following specific examples.

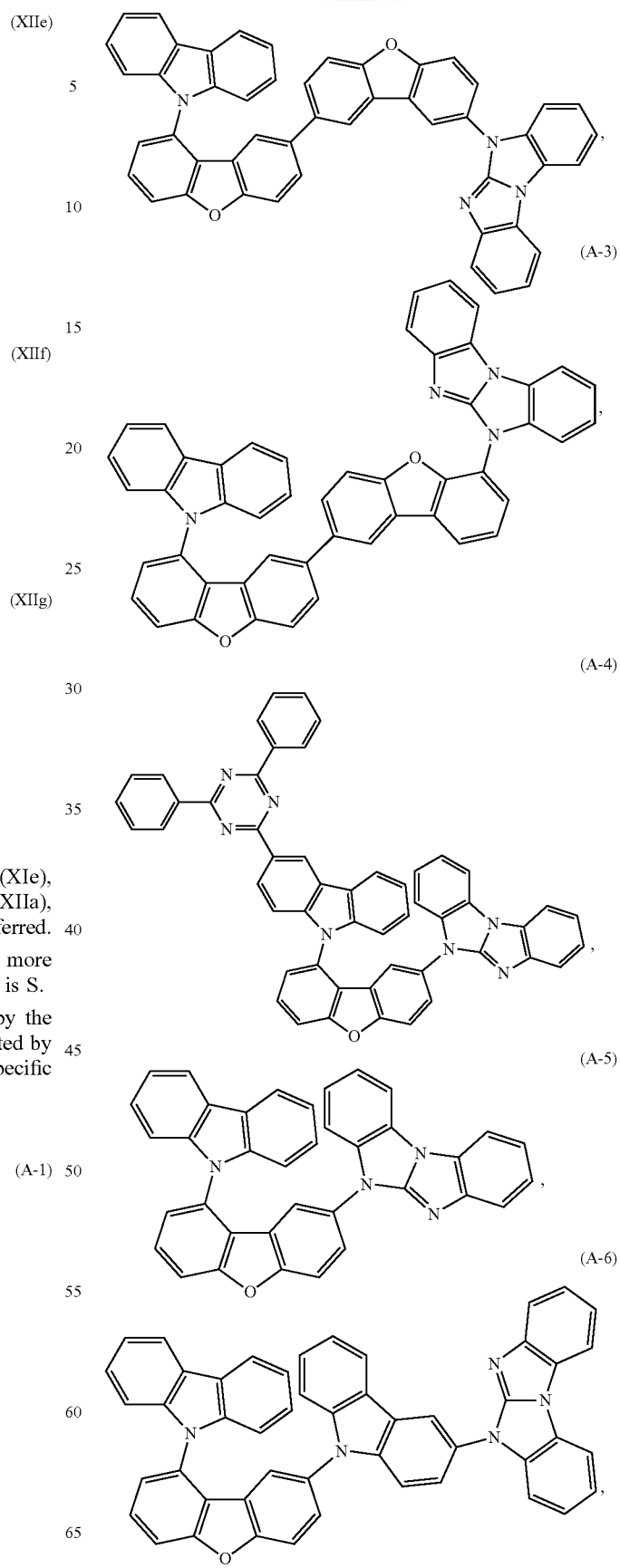

-continued
(A-7)
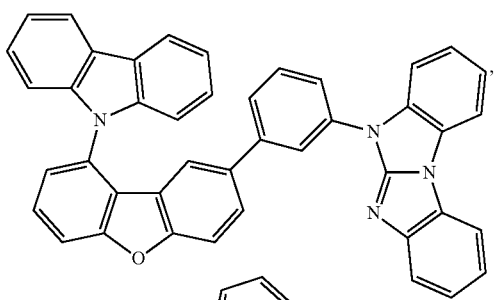
(A-8)
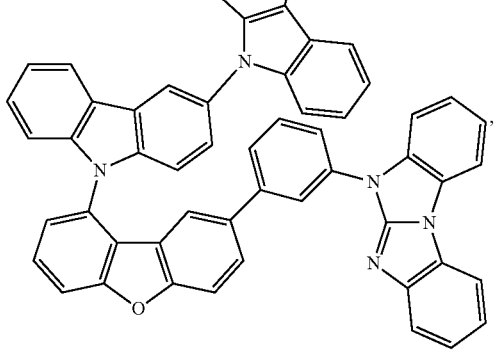
(A-9)
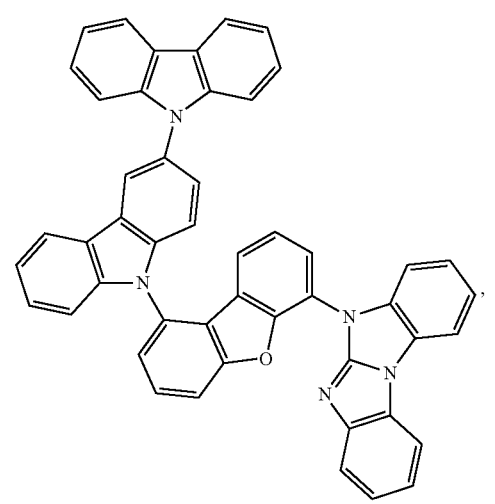
(A-10)
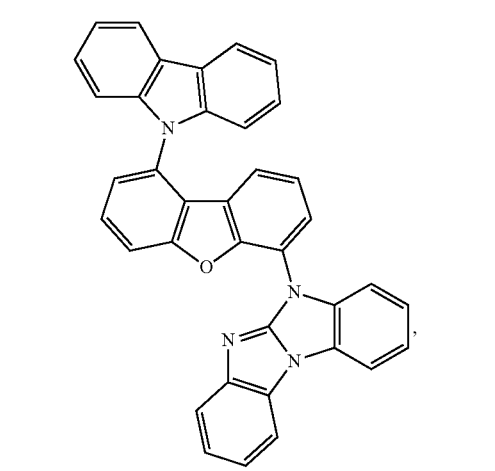
(A-11)
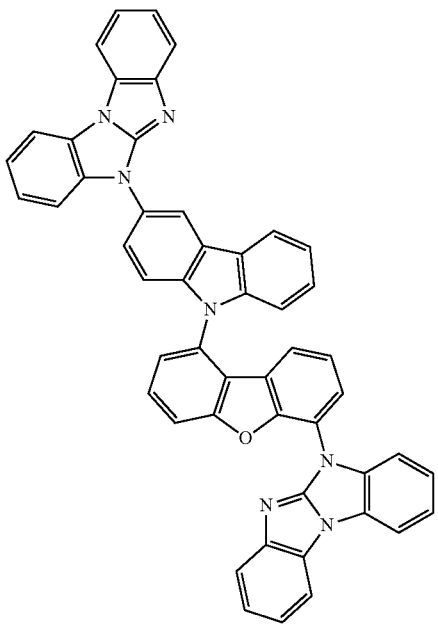
(A-12)
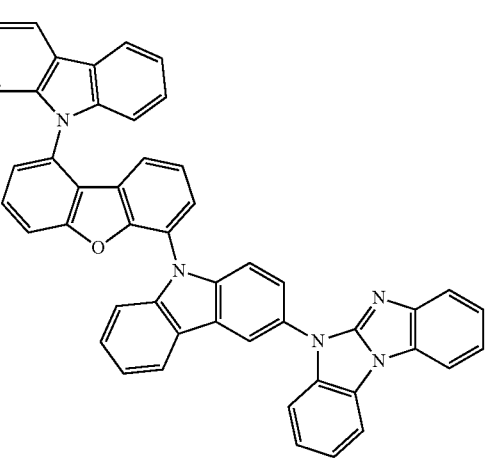
and
(A-13)
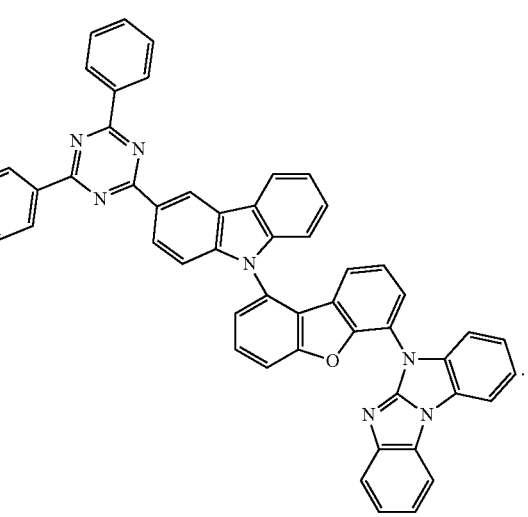

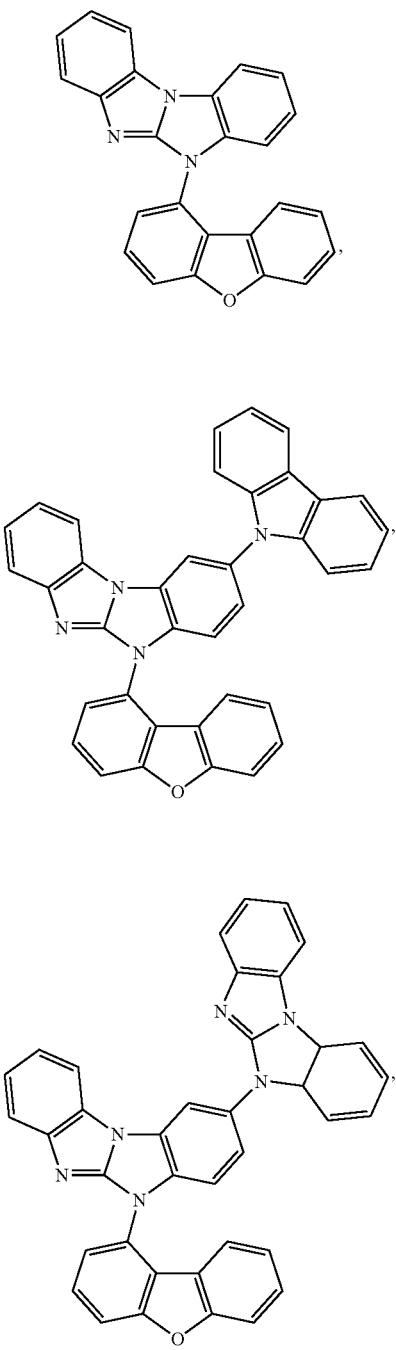
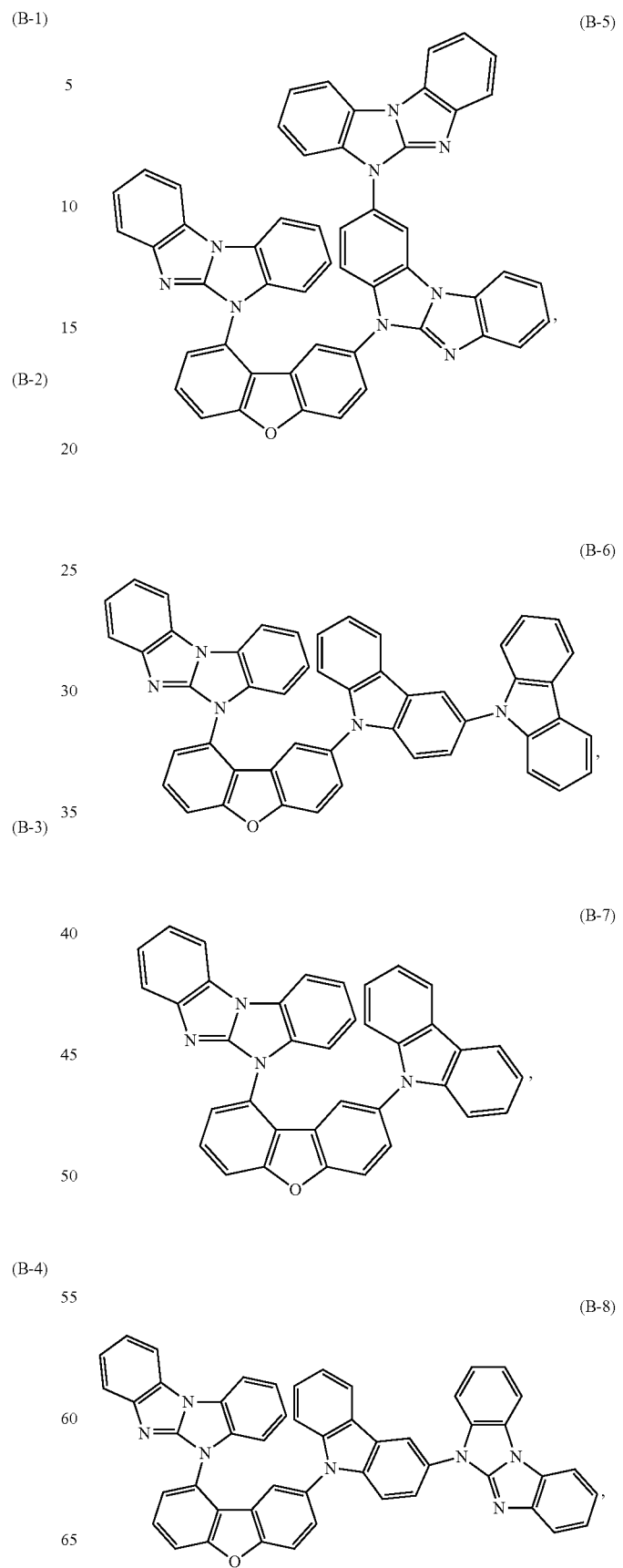

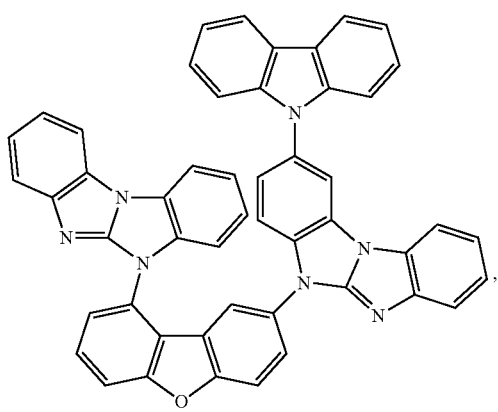
(B-9)
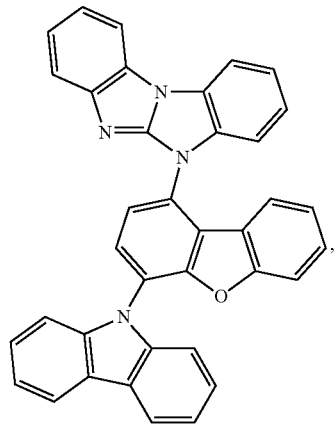
(B-12)
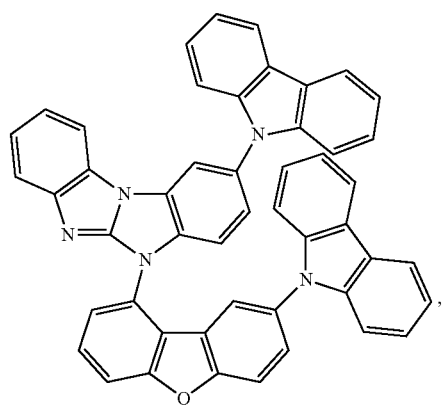
(B-10)
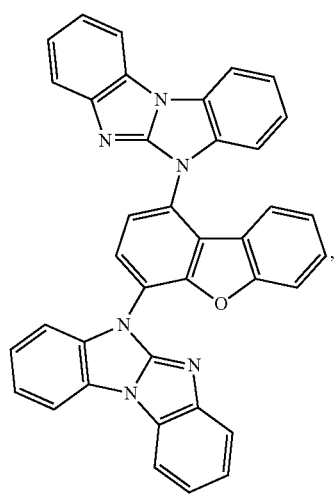
(B-13)
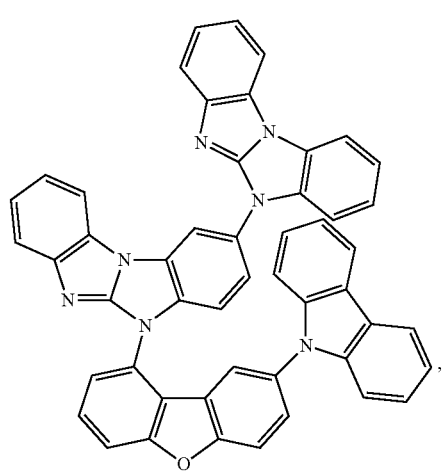
(B-11)
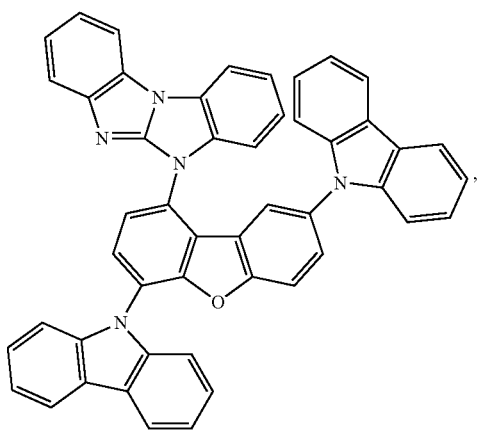
(B-14)

(B-15)
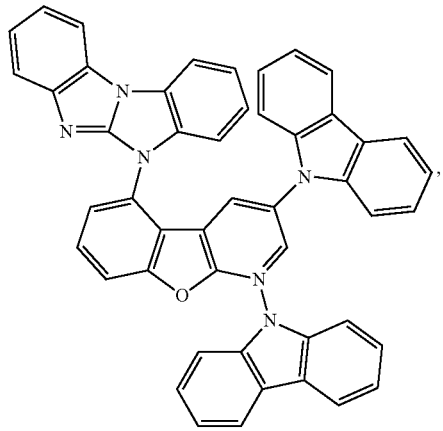
(B-19)
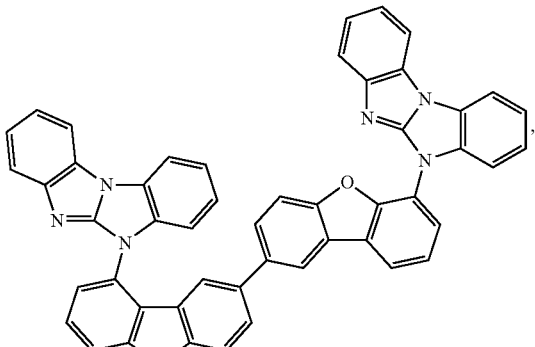
(B-16)
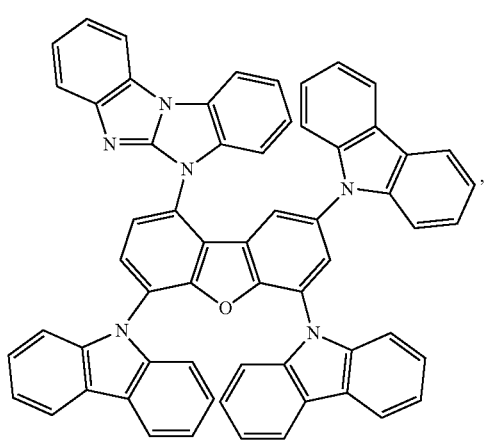
(B-20)
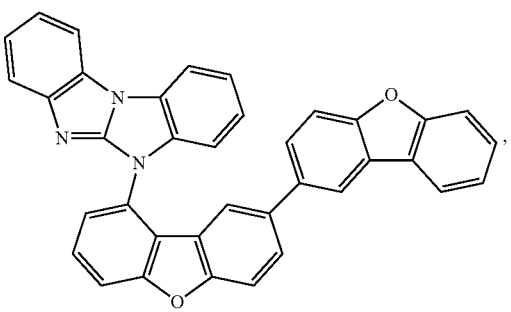
(B-21)
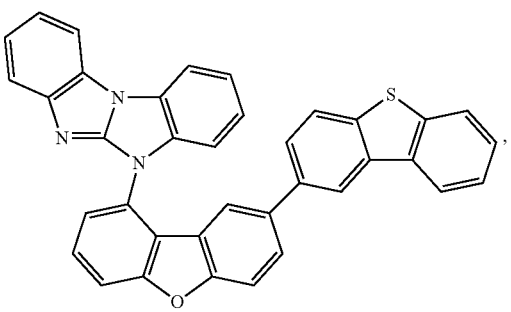
(B-17)
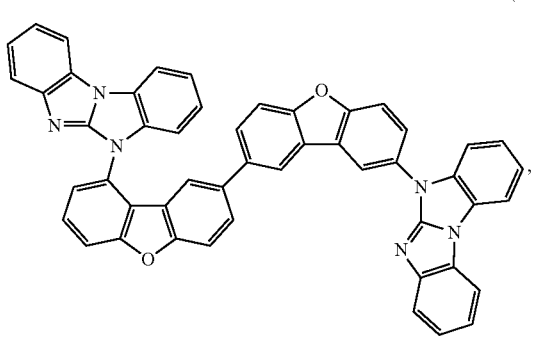
(B-18)
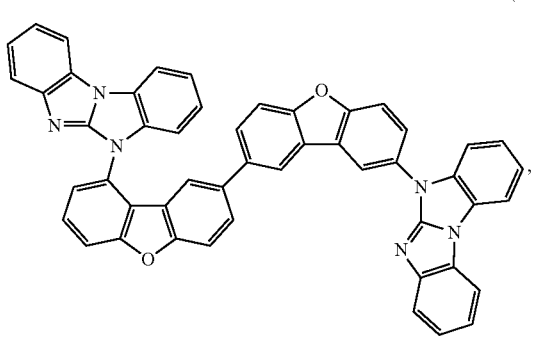
(B-22)
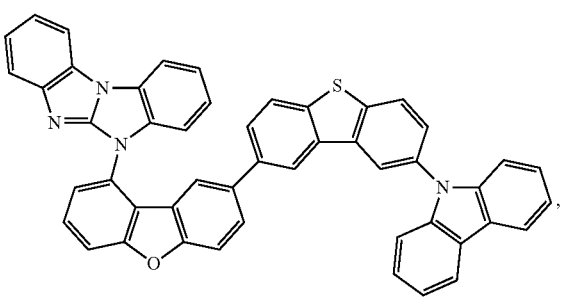

(B-23)
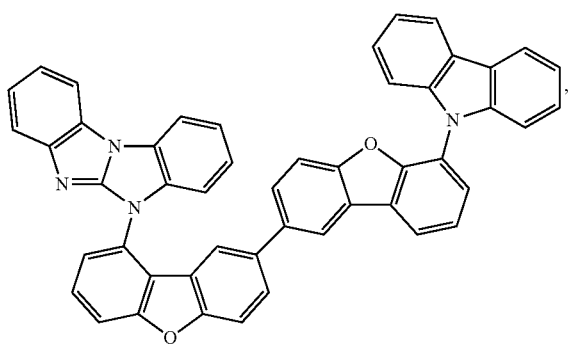
(B-24)
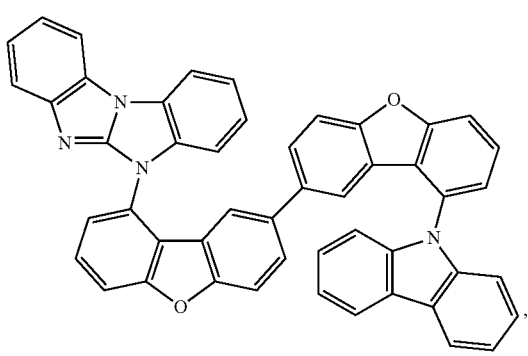
(B-25)
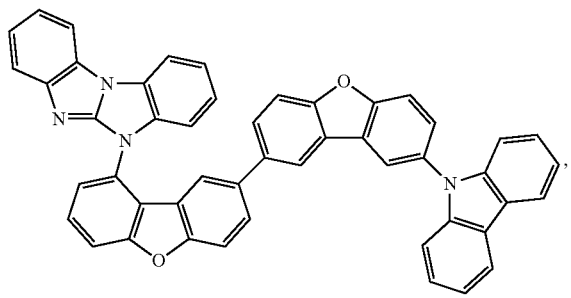
(B-26)
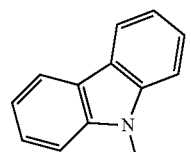
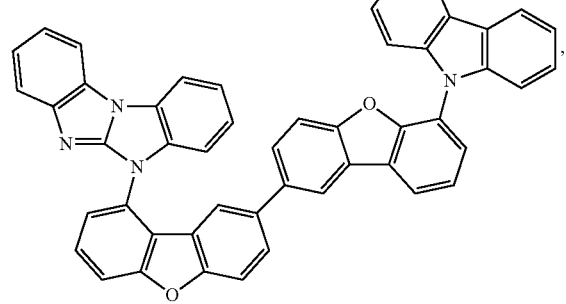
(B-27)
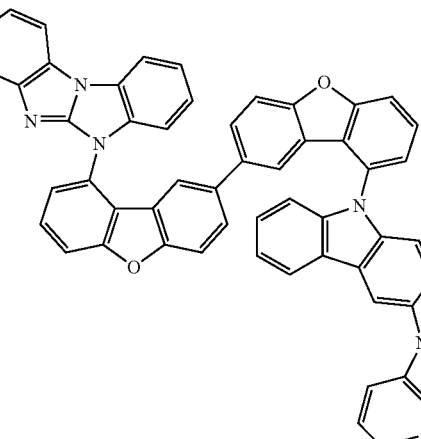
(B-28)
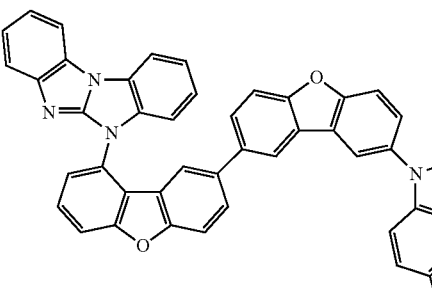
(B-29)
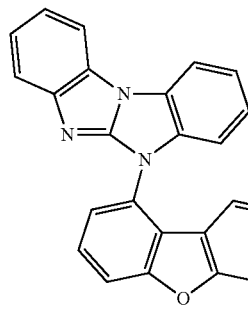
(B-30)
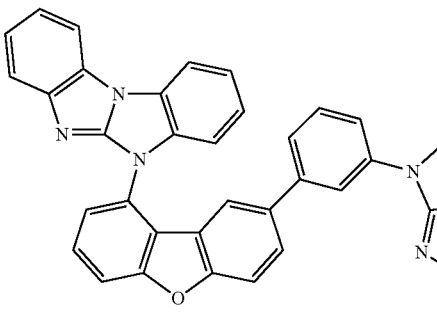

(B-31)
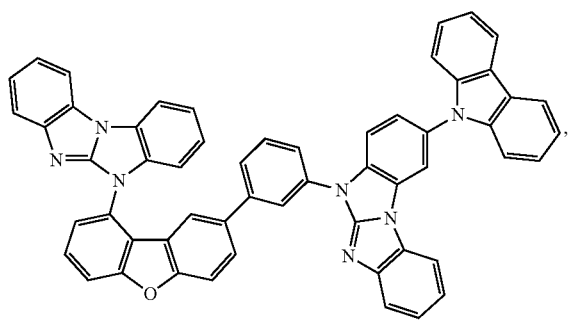
(B-32)
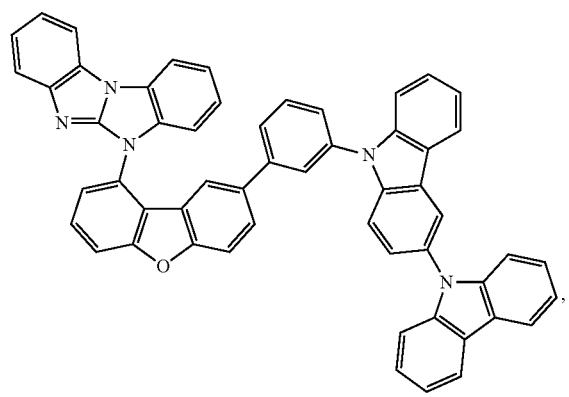
(B-33)
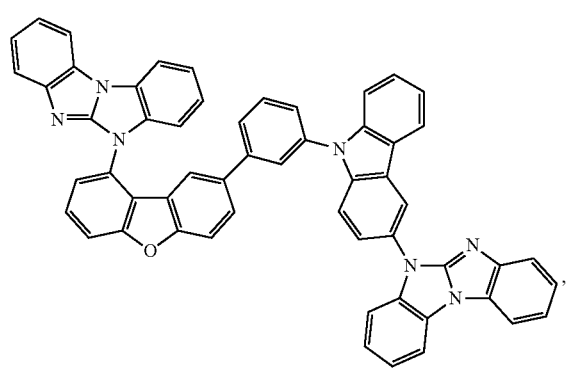
(B-34)
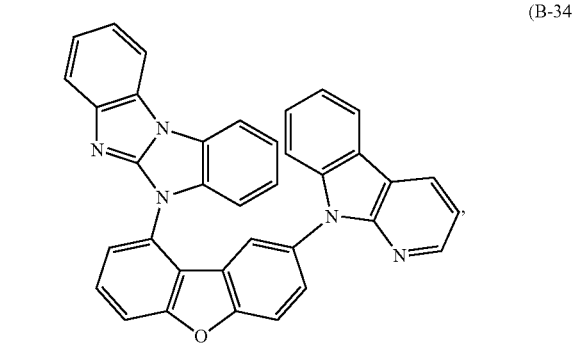
(B-35)
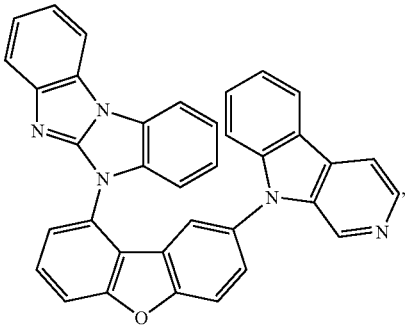
(B-36)
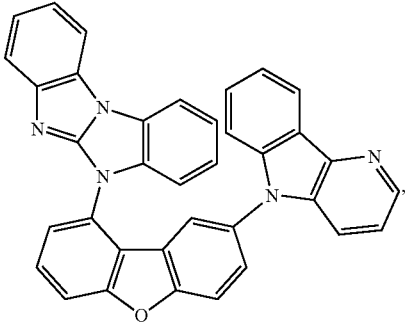
(B-37)
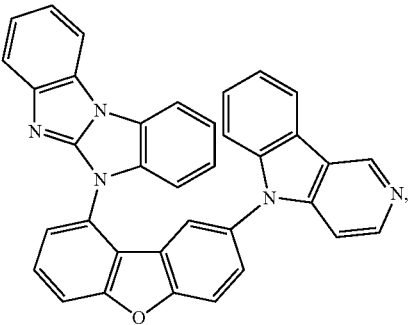
(B-38)
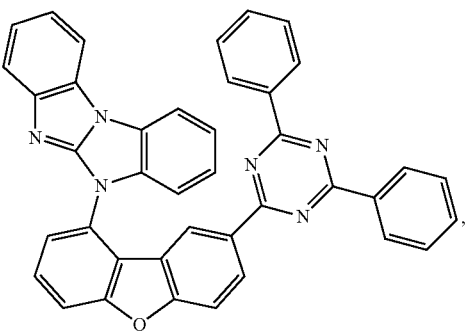

-continued
(B-39)
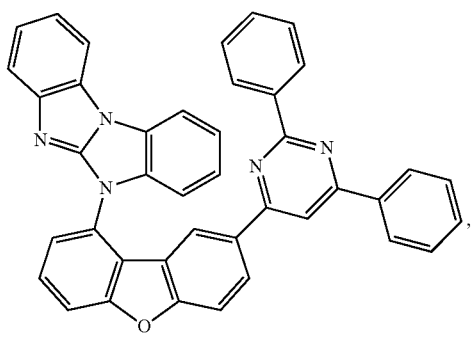
(B-40)
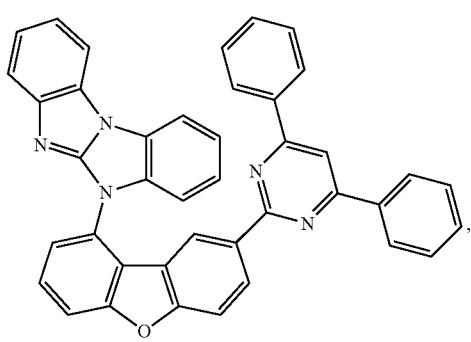
(B-41)
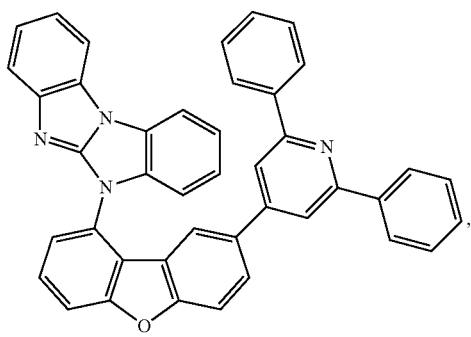
(B-42)
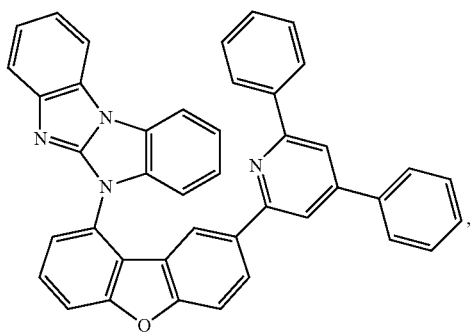
-continued
(B-43)
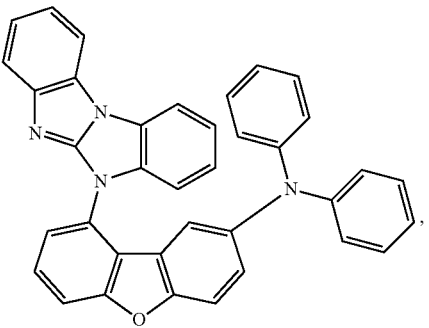
(B-44)
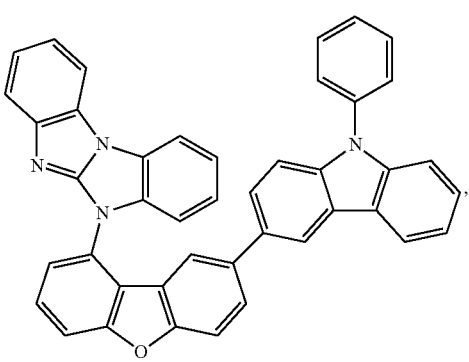
(B-45)
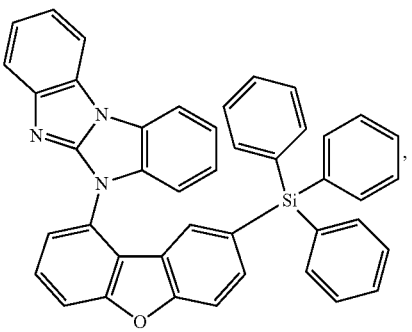
(B-46)
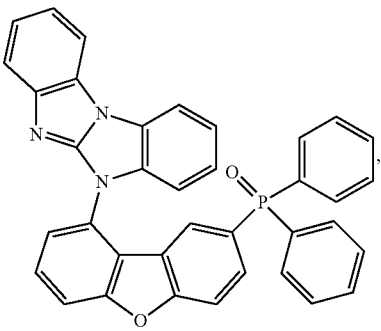

(B-47)
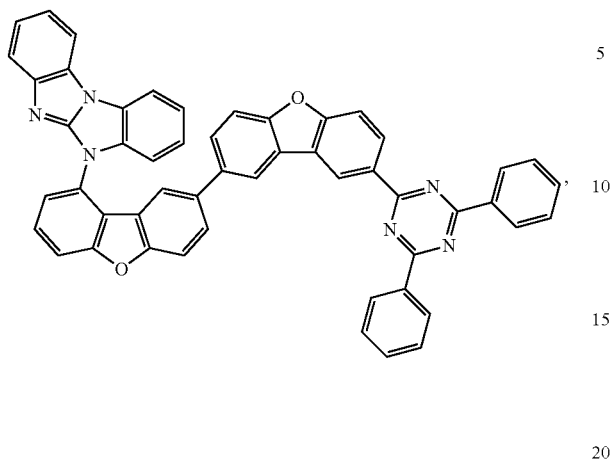
(B-48)
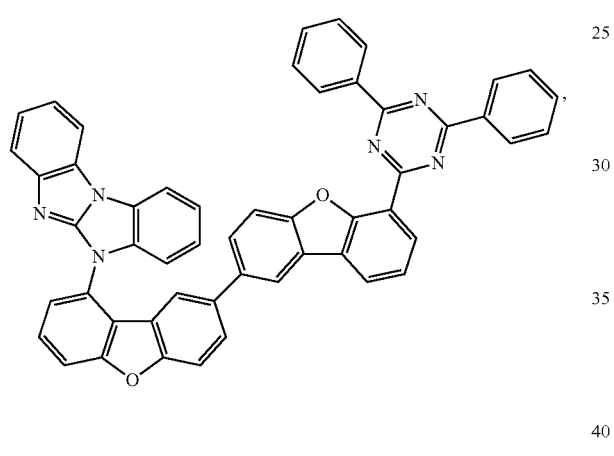
(B-49)
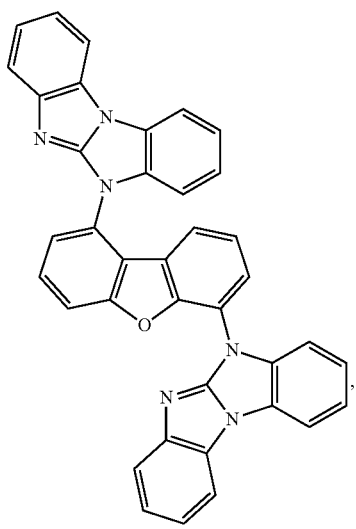
(B-50)
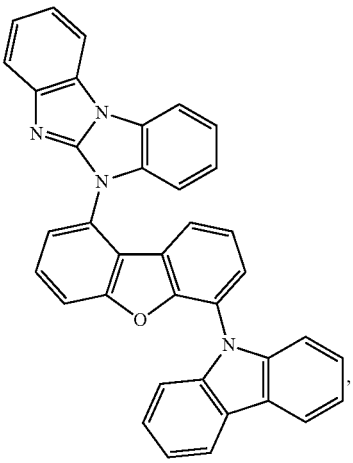
(B-51)
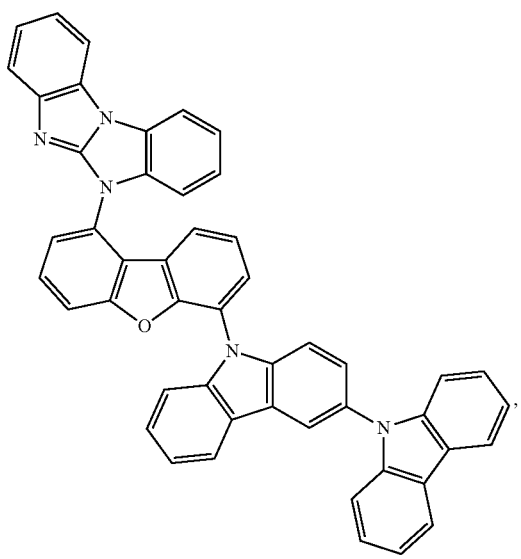
(B-52)
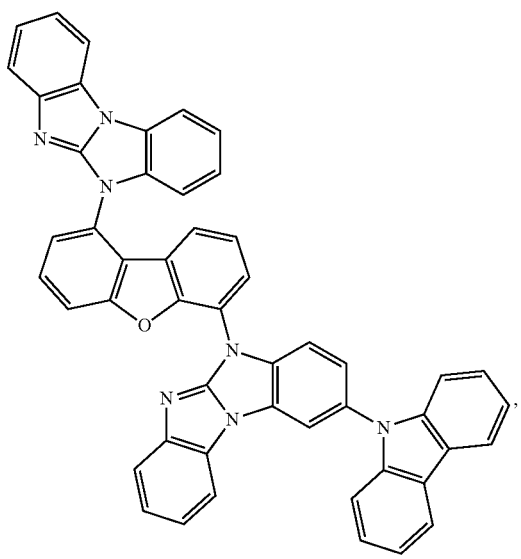

-continued
(B-53)
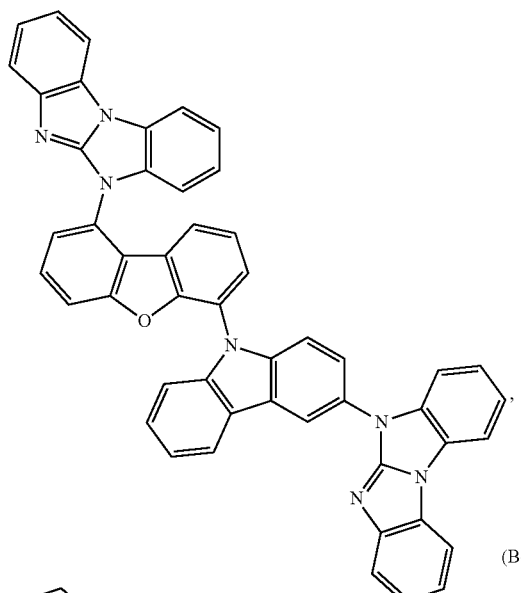
(B-54)
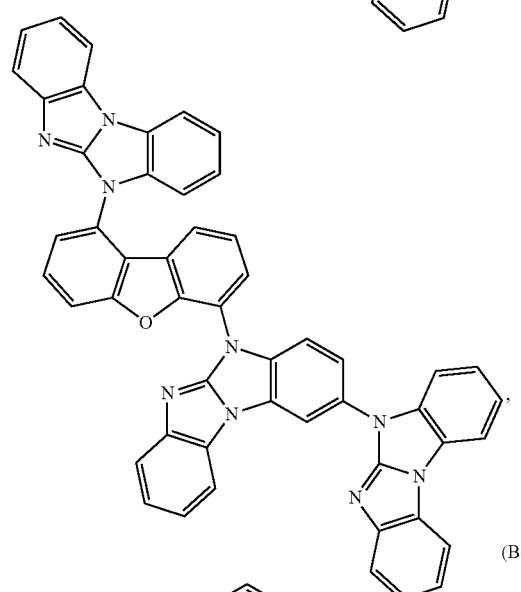
(B-55)
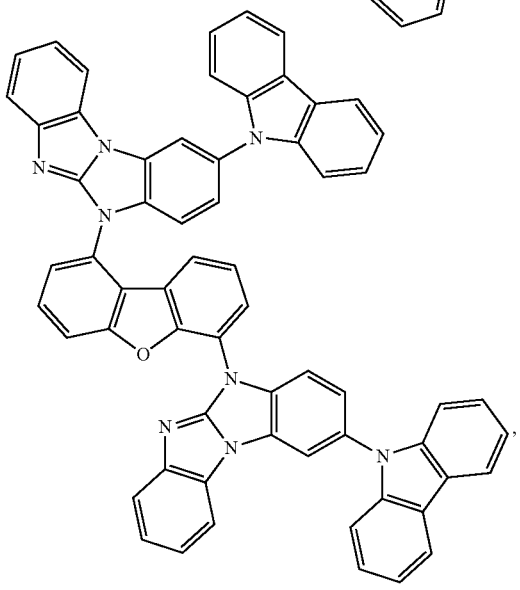
-continued
(B-56)
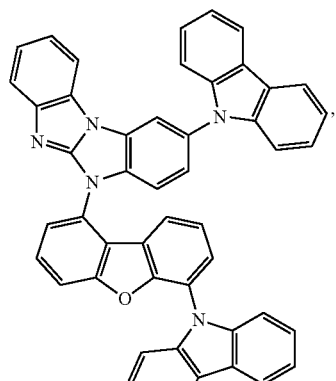
(B-57)
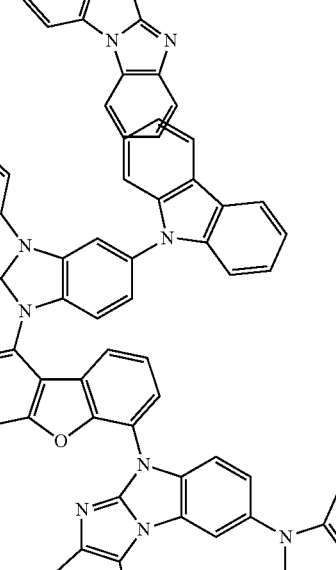
(B-58)
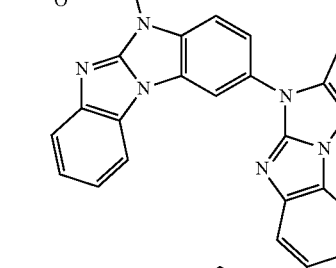

(B-59)
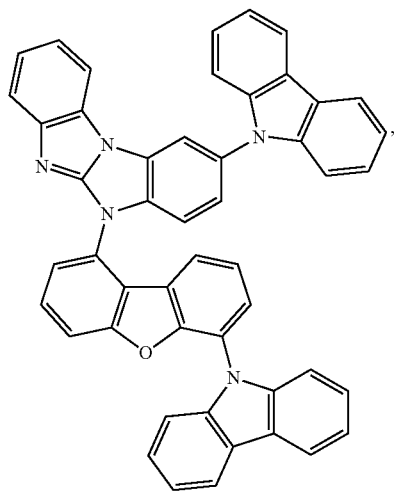
(B-60)
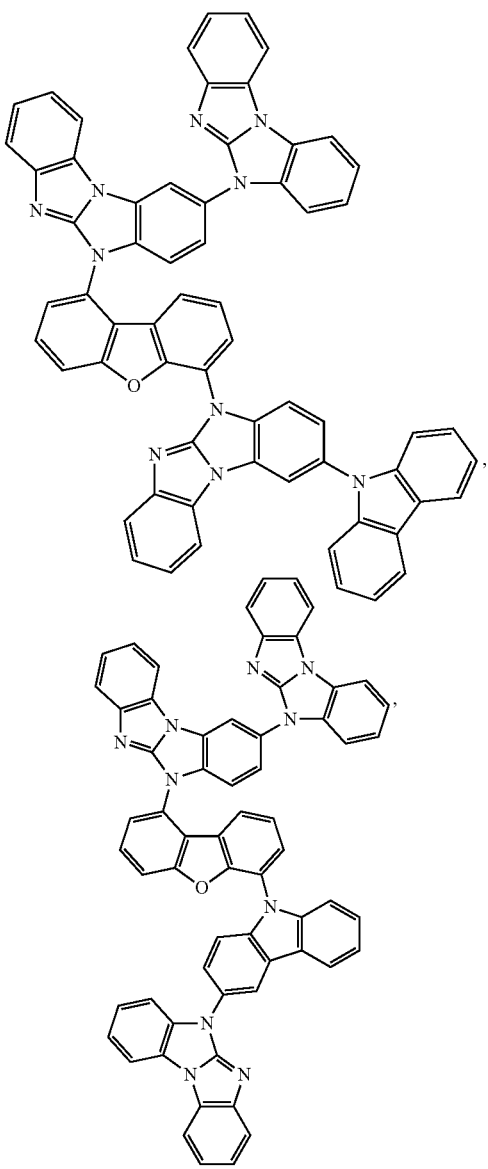
(B-62)
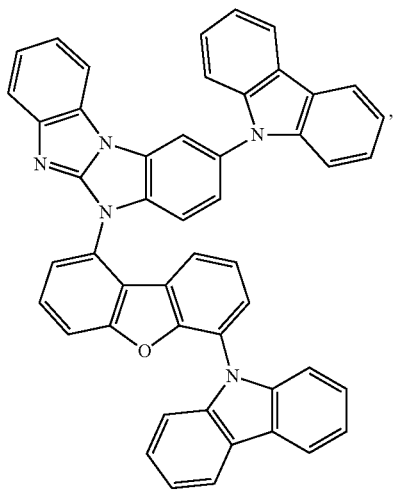
(B-63)
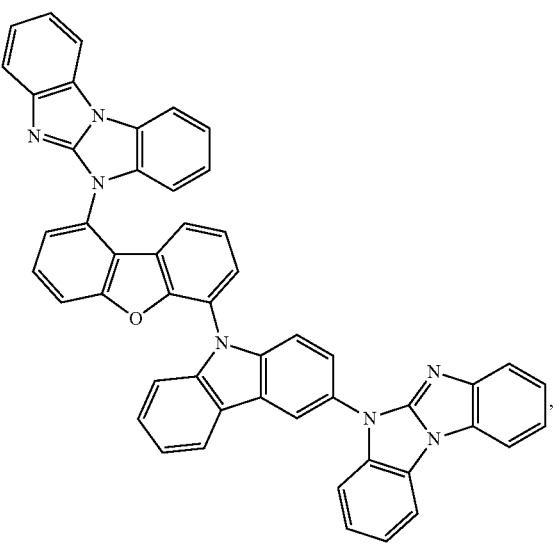
(B-61)
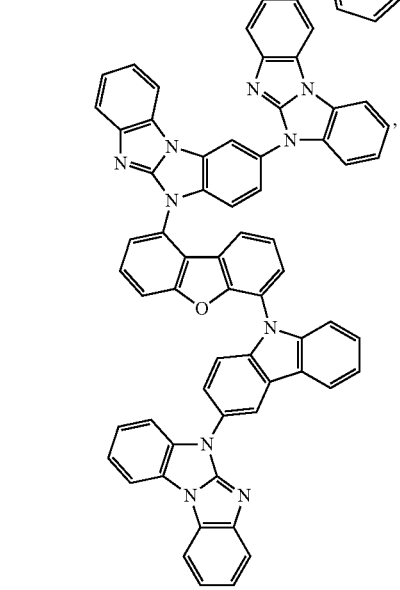
(B-64)
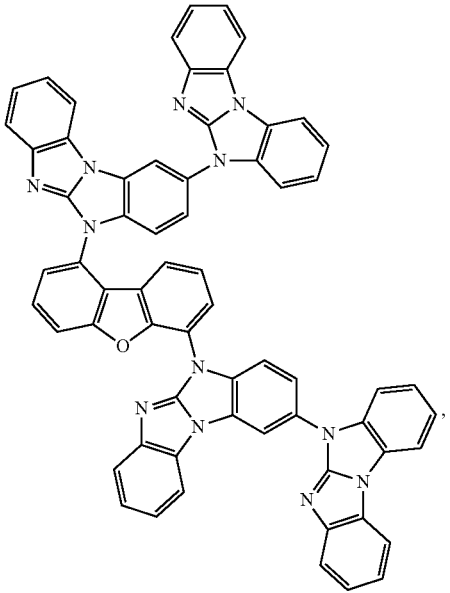

-continued
(B-65)
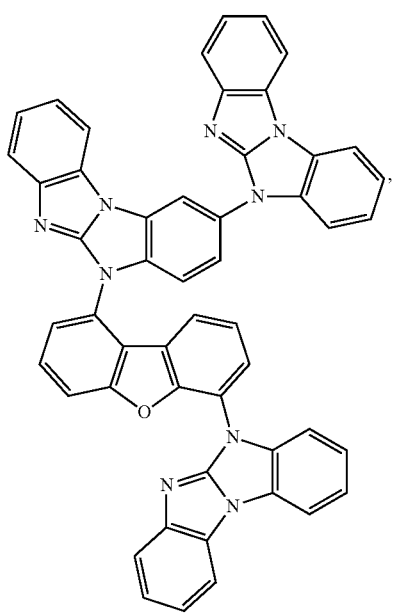
(B-66)
(B-67)
(B-68)
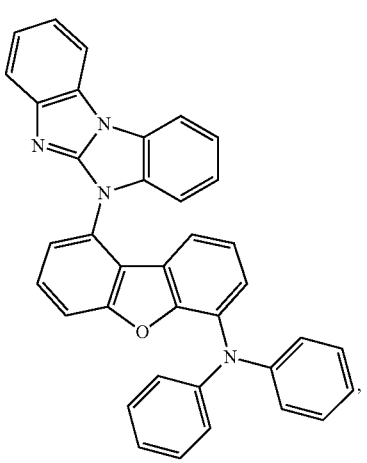
(B-69)
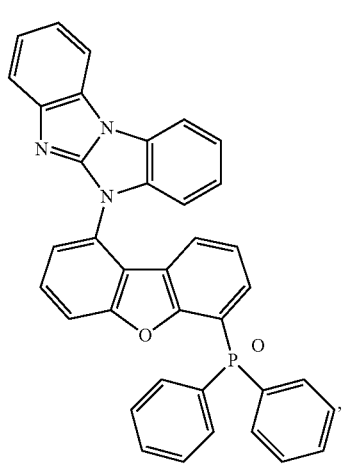
(B-70)
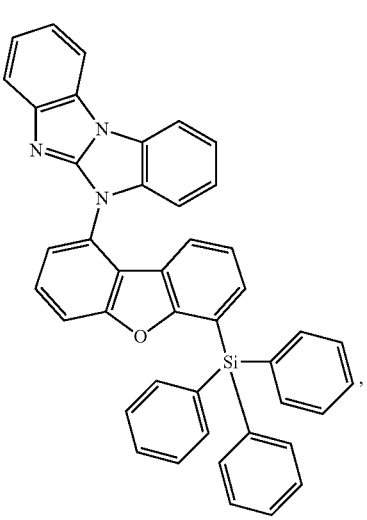

-continued
(B-71)
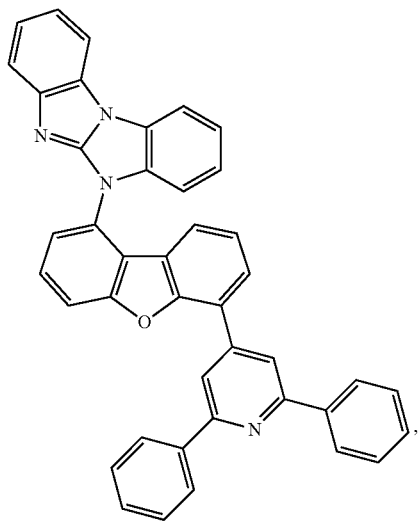
(B-74)
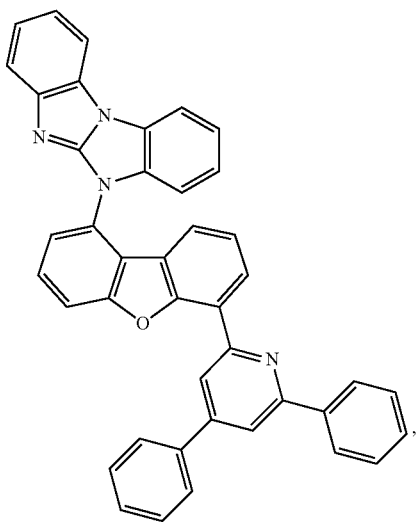
(B-72)
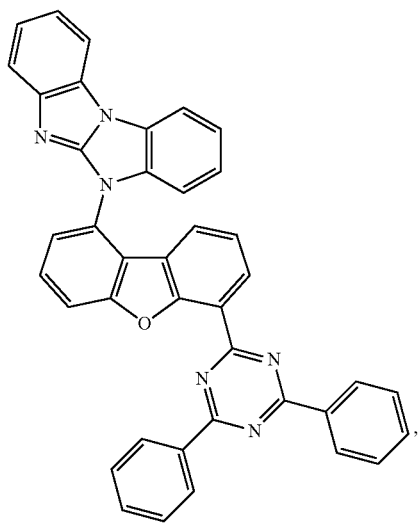
(B-75)
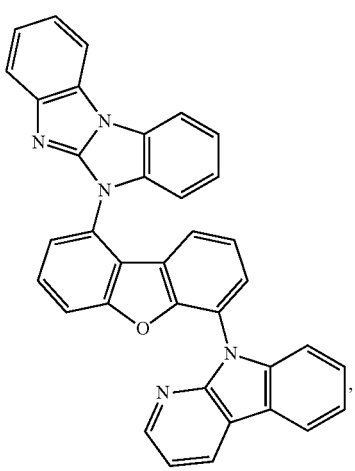
(B-73)
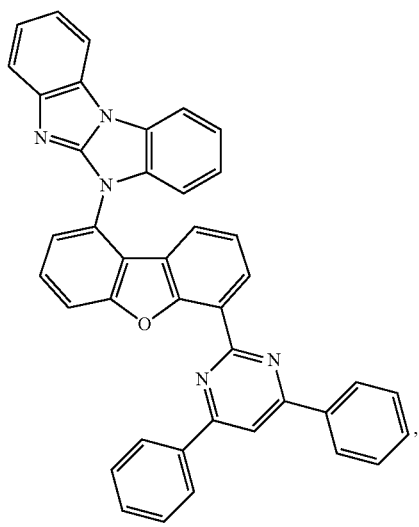
(B-76)
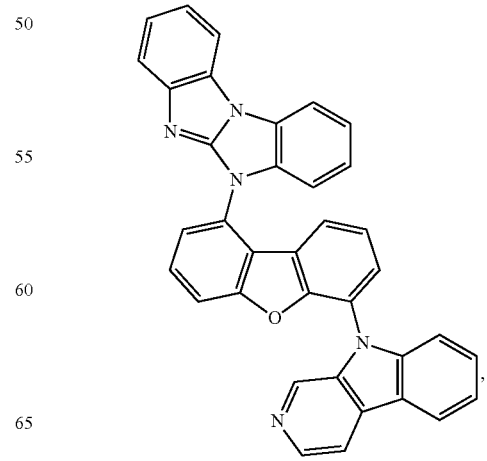

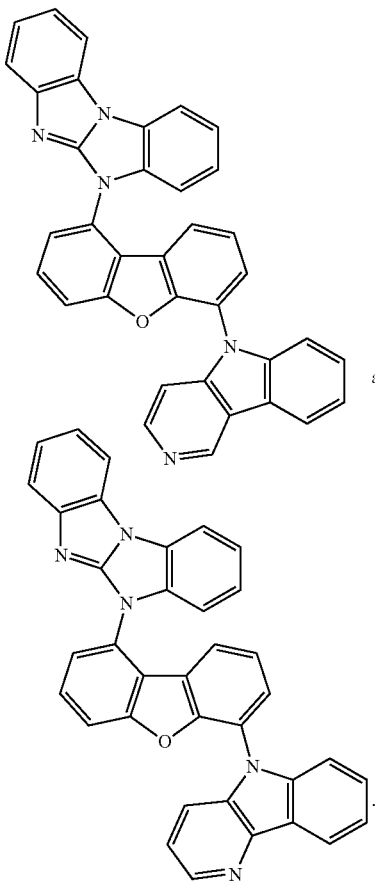
(B-77)

and (B-78)

Examples of preferred compounds of formula I are compounds (A-1), (A-2), (A-3), (A-5), (A-6), (A-7), (A-9), (A-10), (B-1), (B-2), (B-4), (B-6), (B-7), (B-11), (B-17), (B-18), (B-19), (B-20), (B-23), (B-24), (B-25), (B-28), (B-29), (B-30), (B-32), (B-33), (B-34), (B-35), (B-36), (B-38), (B-45), (B-46), (B-48), (B-49), (B-50), (B-51), (B-53), (B-55), (B-64), (B-65), (B-69), (B-70), (B-71) and (B-72) shown above. Compounds (A-2), (A-5), (A-7), (A-9), (A-10), (B-1), (B-2), (B-6), (B-7), (B-17), (B-18), (B-19), (B-23), (B-25), (B-28), (B-29), (B-30), (B-32), (B-49), (B-50), (B-51) and (B-53) are particularly preferred. Even more preferred are compounds of formula (Ia-1)

(Ia-2)

wherein
$R^4$ and $R^6$ are H, a group of formula (XIa), (XIb), (XIc), (XId), (XIe), (XIf), (XIg), (XIj), (XIk), (XIn), (XIo), (XIs), (XIw), (XIIa), (XIIb), (XIIc), (XIIe), (XIIf) and (XIIg) as defined above.

Y is a group of formula

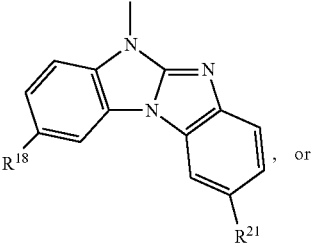
(Xa-1), or

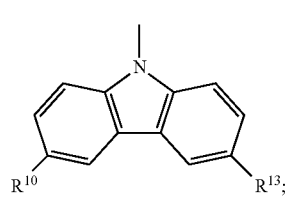
(Xb-1);

wherein
$R^{10}$ is H, or a group of formula $R^{18}$ is H, or a group of formula and
$R^{13}$ and $R^{21}$ are H, with the proviso that in case Y is a group of formula (Xb-1), $R^4$ and $R^6$ are a group of formula (XIa), (XIe), (XIg), (XIj), (XIs), (XIw), (XIIb), (XIIc), or (XIIf).

The synthesis of the compounds of formula (I) can be done in analogy to methods known in the literature.

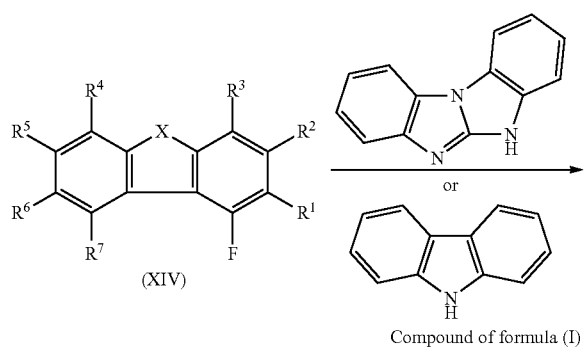

Compound of formula (I)

The introduction of the group

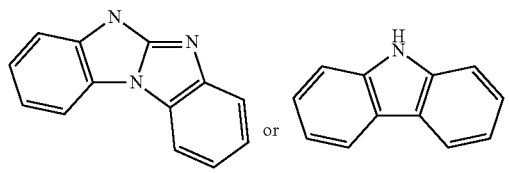

is performed in the presence of a base in a solvent at room temperature to reflux temperature of the solvent. Suitable bases are preferably selected from the group consisting of alkali metal and alkaline earth metal hydroxides such as NaOH, KOH, Ca(OH)$_2$, alkali metal hydrides such as NaH, KH, alkali metal amides such as NaNH$_2$, alkali metal or alkaline earth metal carbonates such as K$_2$CO$_3$ or Cs$_2$CO$_3$, alkali metal phosphates, such as, for example, K$_3$PO$_4$, and alkali metal alkoxides such as NaOMe, NaOEt. In addition, mixtures of the aforementioned bases are suitable. Particular preference is given to K$_3$PO$_4$ and K$_2$CO$_3$. Suitable solvents are, for example, (polar) aprotic solvents such as dimethyl sulfoxide, dimethylformamide, N-methyl-2-pyrrolidone (NMP), tridecane or alcohols.

The synthesis of compounds of formula (XIV),

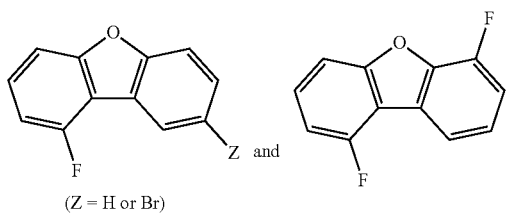

(Z = H or Br)

is described in Examples of the present application.

The synthesis of

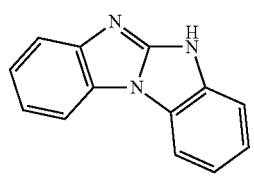 [SMILES: c1ccc2c(c1)nc1[nH]c3ccccc3n12]

is described, for example, in Achour, Reddouane; Zniber, Rachid, Bulletin des Societes Chimiques Beiges 96 (1987) 787-92.

Suitable base skeletons of the formula

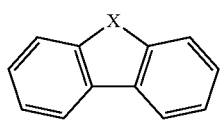

are either commercially available (especially in the cases when X is S, O, NH), or can be obtained by processes known to those skilled in the art. Reference is made to WO2010079051 and EP1885818.

The halogenation can be performed by methods known to those skilled in the art. Preference is given to brominating or iodinating in the 3 and 6 positions (dibromination) or in the 3 or 6 positions (monobromination) of the base skeleton of the formula 2,8 positions (dibenzofuran and dibenzothiophene) or 3,6 positions (carbazole).

Optionally substituted dibenzofurans, dibenzothiophenes and carbazoles can be dibrominated in the 2,8 positions (dibenzofuran and dibenzothiophene) or 3,6 positions (carbazole) with bromine or NBS in glacial acetic acid or in chloroform. For example, the bromination with Br$_2$ can be effected in glacial acetic acid or chloroform at low temperatures, e.g. 0° C. Suitable processes are described, for example, in M. Park, J. R. Buck, C. J. Rizzo, Tetrahedron, 54 (1998) 12707-12714 for X=NPh, and in W. Yang et al., J. Mater. Chem. 13 (2003) 1351 for X=S. In addition, 3,6-dibromocarbazole, 3,6-dibromo-9-phenylcarbazole, 2,8-dibromodibenzothiophene, 2,8-dibromodibenzofuran, 2-bromocarbazole, 3-bromodibenzothiophene, 3-bromodibenzofuran, 3-bromocarbazole, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150. Dibenzofuran (dibenzothiophene) can be monobrominated in the 3 position by a sequence known to those skilled in the art, comprising a nitration, reduction and subsequent Sandmeyer reaction.

Monobromination in the 2 position of dibenzofuran or dibenzothiophene and monobromination in the 3 position of carbazole are effected analogously to the dibromination, with the exception that only one equivalent of bromine or NBS is added.

Alternatively, it is also possible to utilize iodinated dibenzofurans, dibenzothiophenes and carbazoles. The preparation is described, inter alia, in Tetrahedron. Lett. 47 (2006) 6957-6960, Eur. J. Inorg. Chem. 24 (2005) 4976-4984, J. Heterocyclic Chem. 39 (2002) 933-941, J. Am. Chem. Soc. 124 (2002) 11900-11907, J. Heterocyclic Chem, 38 (2001) 77-87.

For the nucleophilic substitution, Cl- or F-substituted dibenzofurans, dibenzothiophenes and carbazoles are required. The chlorination is described, inter alia, in J. Heterocyclic Chemistry, 34 (1997) 891-900, Org. Lett., 6 (2004) 3501-3504; J. Chem. Soc. [Section] C: Organic, 16 (1971) 2775-7, Tetrahedron Lett. 25 (1984) 5363-6, J. Org. Chem. 69 (2004) 8177-8182. The fluorination is described in J. Org. Chem. 63 (1998) 878-880 and J. Chem. Soc., Perkin Trans. 2, 5 (2002) 953-957.

Compounds of formula

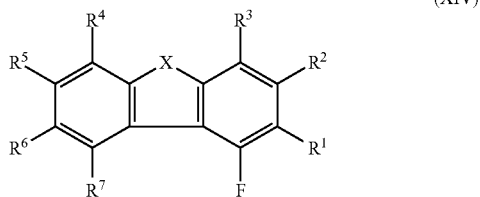

are new, represent intermediates in the synthesis of formula (I) and form a further subject of the present invention. X; $R^1$, $R^2$, $R^3$, $R^4$, $R^5$, $R^6$ and $R^7$ are defined above. For X; $R^1$, $R^2$, $R^3$, $R^4$, $R^5$, $R^6$ and $R^7$ the same preferences apply as for the compounds of formula (I).

Most preferred are compounds of formula

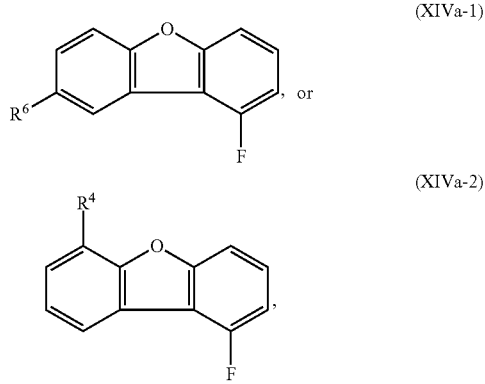

wherein $R^4$ and $R^6$ are a group of formula (XIa), (XIb), (XIc), (XId), (XIe), (XIf), (XIg), (XIh), (XIi), (XIj), (XIk), (XIl), (XIm), (XIn), (XIo), (XIp), (XIq), (XIr), (XIs), (XIt), (XIu), (XIv), (XIw), (XIx), (XIy), (XIz), (XIIa), (XIIb), (XIIc), (XIId), (XIIe), (XIIf), (XIIg), especially a group of formula (XIa), (XIb), (XIc), (XId), (XIe), (XIf), (XIg), (XIj), (XIk), (XIn), (XIo), (XIs), (XIw), (XIIa), (XIIb), (XIIc), (XIIe), (XIIf) and (XIIg).

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methyl-heptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, iso-butyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, iso-propoxy, n-butoxy, sec.-butoxy, isobutoxy, tert.-butoxy.

The term "cycloalkyl group" is typically $C_5$-$C_{18}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

$C_6$-$C_{24}$aryl ($C_6$-$C_{18}$aryl), which optionally can be substituted, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted. Phenyl, 1-naphthyl and 2-naphthyl are examples of a $C_6$-$C_{10}$aryl group.

$C_2$-$C_{30}$heteroaryl represents a ring with five to seven ring atoms or a condensed ring system, wherein nitrogen, oxygen or sulfur are the possible hetero atoms, and is typically a heterocyclic group with five to 30 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, benzimidazolo[2,1-b][1,3]benzothiazolyl, carbazolyl, or phenoxazinyl, which can be unsubstituted or substituted. Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group.

$C_6$-$C_{24}$arylene groups, which optionally can be substituted by G, are typically phenylene, 4-methylphenylene, 4-methoxyphenylene, naphthylene, especially 1-naphthylene, or 2-naphthylene, biphenylylene, terphenylylene, pyrenylene, 2- or 9-fluorenylene, phenanthrylene, or anthrylene, which may be unsubstituted or substituted. Preferred $C_6$-$C_{24}$arylene groups are 1,3-phenylene, 3,3'-biphenylylene, 3,3'-m-terphenylene, 2- or 9-fluorenylene, phenanthrylene, which may be unsubstituted or substituted.

$C_2$-$C_{30}$heteroarylene groups, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated-electrons such as thienylene, benzothiophenylene, dibenzothiophenylene, thianthrenylene, furylene, furfurylene, 2H-pyranylene, benzofuranylene, isobenzofuranylene, dibenzofuranylene, phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene, benzimidazo[1,2-a]benzimidazo-2,5-ylene, or phenoxazinylene, which can be unsubstituted or substituted. Preferred $C_2$-$C_{30}$heteroarylene groups are pyridylene, triazinylene, pyrimidinylene, carbazolylene, dibenzofuranylene and benzimidazo[1,2-a]benzimidazo-2,5-ylene

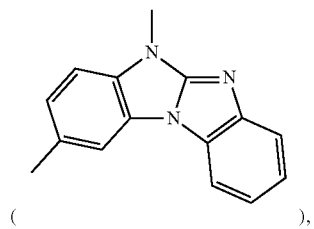 [SMILES: Cc1ccc2c(c1)n1c3ccccc3nc1n2C]

(    ), which can be unsubstituted or substituted, especially by $C_6$-$C_{10}$aryl, $C_6$-$C_{10}$aryl which is substituted by $C_1$-$C_4$alkyl; or $C_2$-$C_{14}$heteroaryl.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, or a cyano group. The $C_6$-$C_{24}$aryl ($C_6$-$C_{18}$aryl) and $C_2$-$C_{30}$heteroaryl groups are preferably substituted by one, or more $C_1$-$C_8$alkyl groups.

If a substituent occurs more than one time in a group, it can be different in each occurrence.

Halo-$C_1$-$C_8$alkyl is an alkyl group where at least one of the hydrogen atoms is replaced by a halogen atom. Examples are —$CF_3$, —$CF_2CF_3$, —$CF_2CF_2CF_3$, —$CF(CF_3)_2$, —$(CF_2)_3CF_3$, and —$C(CF_3)_3$.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—$CH(C_2H_5)$ $C_4H_9$), $CH_2$—$CH(OR^{y'})$—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H;

$C_1$-$C_8$alkylene-COO—$R^z$, e.g. $CH_2COOR^z$, $CH(CH_3)$ $COOR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above;

$CH_2CH_2$—O—CO—CH=$CH_2$; $CH_2CH(OH)CH_2$—O—CO—$C(CH_3)$=$CH_2$.

An alkyl group substituted by E is, for example, an alkyl group where at least one of the hydrogen atoms is replaced by F. Examples are —$CF_3$, —$CF_2CF_3$, —$CF_2CF_2CF_3$, —$CF(CF_3)_2$, —$(CF_2)_3CF_3$, and —$C(CF_3)_3$.

It has been found that the compounds of the formula I are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs), the compounds of the formula I being particularly suitable in OLEDs for use as matrix material in a light-emitting layer and/or as electron and/or exciton blocker material and/or as hole and/or exciton blocker material, especially in combination with a phosphorescence emitter. In the case of use of the inventive compounds of the formula I in OLEDs, OLEDs which have good efficiencies and a long lifetime and which can be operated especially at a low use and operating voltage are obtained. The inventive compounds of the formula I are suitable especially for use as matrix and/or charge/exciton blocker materials for blue and green emitters, for example light blue or deep blue emitters, these being especially phosphorescence emitters. Furthermore, the compounds of the formula I can be used as conductor/complementary materials in organic electronics applications selected from switching elements and organic solar cells.

The compounds of the formula I can be used as matrix material and/or charge/exciton blocker material and/or charge transport material (charge conductor material). The inventive compounds of the formula I are preferably used as matrix materials in organic electronics applications, especially in OLEDs.

In the emission layer or one of the emission layers of an OLED, it is also possible to combine an emitter material with a matrix material of the compound of the formula I and a further matrix material. This may achieve a high quantum efficiency of this emission layer.

When a compound of the formula I is used as matrix (host) material in an emission layer and additionally as charge/exciton blocker material, owing to the chemical identity or similarity of the materials, an improved interface between the emission layer and the adjacent charge/exciton blocker material, which can lead to a decrease in the voltage with equal luminance and to an extension of the lifetime of the OLED. Moreover, the use of the same material for charge/exciton blocker material and for the matrix of an emission layer allows the production process of an OLED to be simplified, since the same source can be used for the vapor deposition process of the material of one of the compounds of the formula I.

Suitable structures of organic electronic devices are known to those skilled in the art and are specified below.

The organic transistor generally includes a semiconductor layer formed from an organic layer with charge transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or charge transport capacity. In addition, it is possible for further layers known to those skilled in the art to be present in the organic solar cell. The layers with charge transport capacity may comprise the compounds of formula I.

It is likewise possible that the compounds of the formula I are present both in the light-emitting layer (preferably as matrix material) and in the blocking layers (as charge/exciton blockers).

The present invention further provides an organic light-emitting diode comprising an anode (a) and a cathode (i) and a light-emitting layer (e) arranged between the anode (a) and the cathode (i), and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the at least one compound of the formula I is present in the light-emitting layer (e) and/or in at least one of the further layers. The at least one compound of the formula I is preferably present in the light-emitting layer and/or the charge/exciton blocking layers.

In a preferred embodiment of the present invention, at least one compound of formula I, especially a compound of formula (Ia), very especially a compound of formula (Ia-1), or (Ia-2), is used as charge transport material. Examples of preferred compounds of formula I are compounds (A-1), (A-2), (A-3), (A-5), (A-6), (A-7), (A-9), (A-10), (B-1), (B-2), (B-4), (B-6), (B-7), (B-11), (B-17), (B-18), (B-19), (B-20), (B-23), (B-24), (B-25), (B-28), (B-29), (B-30), (B-32), (B-33), (B-34), (B-35), (B-36), (B-38), (B-45), (B-46), (B-48), (B-49), (B-50), (B-51), (B-53), (B-55), (B-64), (B-65), (B-69), (B-70), (B-71) and (B-72) shown above. Compounds (A-2), (A-5), (A-7), (A-9), (A-10), (B-1), (B-2), (B-6), (B-7), (B-17), (B-18), (B-19), (B-23), (B-25), (B-28), (B-29), (B-30), (B-32), (B-49), (B-50), (B-51) and (B-53) are particularly preferred.

In another preferred embodiment of the present invention, at least one compound of formula I, especially a compound of formula (Ia), very especially a compound of formula (Ia-1), or (Ia-2), is used as charge/exciton blocker material. Examples of preferred compounds of formula I are (A-1), (A-2), (A-3), (A-5), (A-6), (A-7), (A-9), (A-10), (B-1), (B-2), (B-4), (B-6), (B-7), (B-11), (B-17), (B-18), (B-19), (B-20), (B-23), (B-24), (B-25), (B-28), (B-29), (B-30), (B-32), (B-33), (B-34), (B-35), (B-36), (B-38), (B-45), (B-46), (B-48), (B-49), (B-50), (B-51), (B-53), (B-55), (B-64), (B-65), (B-69), (B-70), (B-71) and (B-72) shown above. Compounds (A-2), (A-5), (A-7), (A-9), (A-10), (B-1), (B-2), (B-6), (B-7), (B-17), (B-18), (B-19), (B-23), (B-25), (B-28), (B-29), (B-30), (B-32), (B-49), (B-50), (B-51) and (B-53) are particularly preferred.

The present application further relates to a light-emitting layer comprising at least one compound of the formula I.

Structure of the Inventive OLED

The inventive organic light-emitting diode (OLED) thus generally has the following structure: an anode (a) and a cathode (i) and a light-emitting layer (e) arranged between the anode (a) and the cathode (i).

The inventive OLED may, for example—in a preferred embodiment—be formed from the following layers:
1. Anode (a)
2. Hole transport layer (c)
3. Light-emitting layer (e)
4. Blocking layer for holes/excitons (f)
5. Electron transport layer (g)
6. Cathode (i)

Layer sequences different than the aforementioned structure are also possible, and are known to those skilled in the art. For example, it is possible that the OLED does not have all of the layers mentioned; for example, an OLED with layers (a) (anode), (e) (light-emitting layer) and (i) (cathode) is likewise suitable, in which case the functions of the layers (c) (hole transport layer) and (f) (blocking layer for holes/excitons) and (g) (electron transport layer) are assumed by the adjacent layers. OLEDs which have layers (a), (c), (e) and (i), or layers (a), (e), (f), (g) and (i), are likewise suitable. In addition, the OLEDs may have a blocking layer for electrons/excitons (d) between the hole transport layer (c) and the Light-emitting layer (e).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole transport layer, in one embodiment, may simultaneously block excitons and/or electrons.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used in accordance with the invention.

In a preferred embodiment the OLED according to the present invention comprises in this order:
(a) an anode,
(b) optionally a hole injection layer,
(c) optionally a hole transport layer,
(d) optionally an exciton blocking layer
(e) an emitting layer,
(f) optionally a hole/exciton blocking layer
(g) optionally an electron transport layer,
(h) optionally an electron injection layer, and
(i) a cathode.

In a particularly preferred embodiment the OLED according to the present invention comprises in this order:
(a) an anode,
(b) optionally a hole injection layer,
(c) a hole transport layer,
(d) an exciton blocking layer
(e) an emitting layer,
(f) a hole/exciton blocking layer
(g) an electron transport layer, and
(h) optionally an electron injection layer, and
(i) a cathode.

The properties and functions of these various layers, as well as example materials are known from the prior art and are described in more detail below on basis of preferred embodiments.

Anode (a):

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

Hole Injection Layer (b):

Generally, injection layers are comprised of a material that may improve the injection of charge carriers from one layer, such as an electrode or a charge generating layer, into an adjacent organic layer. Injection layers may also perform a charge transport function. The hole injection layer may be any layer that improves the injection of holes from anode into an adjacent organic layer. A hole injection layer may comprise a solution deposited material, such as a spin-coated polymer, or it may be a vapor deposited small molecule material, such as, for example, CuPc or MTDATA. Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

Hole Transport Layer (c):

Either hole-transporting molecules or polymers may be used as the hole transport material. Suitable hole transport materials for layer (c) of the inventive OLED are disclosed, for example, in Kirk-Othmer Encyclopedia of Chemical Technology, 4th Edition, Vol. 18, pages 837 to 860, 1996, US20070278938, US2008/0106190, US2011/0163302 (tri-arylamines with (di)benzothiophen/(di)benzofuran; Nan- Xing Hu et al. Synth. Met. 111 (2000) 421 (indolocarbazoles), WO2010002850 (substituted phenylamine compounds) and WO2012/16601 (in particular the hole transport materials mentioned on pages 16 and 17 of WO2012/16601). Combination of different hole transport material may be used. Reference is made, for example, to WO2013/022419, wherein

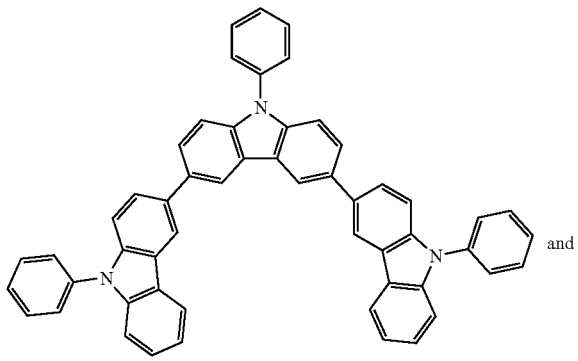

(HTL1-1)

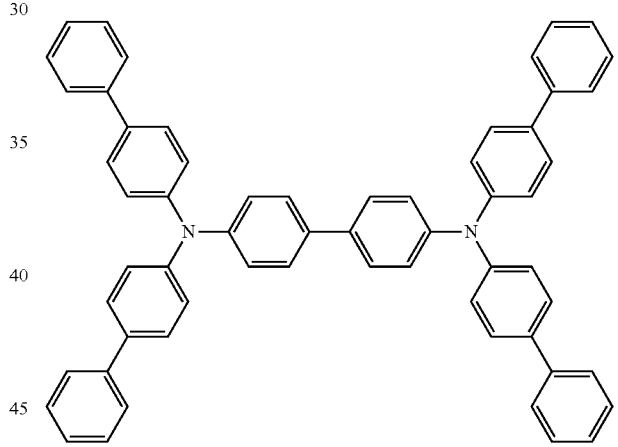

(HTL2-1)

constitute the hole transport layer.

Customarily used hole-transporting molecules are selected from the group consisting of

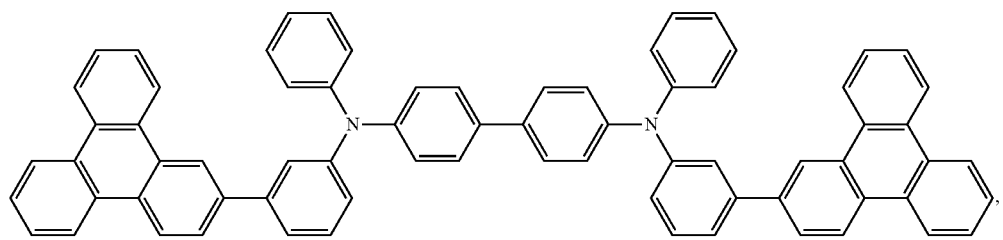

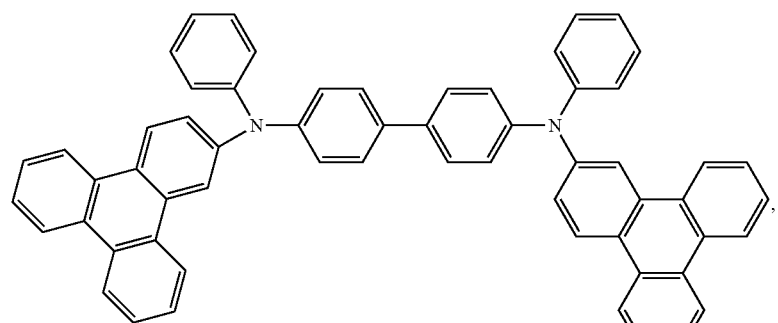
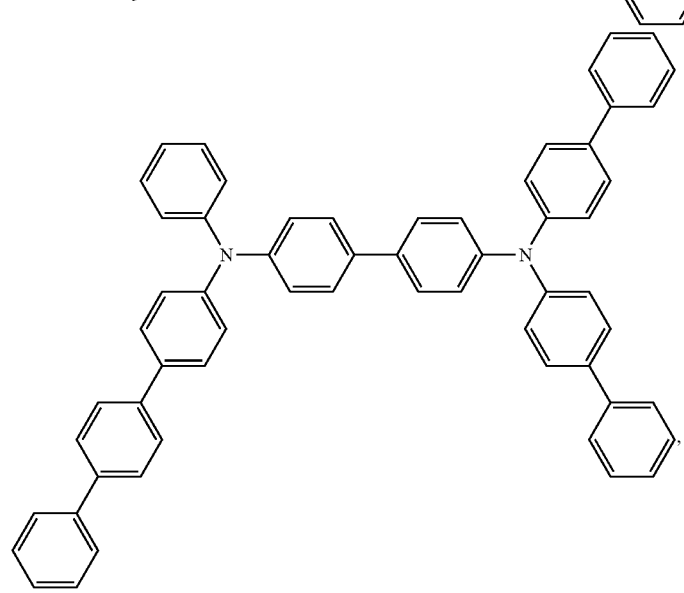
(4-phenyl-N-(4-phenylphenyl)-N-[4-[4-(N-[4-(4-phenyl-phenyl)phenyl]anilino)phenyl]phenyl]aniline
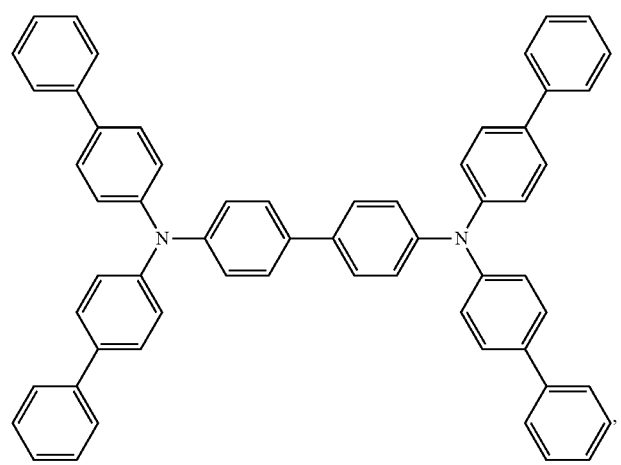
(4-phenyl-N-(4-phenylphenyl)-N-[4-[4-(4-phenyl-N-(4-phenylphenyl)anilino)phenyl]phenyl]aniline)

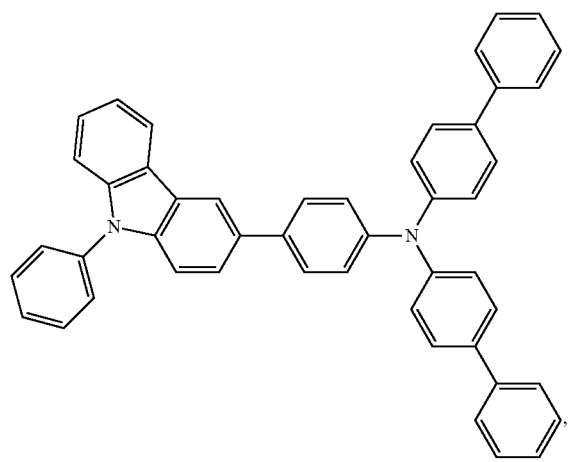

(4-phenyl-N-[4-(9-phenylcarbazol-3-yl)phenyl]-N-(4-phenylphenyl)aniline)

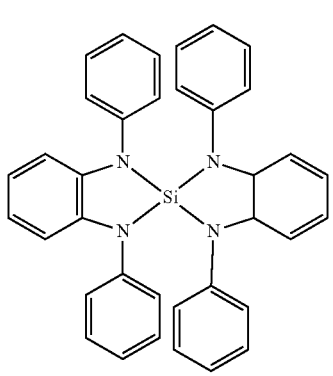

(1,1',3,3'-tetraphenylspiro[1,3,2-benzodiazasilole-2,2'-3a,7a-dihydro-1,3,2-benzodiazasilole])

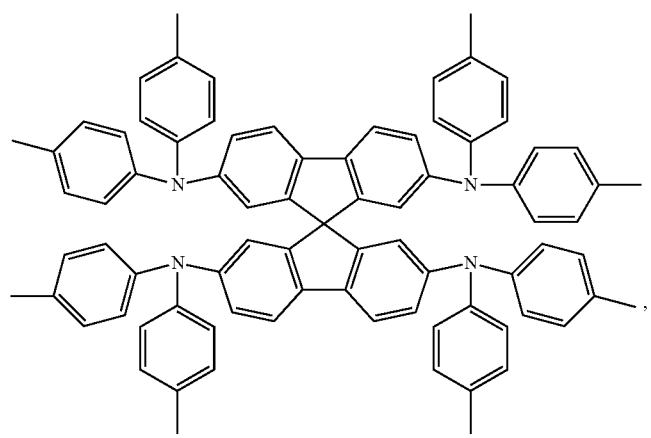

(N2,N2,N2',N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[(di-4-tolylamino)phenyl]-cyclohexane (TAPC), N,N'-bis(4-methylphenyl)-N,N'-bis(4-ethylphenyl)-[1,1'-(3,3'-dimethyl)-biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p-(diethylamino)styryl]5-[p-(diethylamino)phenyl]pyrazoline (PPR or DEASP), 1,2-trans-bis(9H-carbazol9-yl)-cyclobutane (DCZB), N,N,N',N'-tetrakis(4-methylphenyl)-(1,1-biphenyl)-4,4'-diamine (TTB), fluorine compounds such as 2,2',7,7'-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines.

In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS. Preferred examples of a material of the hole injecting layer are a porphyrin compound, an aromatic tertiary amine compound, or a styrylamine compound. Particularly preferable examples include an aromatic tertiary amine compound such as hexacyanohexaazatriphenylene (HAT).

In a preferred embodiment it is possible to use metal carbene complexes as hole transport materials. Suitable carbene complexes are, for example, carbene complexes as described in WO2005/019373A2, WO2006/056418 A2, WO2005/113704, WO2007/115970, WO2007/115981, WO2008/000727 and PCT/EP2014/055520. One example of a suitable carbene complex is Ir(DPBIC)$_3$ with the formula:

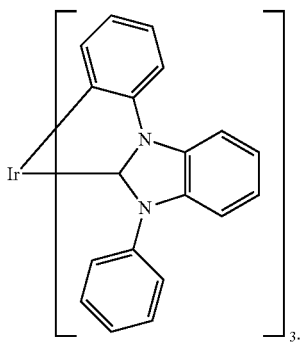

(HTM-1)

Another example of a suitable carbene complex is Ir(ABIC)$_3$ with the Ia:

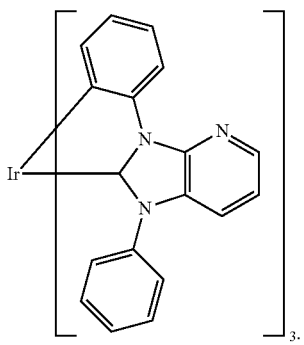

(HTM-2)

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, 2003, 359 (p-doped organic layers); A. G. Werner, F. Li, K. Harada, M. Pfeiffer, T. Fritz, K. Leo, Appl. Phys. Lett., Vol. 82, No. 25, 2003, 4495 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WO_x$, $ReO_3$ and/or $V_2O_5$, preferably $MoO_3$ and/or $ReO_3$, more preferably $MoO_3$, or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho2,6-quinodimethane, 2-fluoro-7,7,8,8-tetracyanoquino-dimethane, 2,5-difluoro-7,7,8,8etracyanoquinodimethane, dicyanomethylene-1,3,4,5,7,8-hexafluoro-6H-naphthalen-2-ylidene)malononitrile ($F_6$-TNAP), Mo(tfd)$_3$ (from Kahn et al., J. Am. Chem. Soc. 2009, 131 (35), 12530-12531), compounds as described in EP1988587, US2008265216, EP2180029, US20100102709, WO2010132236, EP2180029 and quinone compounds as mentioned in EP2401254. Preferred mixtures comprise the aforementioned carbene complexes, such as, for example, the carbene complexes HTM-1 and HTM-2, and $MoO_3$ and/or $ReO_3$, especially $MoO_3$. In a particularly preferred embodiment the hole transport layer comprises from 0.1 to 10 wt % of $MoO_3$ and 90 to 99.9 wt % carbene complex, especially of the carbene complex HTM-1 and HTM-2, wherein the total amount of the $MoO_3$ and the carbene complex is 100 wt %.

Exciton Blocking Layer (d):

Blocking layers may be used to reduce the number of charge carriers (electrons or holes) and/or excitons that leave the emissive layer. An electron/exciton blocking layer (d) may be disposed between the first emitting layer (e) and the hole transport layer (c), to block electrons from emitting layer (e) in the direction of hole transport layer (c). Blocking layers may also be used to block excitons from diffusing out of the emissive layer. Suitable metal complexes for use as electron/exciton blocker material are, for example, carbene complexes as described in WO2005/019373A2, WO2006/056418A2, WO2005/113704, WO2007/115970, WO2007/115981, WO2008/000727 and PCT/EP2014/055520. Explicit reference is made here to the disclosure of the WO applications cited, and these disclosures shall be considered to be incorporated into the content of the present application. One example of a suitable carbene complex is compound HTM-1 and HTM-2.

Emitting Layer (e)

The light-emitting layer (e) comprises at least one emitter material. In principle, it may be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula I can be used as the matrix in the light-emitting layer.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669, WO10086089, US2011/0057559, WO2011/106344, US2011/0233528, WO2012/048266 and WO2012/172482.

Further suitable metal complexes are the commercially available metal complexes tris(2-phenylpyridine)indium (III), indium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)pyridinato-N,C$^{3'}$)(acetylacetonate), tris(2-phenylquinoline)indium(III), iridium(III) bis(2-(4,6-difluorophenyl)pyridinato-N,C$^2$)picolinate, iridium(III) bis(1-phenylisoquinoline)(acetylacetonate), bis(2-phenylquinoline)(acetylacetonato)iridium(III), indium(III) bis(di-benzo[f,h]quinoxaline)(acetylacetonate), iridium(III)

bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetyl-acetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-yl-pyridine)(acetylacetonato)iridium(III).

In addition, the following commercially available materials are suitable: tris(dibenzoylacetonato)mono(phenanthroline)europium(III), tris(dibenzoylmethane)-mono(phenanthroline)europium(III), tris(dibenzoylmethane)mono(5-aminophenanthroline)-europium(III), tris(di-2-naphthoylmethane)mono(phenanthroline)europium(III), tris(4-bromobenzoylmethane)mono(phenanthroline)europium(III), tris(di(biphenyl)methane)-mono(phenanthroline)europium(III), tris(dibenzoylmethane)mono(4,7-diphenyl-phenanthroline)europium(III), tris(dibenzoylmethane)mono(4,7-di-methyl-phenanthroline)europium(III), tris(dibenzoylmethane)mono(4,7-dimethylphenanthrolinedisulfonic acid)europium(III) disodium salt, tris[di(4-(2-(2-ethoxyethoxy)ethoxy)-benzoylmethane)]mono(phenanthroline)europium(III) and tris[di[4-(2-(2-ethoxyethoxy)ethoxy)benzoylmethane]mono(5-aminophenanthroline)europium(III), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)-pyrazolato) dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

Preferred phosphorescence emitters are carbene complexes. Suitable phosphorescent blue emitters are specified in the following publications: WO2006/056418A2, WO2005/113704, WO2007/115970, WO2007/115981, WO2008/000727, WO2009/050281, WO2009/050290, WO2011051404, US2011/057559 WO2011/073149, WO2012/121936A2, US2012/0305894A1, WO2012/170571, WO2012/170461, WO2012/170463, WO2006/121811, WO2007/095118, WO2008/156879, WO2008/156879, WO2010/068876, US2011/0057559, WO2011/106344, US2011/0233528, WO2012/048266, WO2012/172482, PCT/EP2014/064054 and PCT/EP2014/066272.

Preferably, the light emitting layer (e) comprises at least one carbine complex as phosphorescence emitter. Suitable carbine complexes are, for example, compounds of the formula

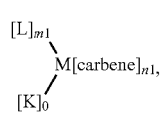

(IX)

which are described in WO 2005/019373 A2, wherein the symbols have the following meanings:

M is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom;

Carbene is a carbene ligand which may be uncharged or monoanionic and monodentate, bidentate or tridentate, with the carbene ligand also being able to be a biscarbene or triscarbene ligand;

L is a monoanionic or dianionic ligand, which may be monodentate or bidentate;

K is an uncharged monodentate or bidentate ligand selected from the group consisting of phosphines; phosphonates and derivatives thereof, arsenates and derivatives thereof; phosphites; CO; pyridines; nitriles and conjugated dienes which form a π complex with $M^1$;

n1 is the number of carbene ligands, where n1 is at least 1 and when n1>1 the carbene ligands in the complex of the formula I can be identical or different;

m1 is the number of ligands L, where m1 can be 0 or ≥1 and when m1>1 the ligands L can be identical or different;

o is the number of ligands K, where o can be 0 or ≥1 and when o>1 the ligands K can be identical or different;

where the sum n1+m1+o is dependent on the oxidation state and coordination number of the metal atom and on the denticity of the ligands carbene, L and K and also on the charge on the ligands, carbene and L, with the proviso that n1 is at least 1.

More preferred are metal-carbene complexes of the general formula

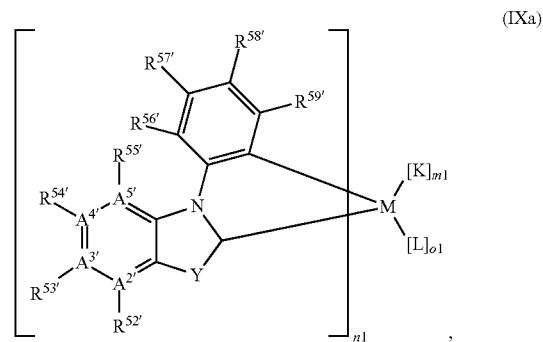

(IXa)

which are described in WO2011/073149, where M is Ir, or Pt, n1 is an integer selected from 1, 2 and 3, Y is $NR^{51'}$, O, S or $C(R^{25'})_2$, $A^{2'}$, $A^{3'}$, $A^{4'}$, and $A^{5'}$ are each independently N or C, where 2 A'=nitrogen atoms and at least one carbon atom is present between two nitrogen atoms in the ring, $R^{51'}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{52'}$, $R^{53'}$, $R^{54'}$ and $R^{55'}$ are each, if $A^{2'}$, $A^{3'}$, $A^{4'}$ and/or $A^{5'}$ is N, a free electron pair, or, if $A^{2'}$, $A^{3'}$, $A^{4'}$ and/or $A^{5'}$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{53'}$ and $R^{54'}$ together with $A^{3'}$ and $A^{4'}$ form an optionally substituted, unsaturated ring optionally interrupted by at least one further heteroatom and having a total of 5 to 18 carbon atoms and/or heteroatoms, $R^{56'}$, $R^{57'}$, $R^{58'}$ and $R^{59'}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{56'}$ and $R^{57'}$, $R^{57'}$ and $R^{58'}$ or $R^{58'}$ and $R^{59'}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if $A^{5'}$ is C, $R^{55'}$ and $R^{56'}$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{25'}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, K is an uncharged mono- or bidentate ligand, L is a mono- or dianionic ligand, preferably monoanionic ligand, which may be mono- or bidentate, m1 is 0, 1 or 2, where, when m1 is 2, the K ligands may be the same or different, o1 is 0, 1 or 2, where, when o1 is 2, the L ligands may be the same or different.

The compound of formula IX is preferably a compound of the formula:

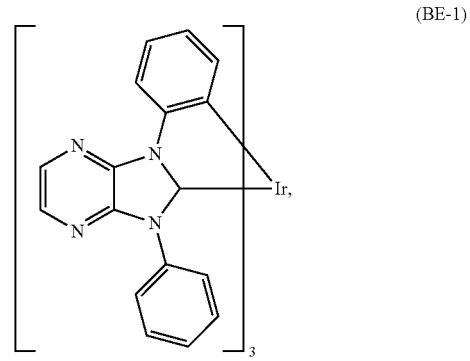
(BE-1)

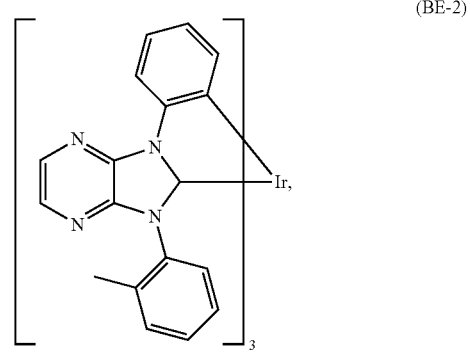
(BE-2)

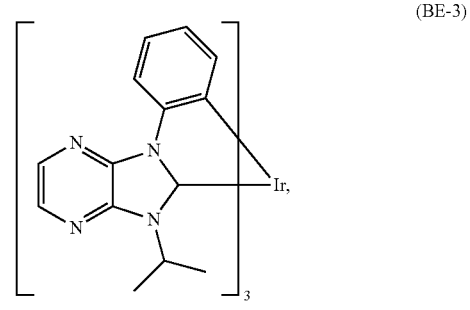
(BE-3)

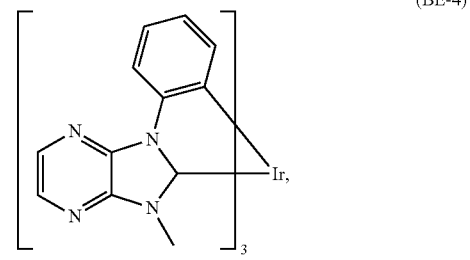
(BE-4)

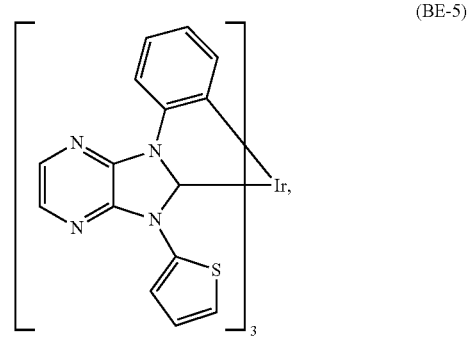
(BE-5)

-continued
(BE-6)
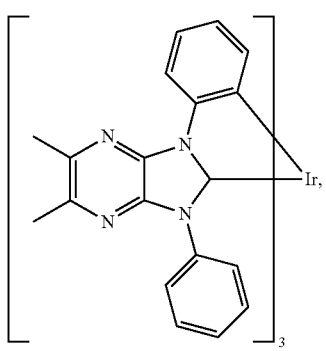
(BE-7)
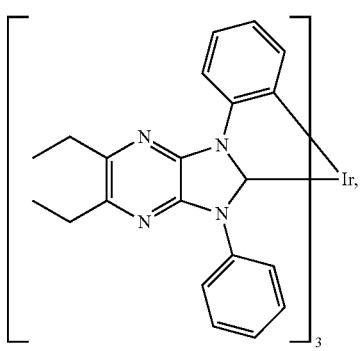
(BE-8)
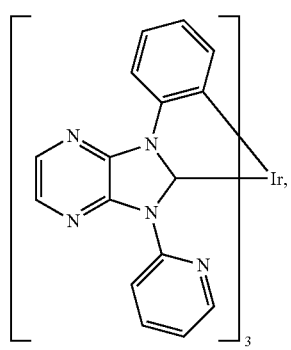
(BE-9)
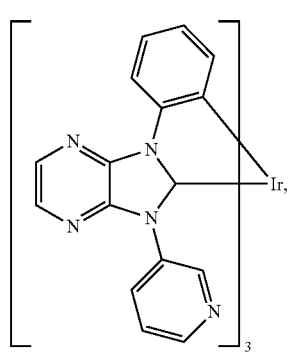
-continued
(BE-10)
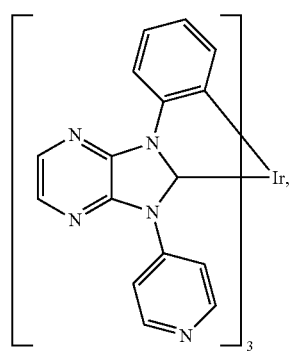
(BE-11)
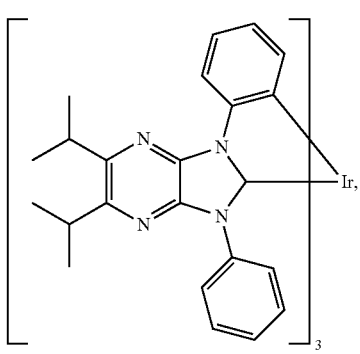
(BE-12)
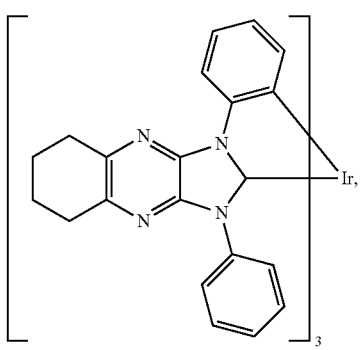
(BE-13)
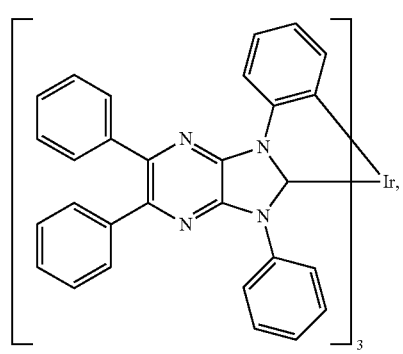

-continued
(BE-14)
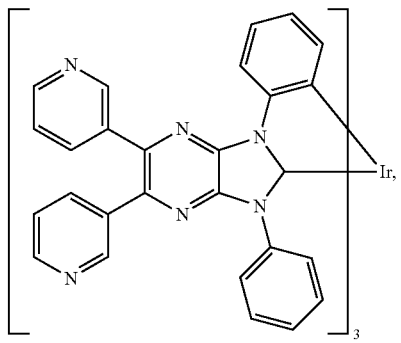
(BE-15)
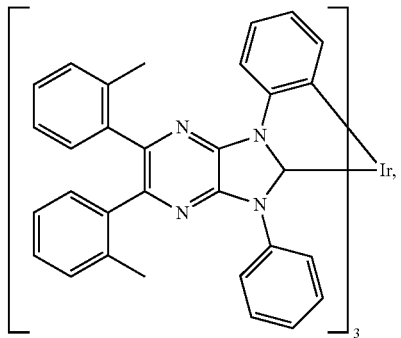
(BE-16)
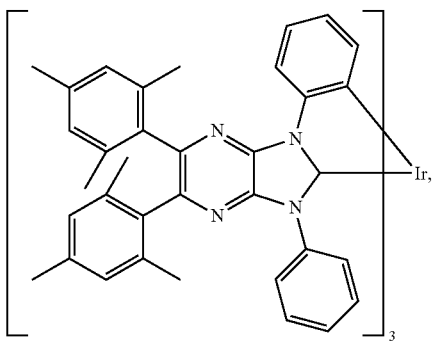
(BE-17)
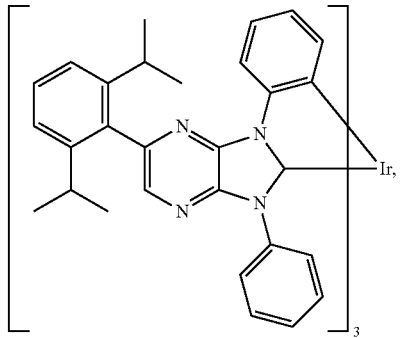
-continued
(B-18)
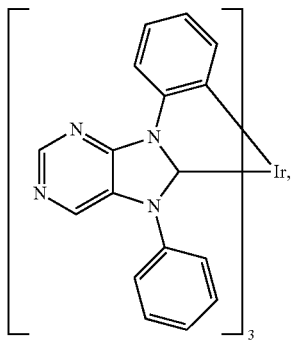
(B-19)
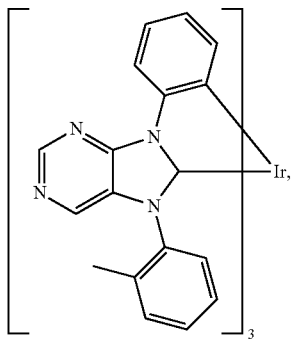
(B-20)
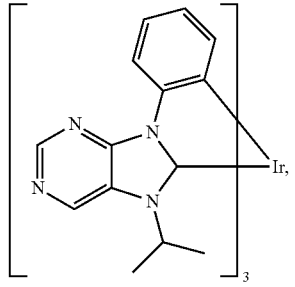
(B-21)
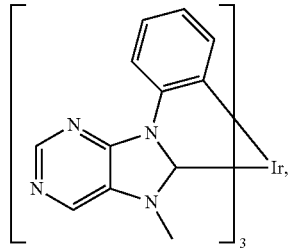
(B-22)
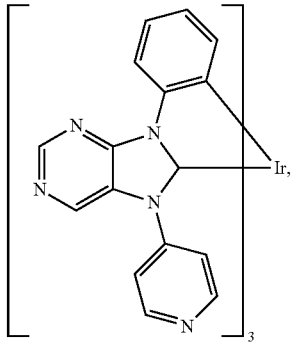

(BE-23)
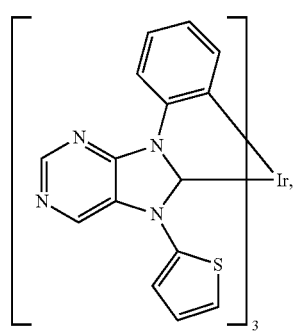
(BE-24)
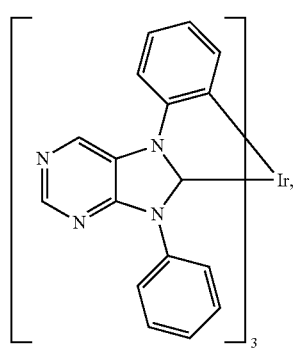
(BE-25)
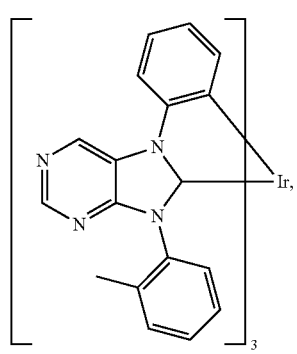
(BE-26)
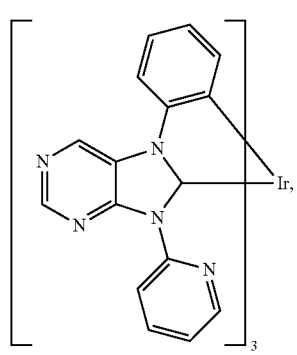
(BE-27)
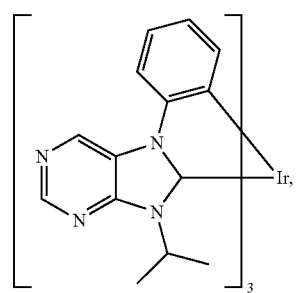
(BE-28)
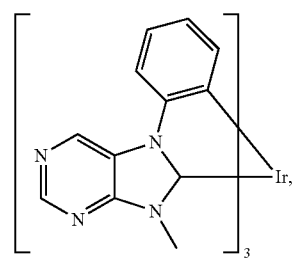
(BE-29)
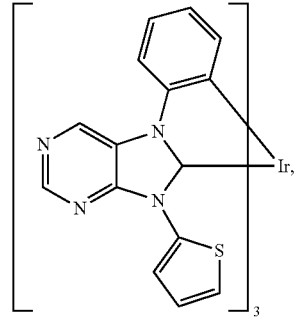
(BE-30)
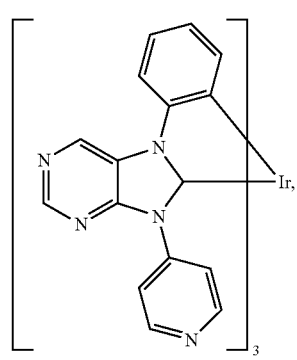
(BE-31)
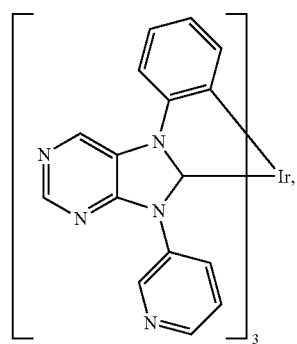

(BE-32)
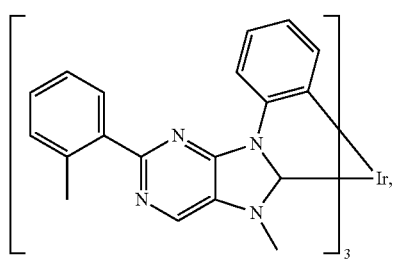
(BE-33)
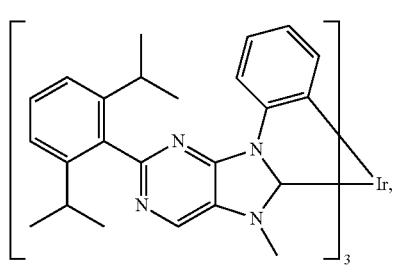
(BE-34)
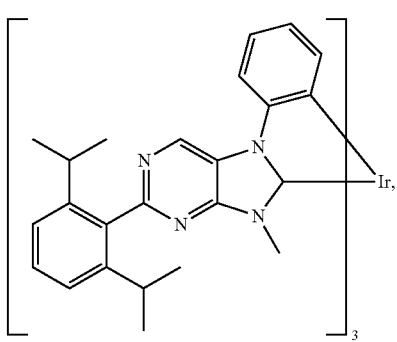
(BE-35)
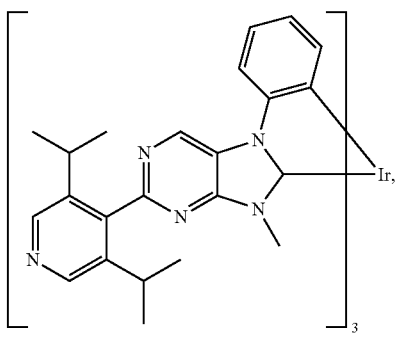
(BE-36)
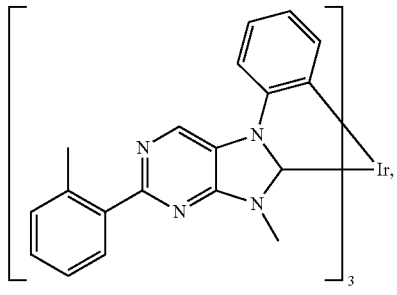
(BE-37)
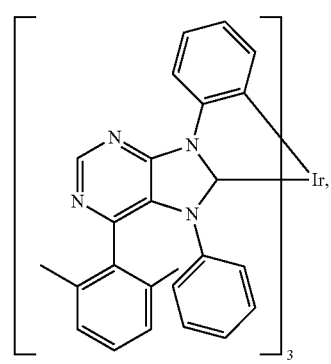
(BE-38)
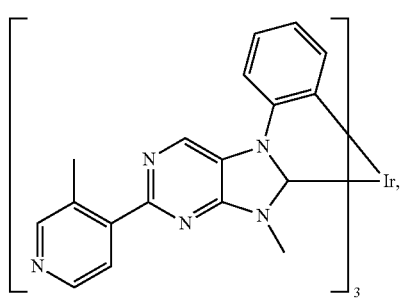
(BE-39)
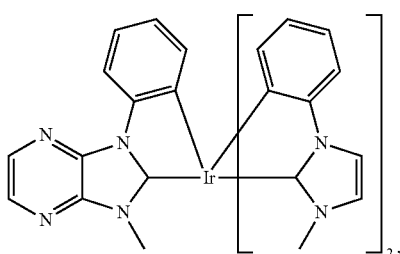
(BE-40)
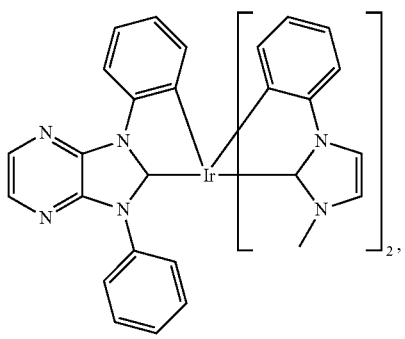
(BE-41)
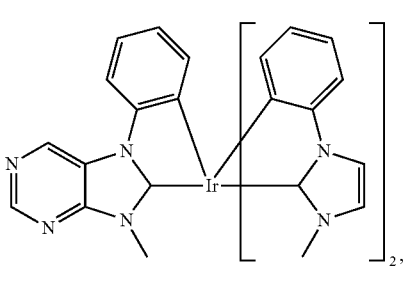

(BE-42)
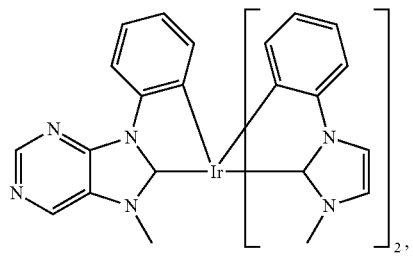
(BE-47)
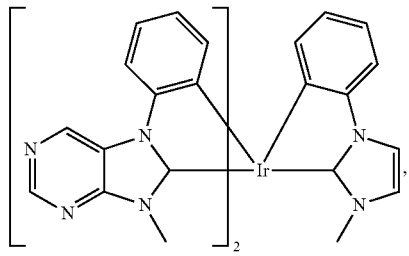
(BE-43)
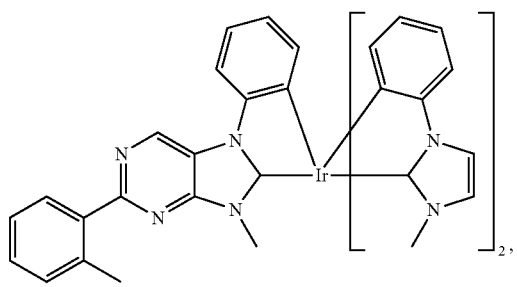
(BE-48)
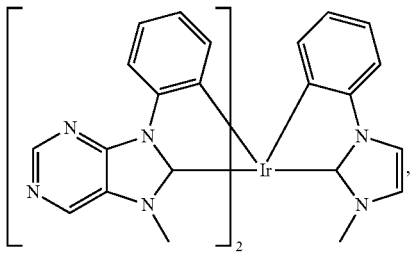
(BE-44)
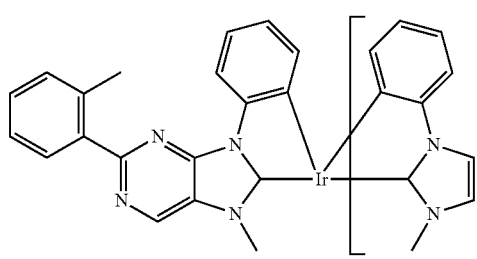
(BE-49)
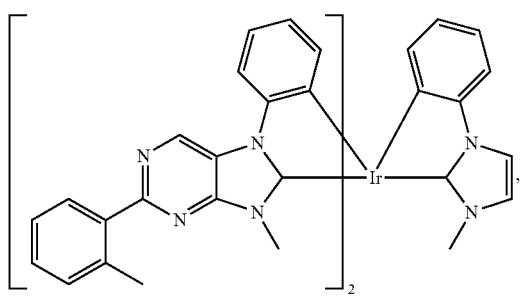
(BE-45)
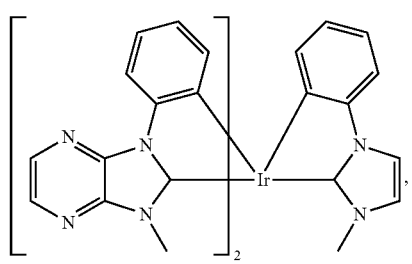
(BE-50)
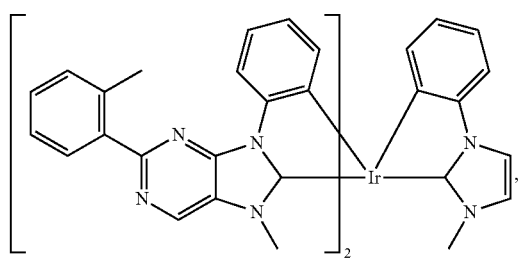
(BE-46)
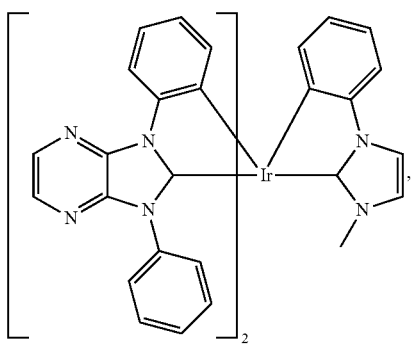
(BE-51)
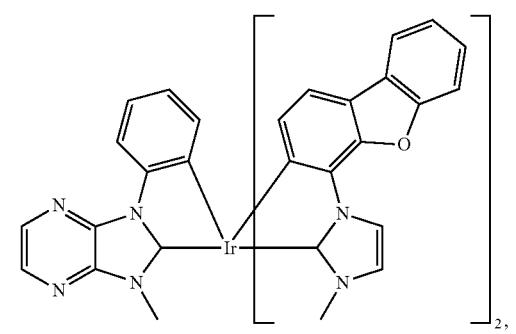

(BE-52)
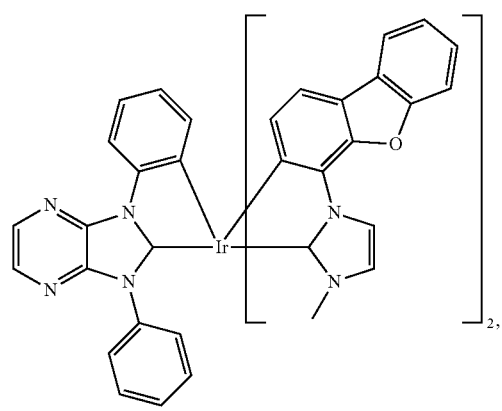
(BE-53)
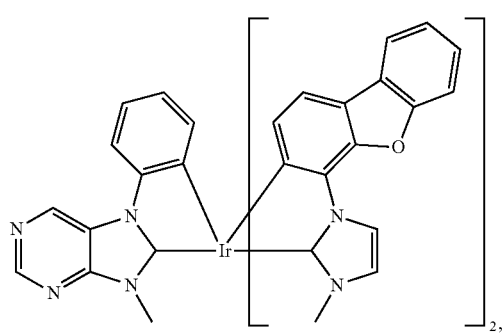
(BE-54)
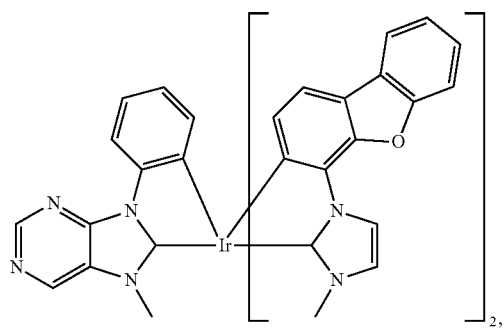
(BE-55)
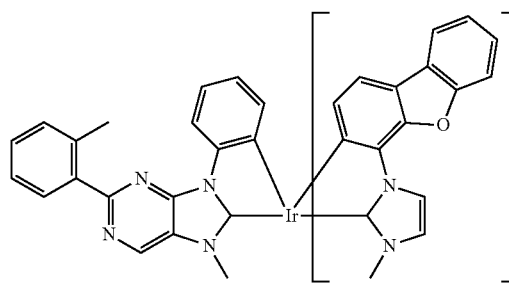
(BE-56)
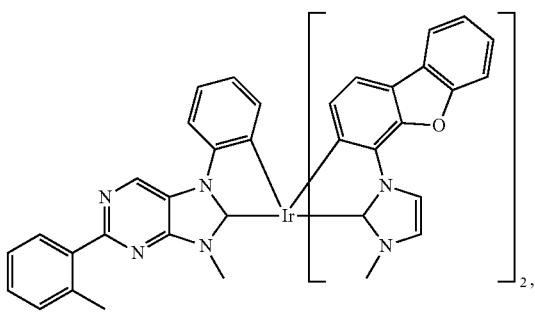
(BE-57)
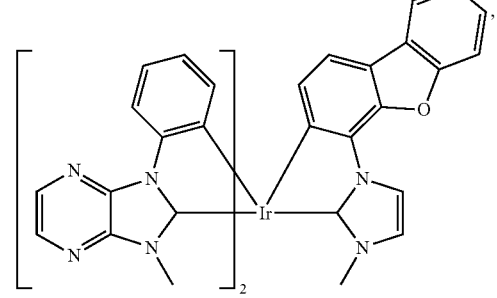
(BE-58)
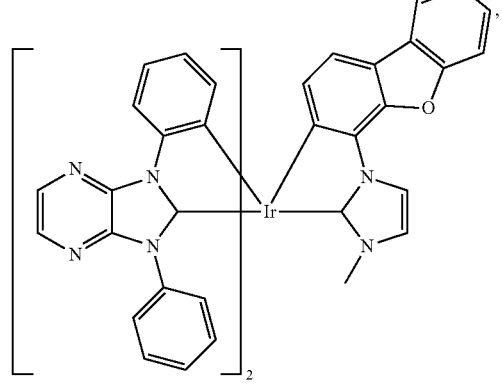
(BE-59)

(BE-60)
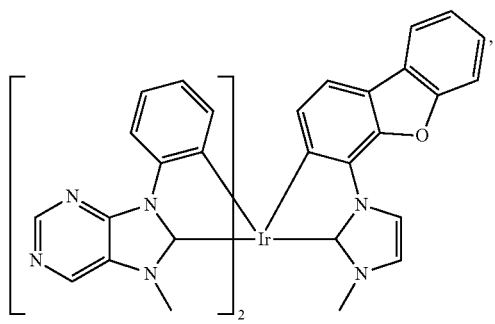
(BE-64)
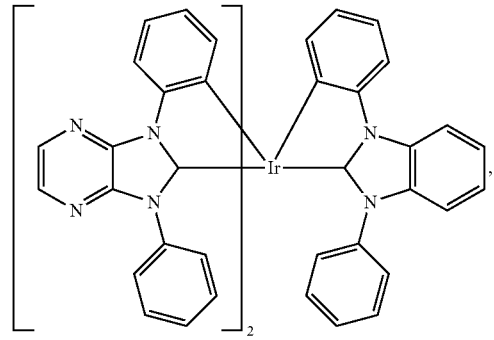
(BE-61)
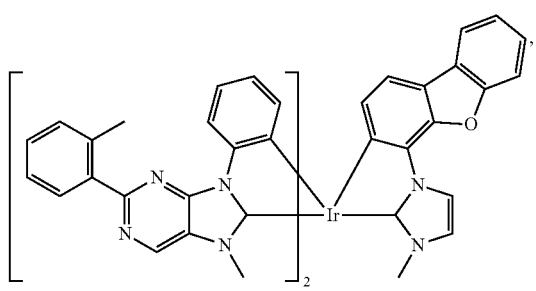
(BE-65)
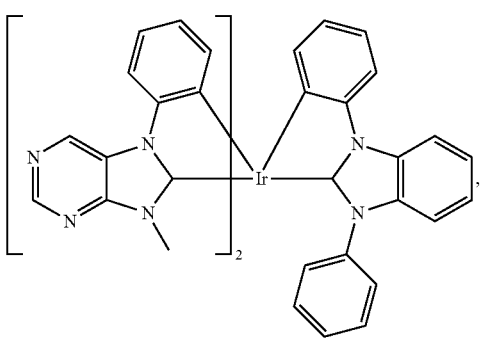
(BE-62)
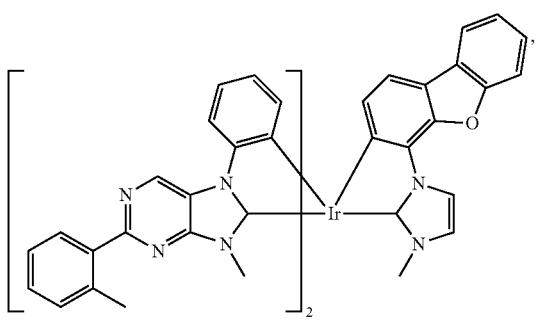
(BE-66)
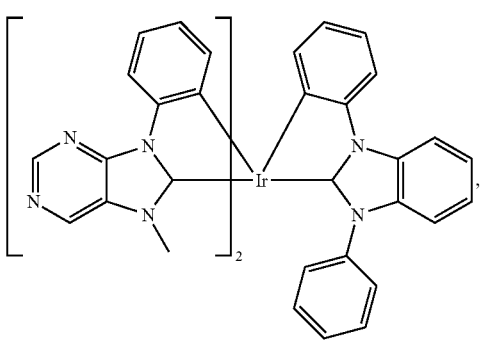
(BE-63)
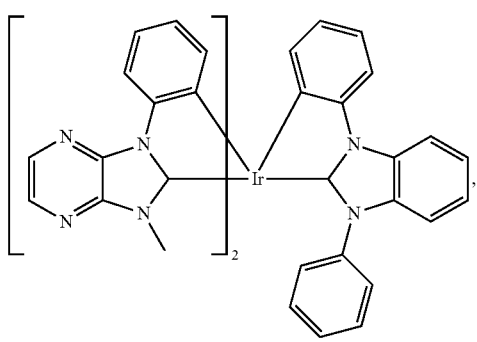
(BE-67)
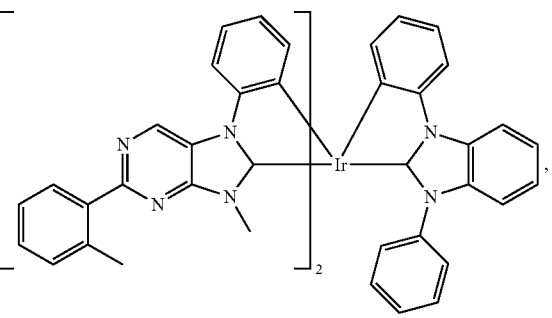

(BE-68)
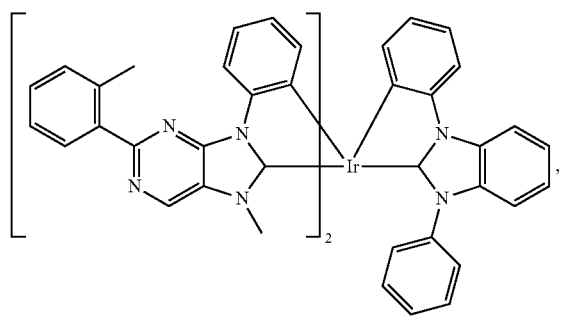
(BE-72)
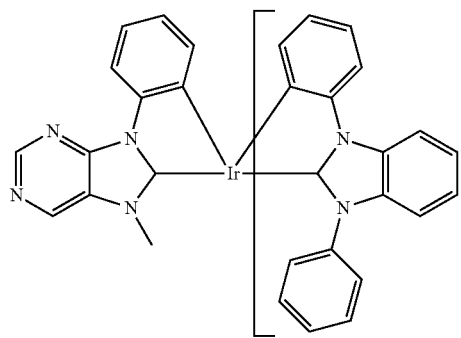
(BE-69)
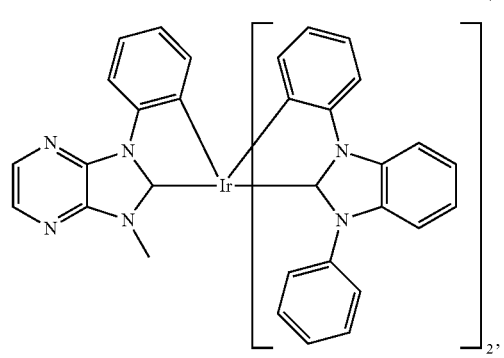
(BE-73)
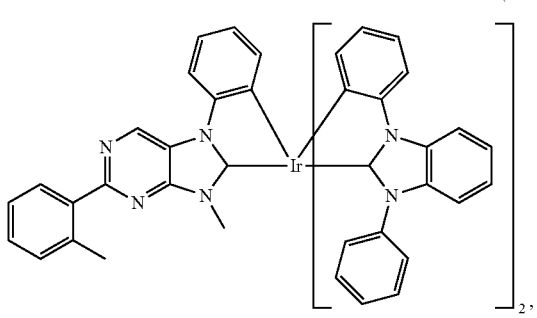
(BE-70)
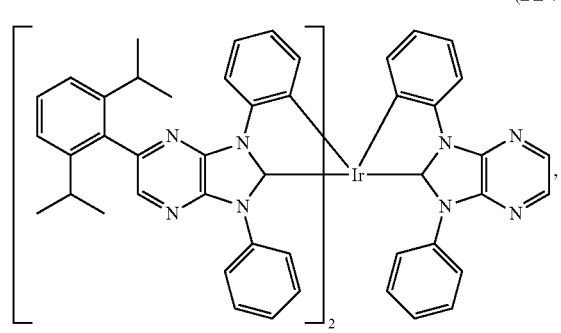
(BE-74)
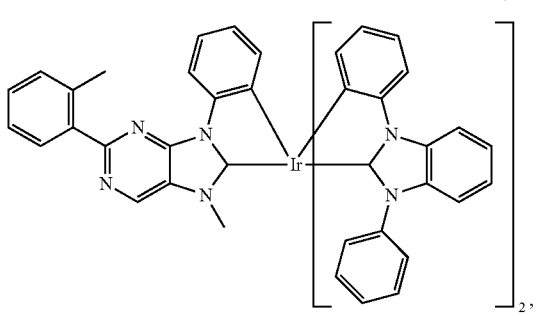
(BE-71)
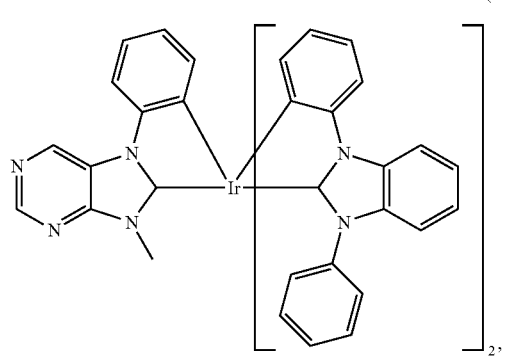
(BE-75)
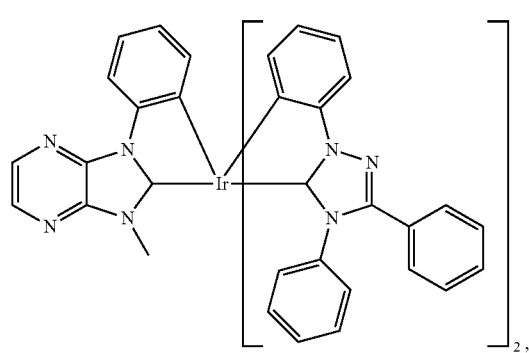

(BE-76)
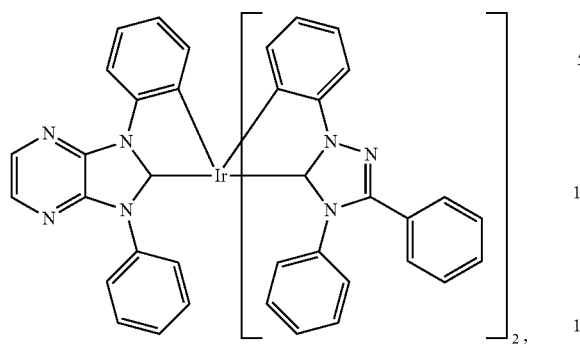
(BE-77)
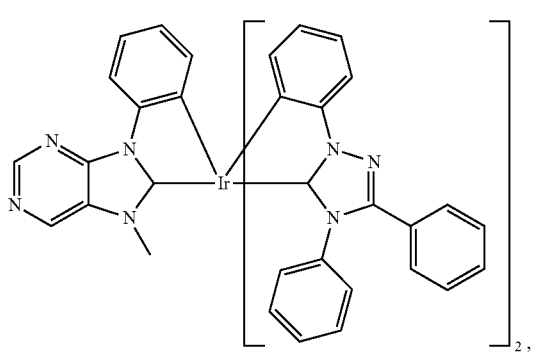
(BE-78)
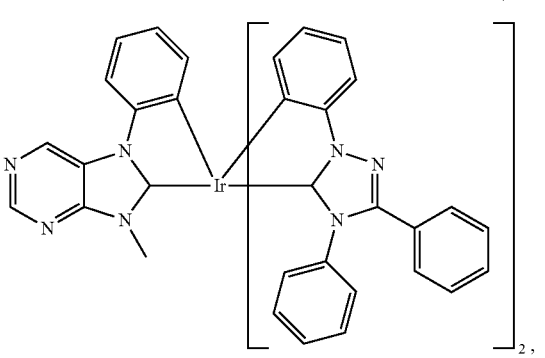
(BE-79)
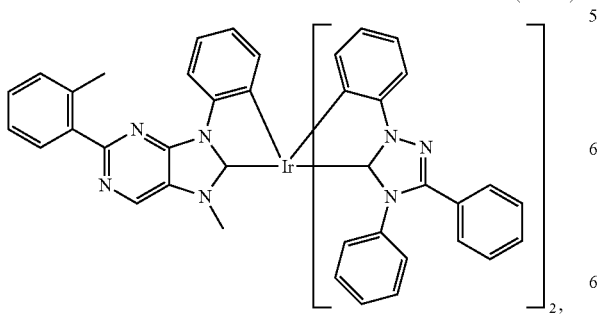
(BE-80)
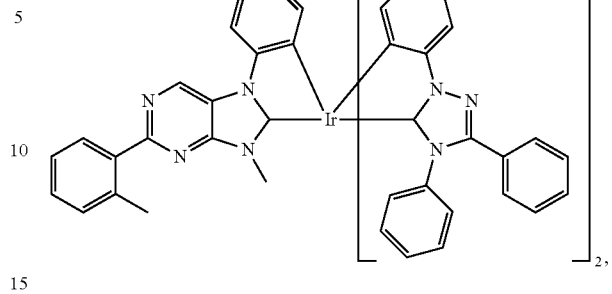
(BE-81)
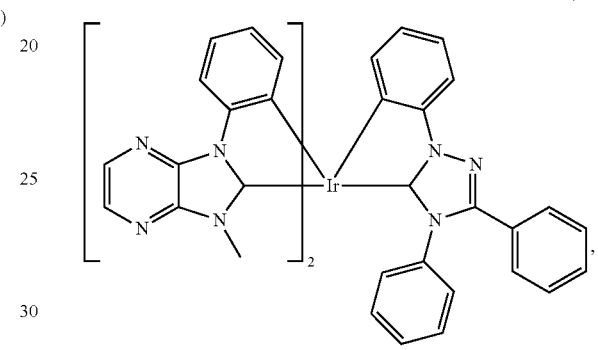
(BE-82)
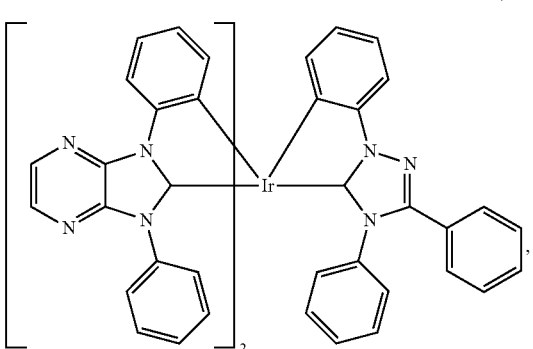
(BE-83)
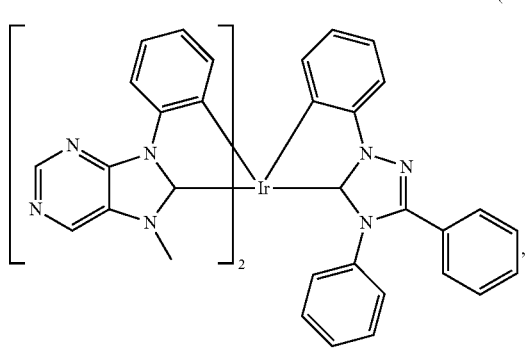

-continued
(BE-84)
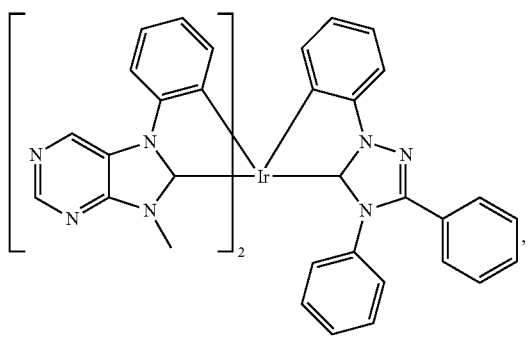
(BE-85)
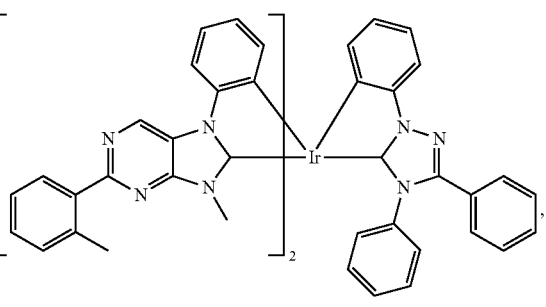
(BE-86)
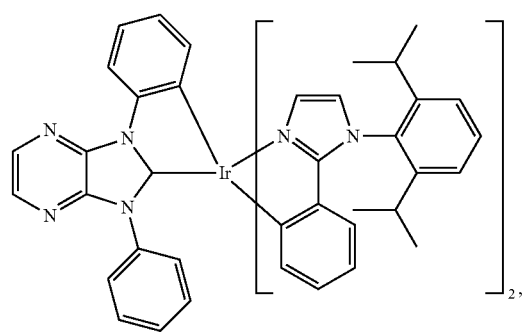
(BE-87)
-continued
(BE-88)
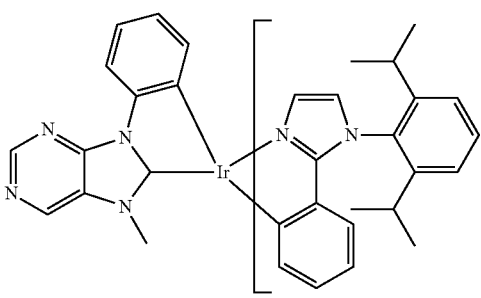
(BE-89)
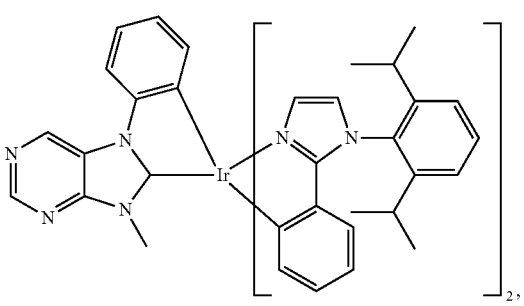
(BE-90)
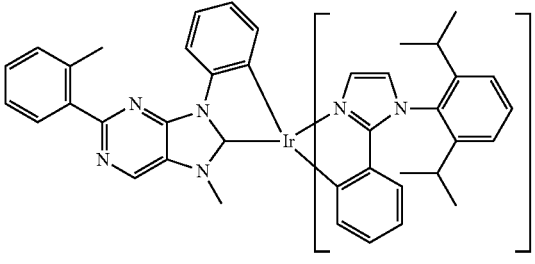
(BE-91)
(BE-92)
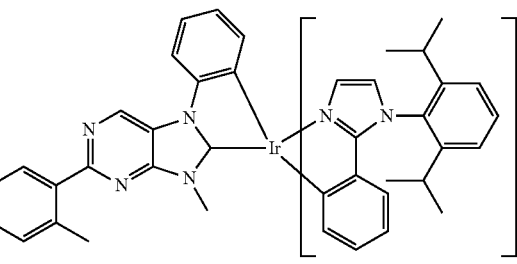

(BE-93)
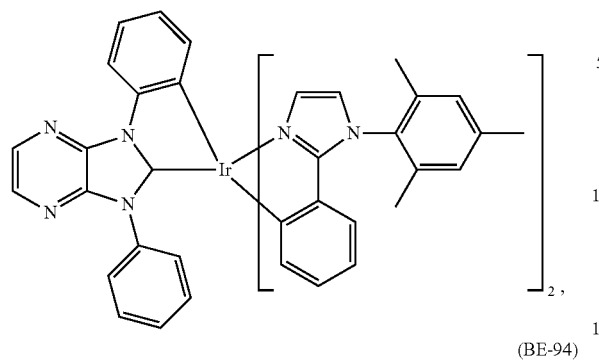
(BE-94)
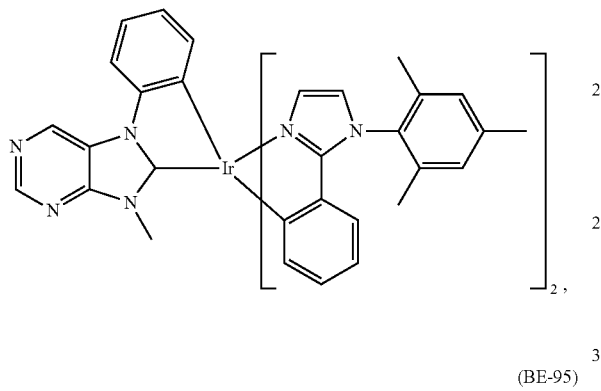
(BE-95)
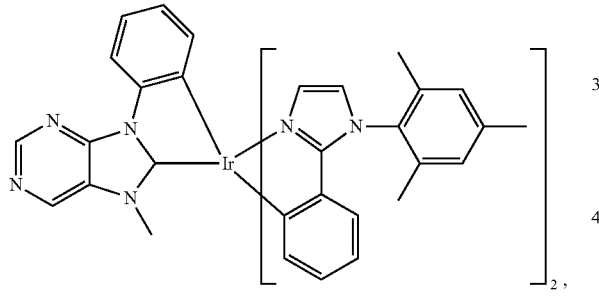
(BE-96)
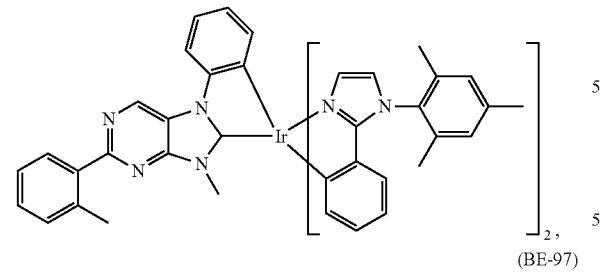
(BE-97)
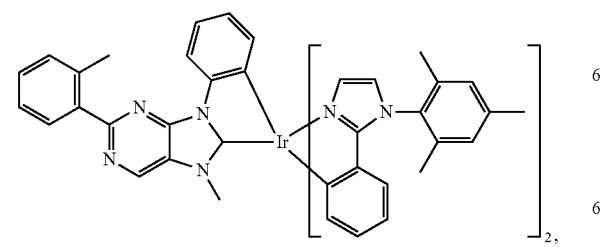
(BE-98)
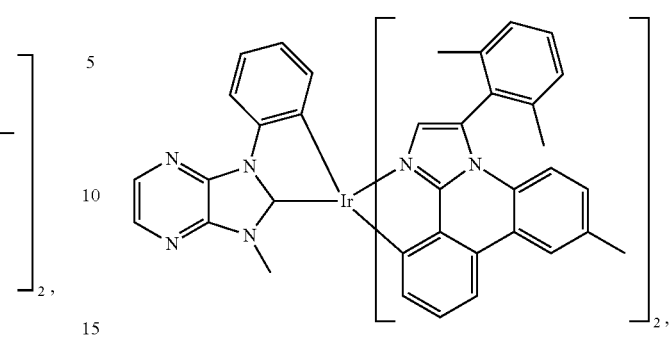
(BE-99)
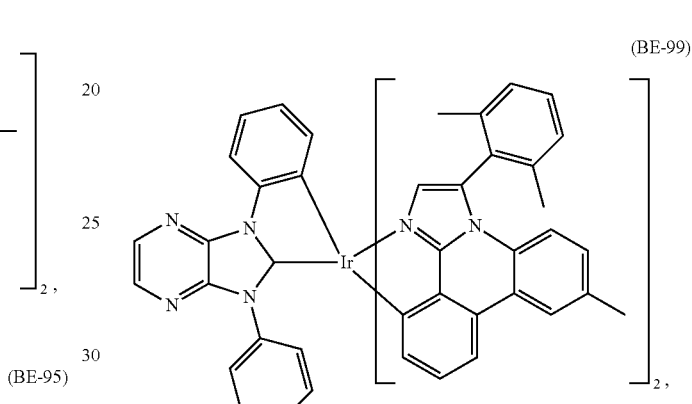
(BE-100)
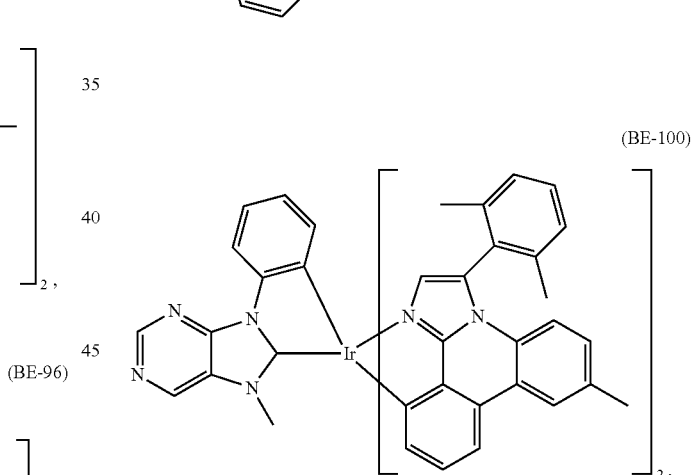
(BE-101)
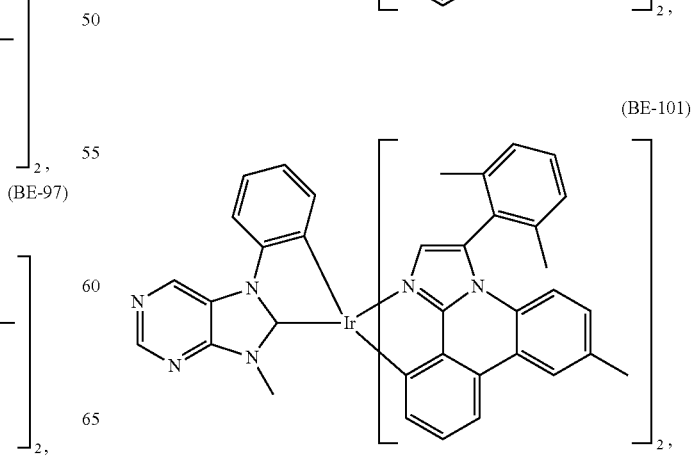

(BE-102)
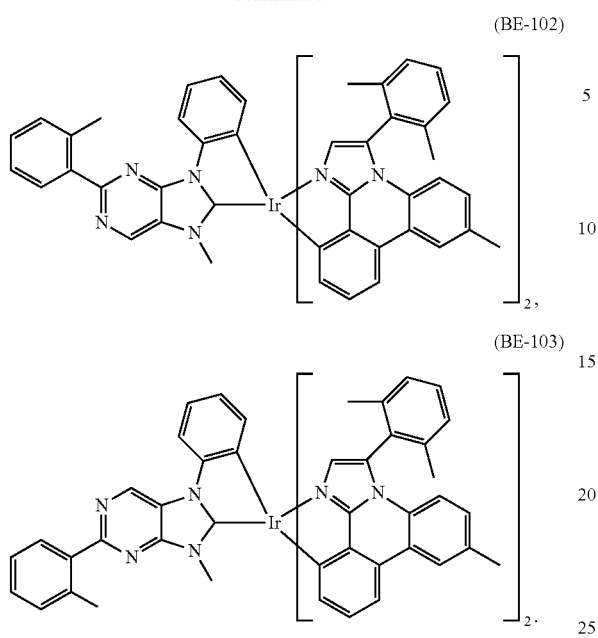
(BE-103)
Further suitable non-carbene emitter materials are mentioned below:
(BE-104)
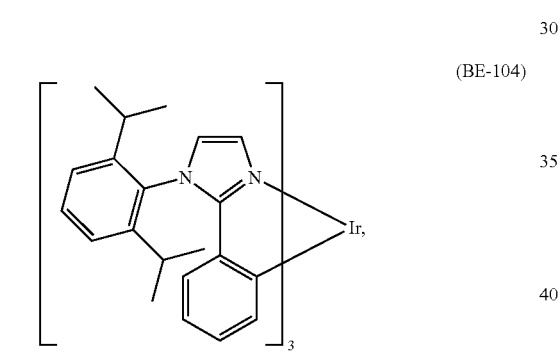
(BE-105)
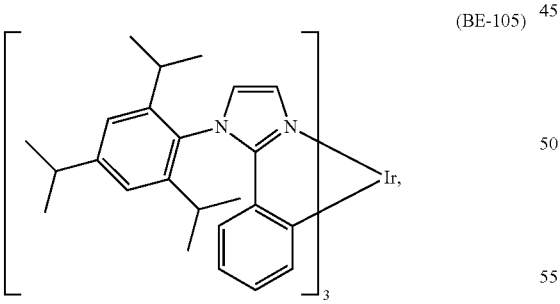
(BE-106)
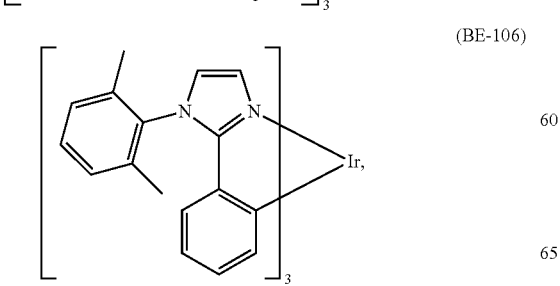
(BE-107)
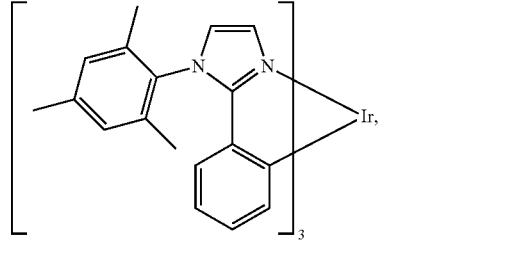
(BE-108)
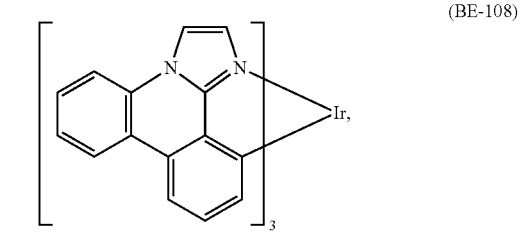
(BE-109)
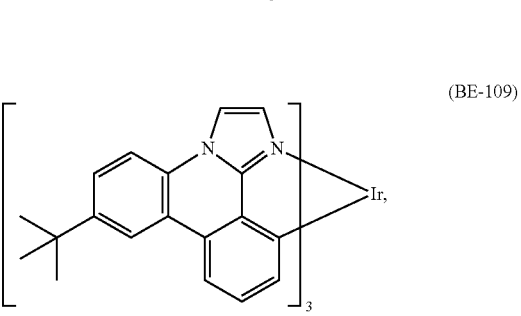
(BE-110)
(BE-111)
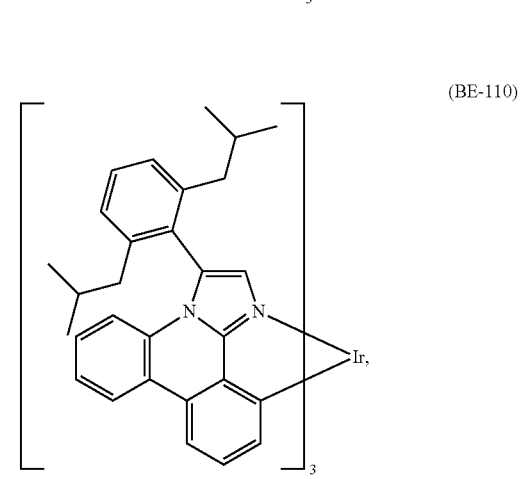

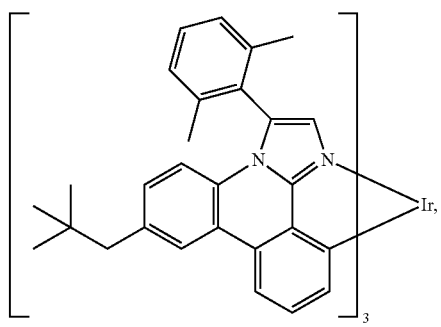 (BE-112)
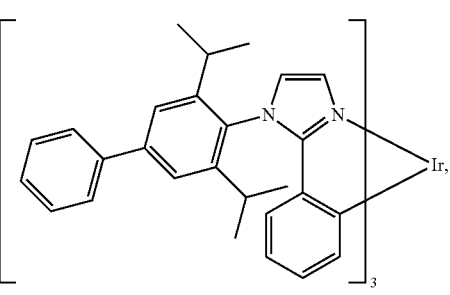 (BE-113)
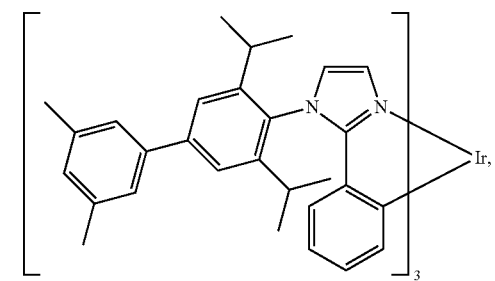 (BE-114)
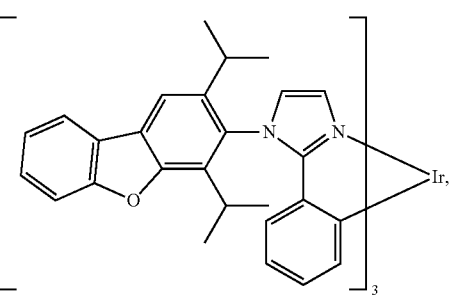 (BE-115)
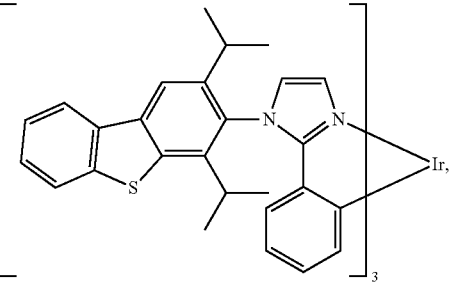 (BE-116)
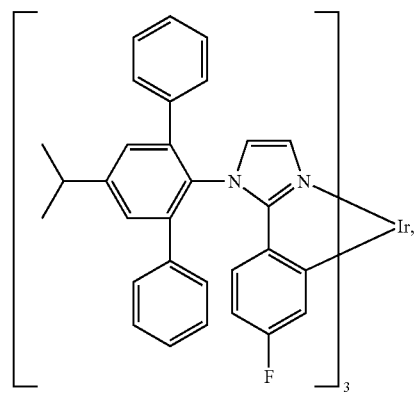 (BE-117)
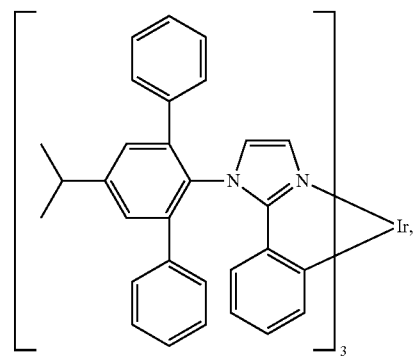 (BE-118)
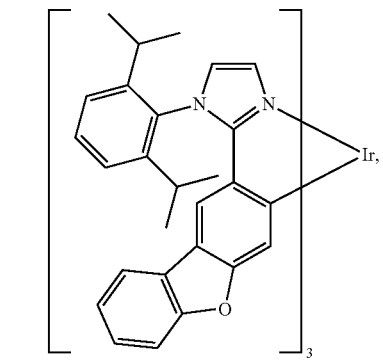 (BE-119)
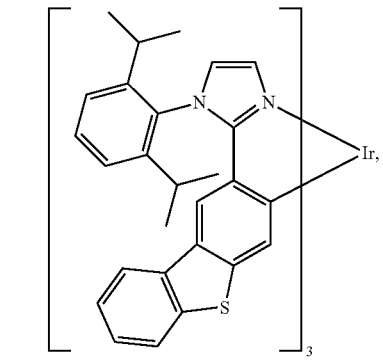 (BE-120)

(BE-121)
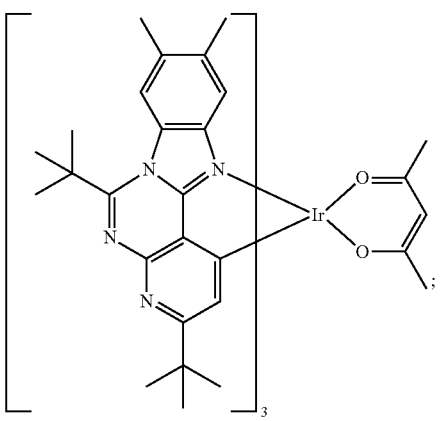

(BE-122)
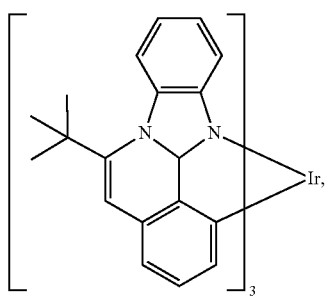

(BE-123)
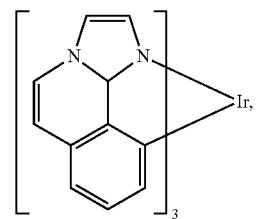

(BE-124)
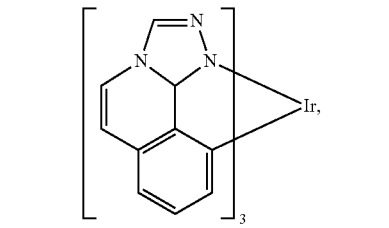

(BE-125)
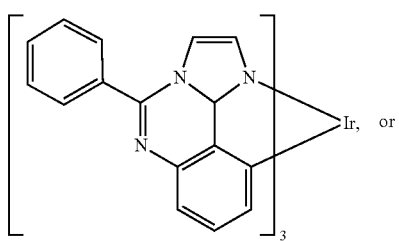

(BE-126)
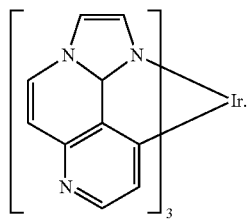

The compound of formula IX is more preferably a compound (BE-1), (BE-2), (BE-7), (BE-12), (BE-16), (BE-64), or (BE-70). The most preferred phosphorescent blue emitters are compounds (BE-1) and (BE-12).

The homoleptic metal-carbene complexes may be present in the form of facial or meridional isomers, preference being given to the facial isomers.

Suitable carbene complexes of formula (IX) and their preparation process are, for example, described in WO2011/073149.

The compounds of the present invention can also be used as host for phosphorescent green emitters. Suitable phosphorescent green emitters are, for example, specified in the following publications: WO2006014599, WO20080220265, WO2009073245, WO2010027583, WO2010028151, US20110227049, WO2011090535, WO2012/08881, WO20100056669, WO20100118029, WO20100244004, WO2011109042, WO2012166608, US20120292600, EP2551933A1; US6687266, US20070190359, US20070190359, US20060008670; WO2006098460, US20110210316, WO2012053627; US6921915, US20090039776; JP2007123392 and European patent application no. 14180422.9.

Examples of suitable phosphorescent green emitters are shown below:

(GE-1)
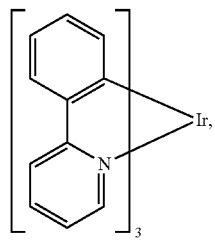

(GE-2)
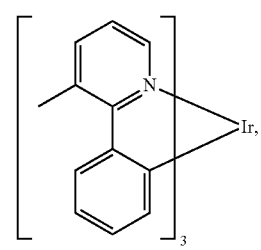

(GE-3)
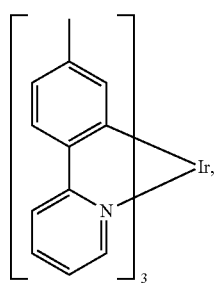
(GE-4)
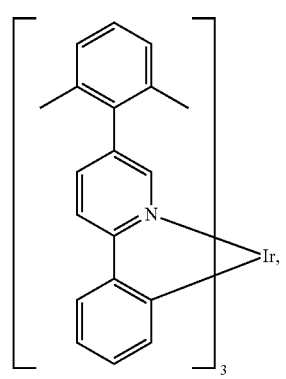
(GE-5)
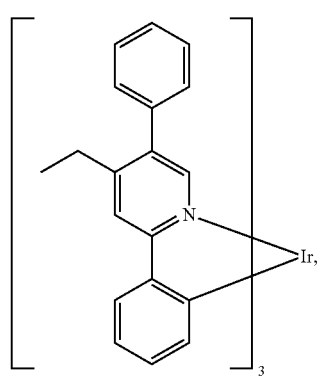
(GE-6)
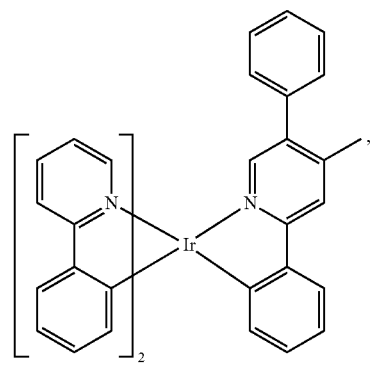
(GE-7)
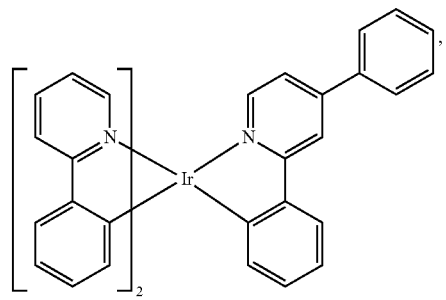
(GE-8)
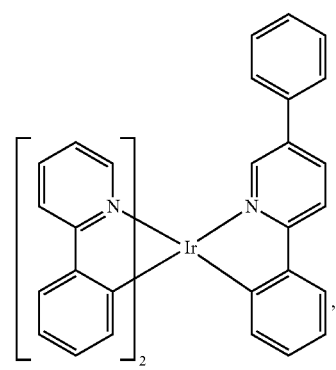
(GE-9)
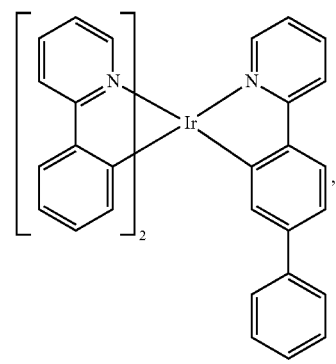
(GE-10)
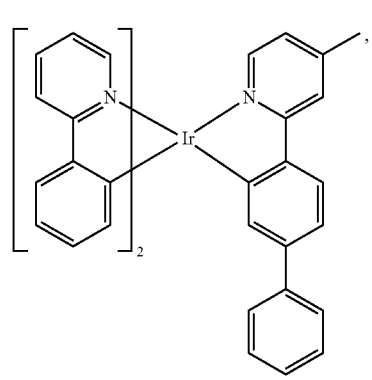

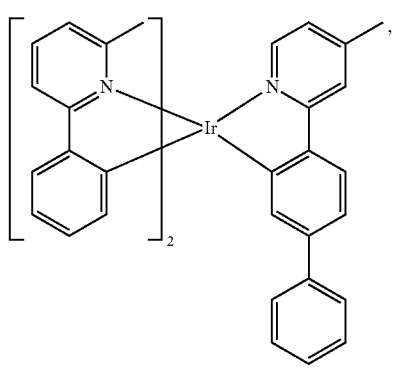
(GE-11)
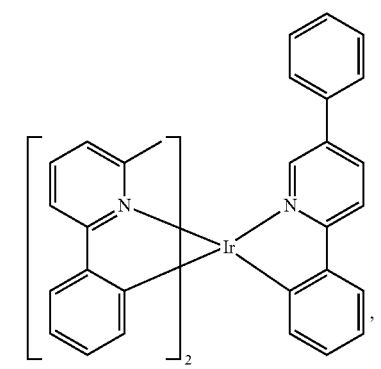
(GE-12)
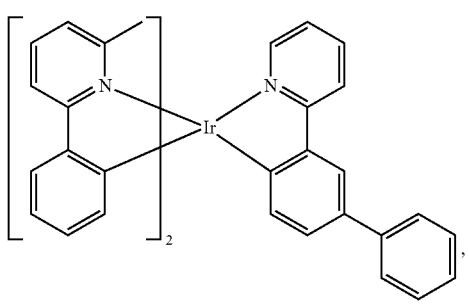
(GE-13)
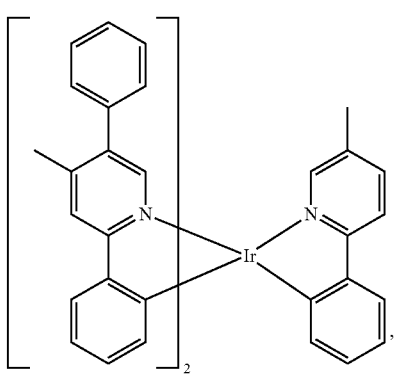
(GE-14)
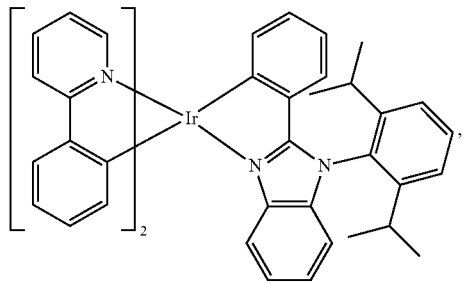
(GE-15)
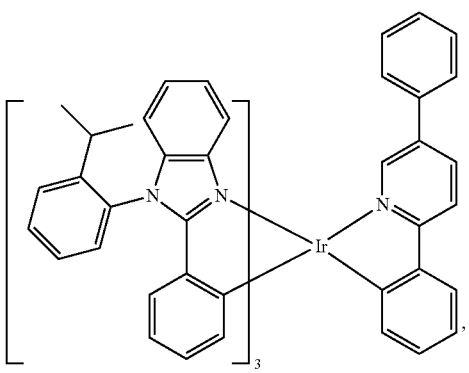
(GE-16)
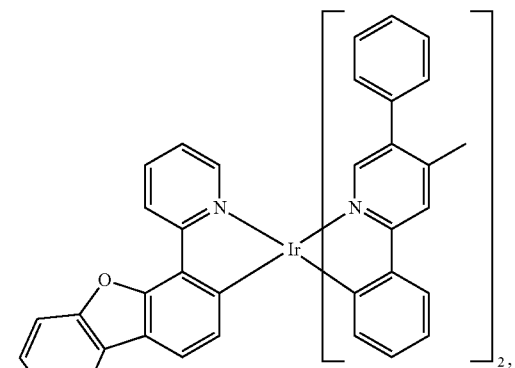
(GE-17)
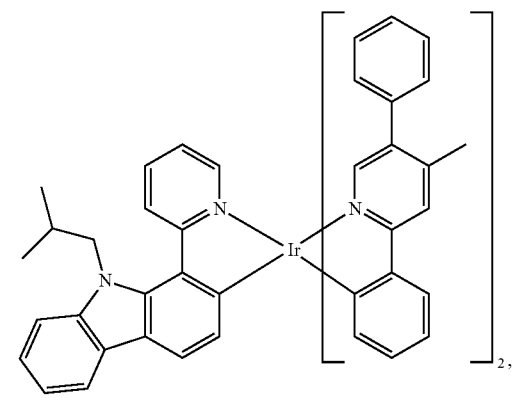
(GE-18)

(GE-19)
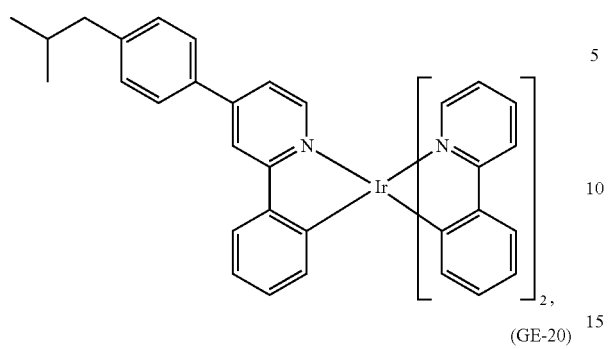
(GE-20)
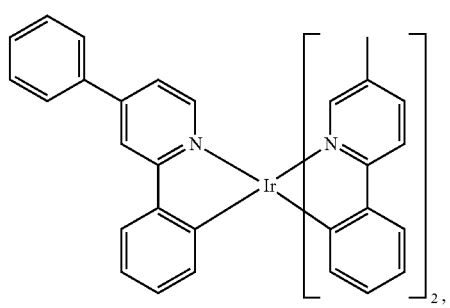
(GE-21)
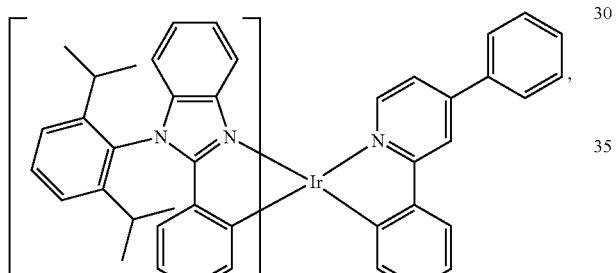
(GE-22)
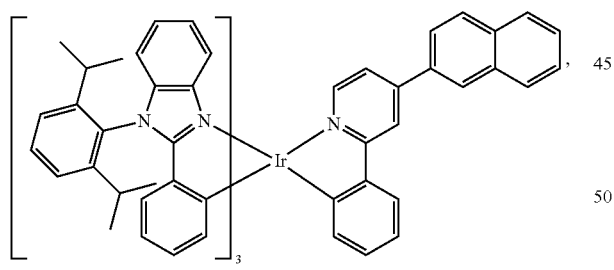
(GE-23)
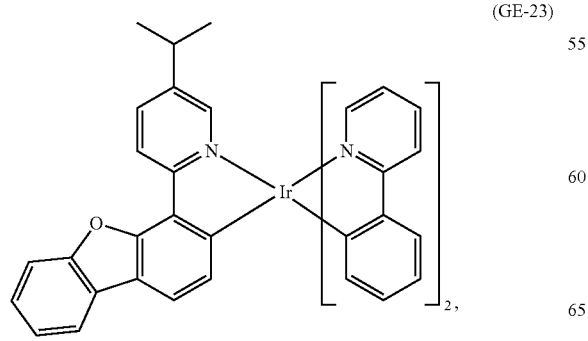
(GE-24)
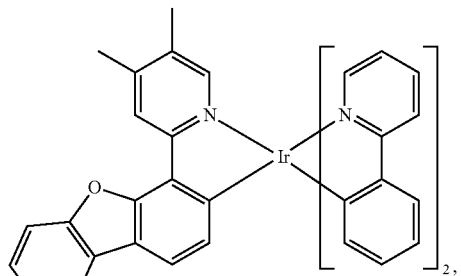
(GE-25)
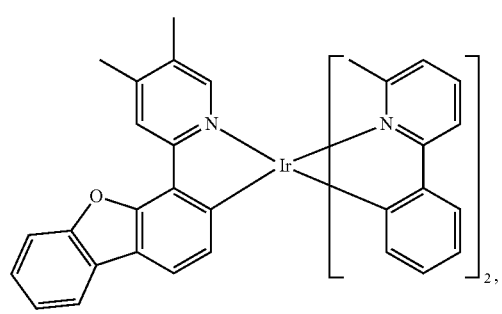
(GE-26)
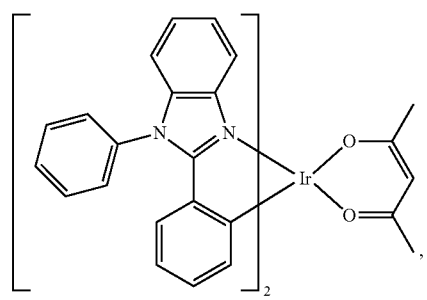
(GE-27)
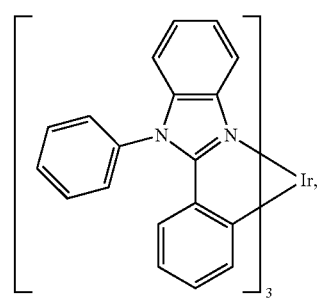
(GE-28)
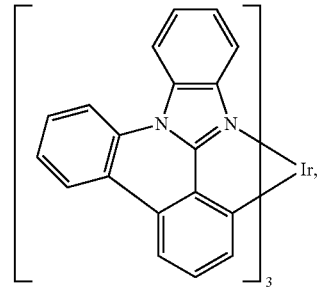

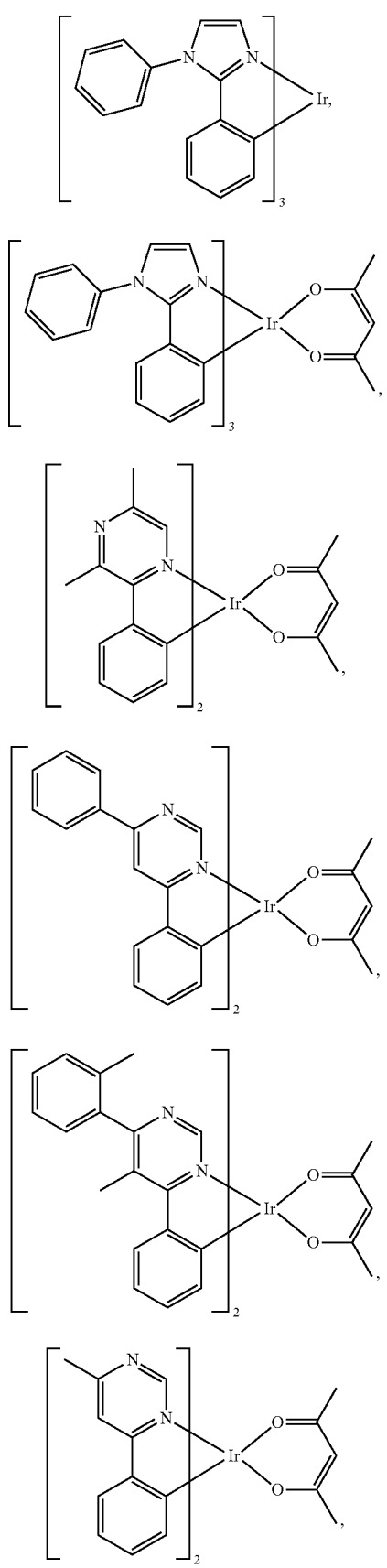
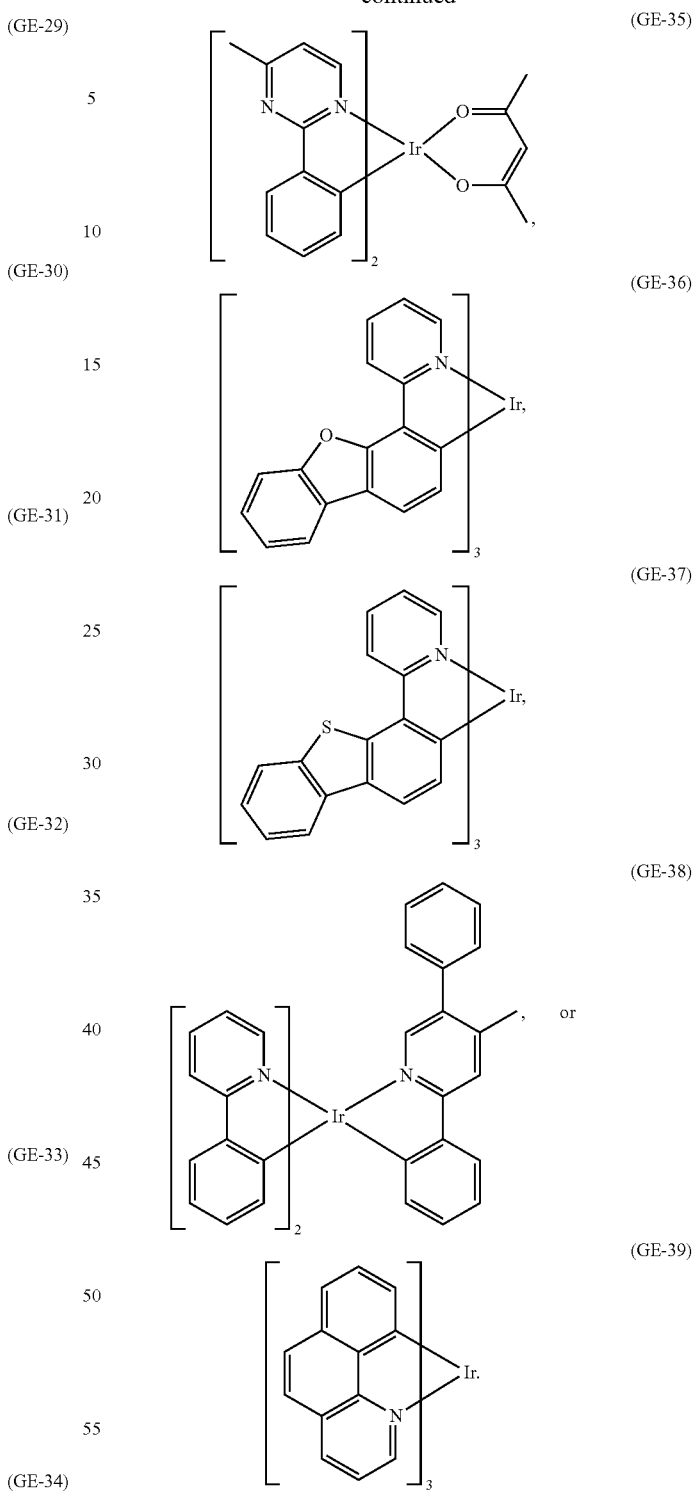

Host (Matrix) Materials

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA.

In another preferred embodiment of the present invention, at least one compound of formula I, especially a compound of formula (Ia), very especially a compound of formula (Ia-1), or (Ia-2), is used as matrix material. Examples of preferred compounds of formula I are (A-1), (A-2), (A-3), (A-5), (A-6), (A-7), (A-9), (A-10), (B-1), (B-2), (B-4), (B-6), (B-7), (B-11), (B-17), (B-18), (B-19), (B-20), (B-23), (B-24), (B-25), (B-28), (B-29), (B-30), (B-32), (B-33), (B-34), (B-35), (B-36), (B-38), (B-45), (B-46), (B-48), (B-49), (B-50), (B-51), (B-53), (B-55), (B-64), (B-65), (B-69), (B-70), (B-71) and (B-72) shown above. Compounds (A-2), (A-5), (A-7), (A-9), (A-10), (B-1), (B-2), (B-6), (B-7), (B-17), (B-18), (B-19), (B-23), (B-25), (B-28), (B-29), (B-30), (B-32), (B-49), (B-50), (B-51) and (B-53) are particularly preferred.

In a preferred embodiment, the light-emitting layer is formed from 2 to 40% by weight, preferably 5 to 35% by weight, of at least one of the aforementioned emitter materials and 60 to 98% by weight, preferably 75 to 95% by weight, of at least one of the aforementioned matrix materials—in one embodiment at least one compound of the formula I—where the sum total of the emitter material and of the matrix material adds up to 100% by weight.

In particularly preferred embodiment, the light-emitting layer comprises a compound of formula I, such as, for example,

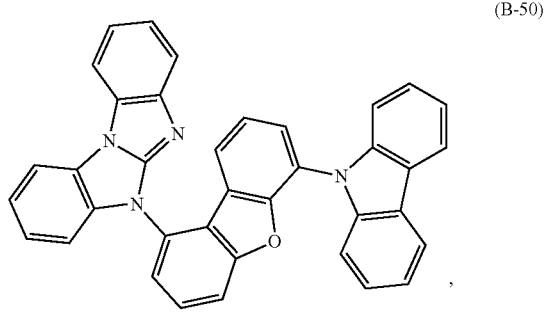 [SMILES: c1ccc2c(c1)nc1n(-c3cccc4oc5c(-n6c7ccccc7c7ccccc76)cccc5c34)c3ccccc3n21]

(B-50)

and two carbene complexes, preferably BE-1 and HTM-1, or HTM-2. In said embodiment, the light-emitting layer is formed from 2 to 40% by weight, preferably 5 to 35% by weight, of BE-1 and 60 to 98% by weight, preferably 65 to 95% by weight, of a compound of the formula I and HTM-1, or HTM-2, where the sum total of the carbene complexes and of the compound of formula I adds up to 100% by weight.

Suitable metal complexes for use together with the compounds of the formula I as matrix material in OLEDs are, for example, also carbene complexes as described in WO 2005/019373 A2, WO 2006/056418 A2, WO 2005/113704, WO 2007/115970, WO 2007/115981 and WO 2008/000727.

Further suitable host materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co)polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446, WO06128800, WO2012014621, WO2012105310, WO2012/130709 and European patent applications EP12175635.7 and EP12185230.5. and EP12191408.9 (in particular page 25 to 29 of EP12191408.9).

The above-mentioned small molecules are more preferred than the above-mentioned (co)polymers of the small molecules.

Further suitable second host materials, are described in WO2011137072 (for example,

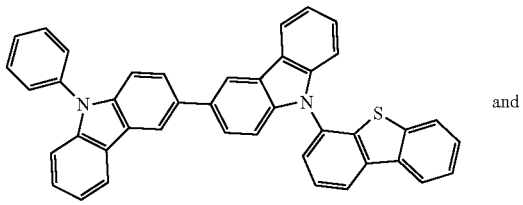

and

-continued

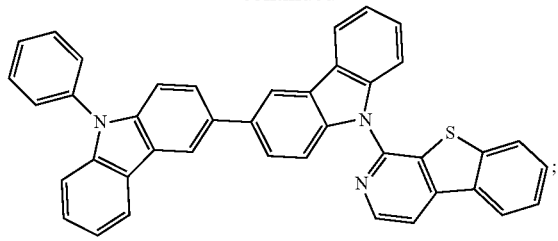

best results are achieved if said compounds are combined with

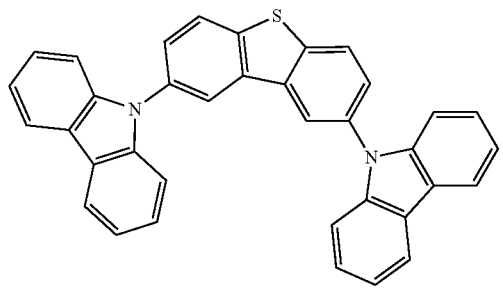

WO2012048266 (for example,

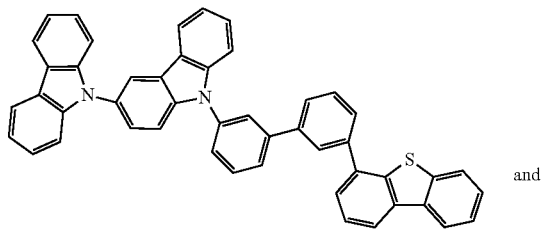

and

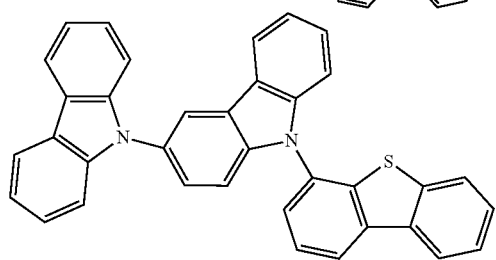

);

WO2012162325 (for example,

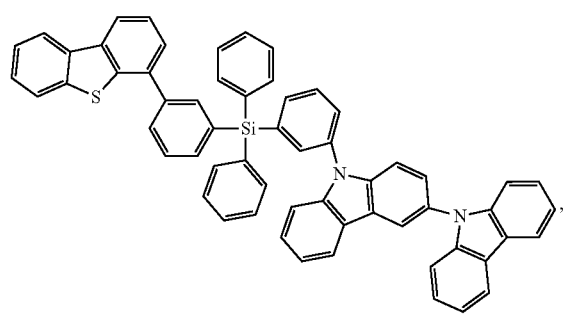

-continued

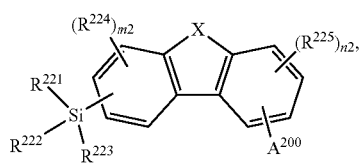

and and EP2551932 (for example,

).

In a particularly preferred embodiment, one or more compounds of the general formula (X) specified hereinafter are used as second host material.

(X)

wherein
X is NR, S, O or PR;
R is aryl, heteroaryl, alkyl, cycloalkyl, or heterocycloalkyl;

$A^{200}$ is $-NR^{206}R^{207}$, $-P(O)R^{208}R^{209}$, $-PR^{210}R^{211}$, $-S(O)_2R^{212}$, $-S(O)R^{213}$, $-SR^{214}$, or $-OR^{215}$;

$R^{221}$, $R^{222}$ and $R^{223}$ are independently of each other aryl, heteroaryl, alkyl, cycloalkyl, or heterocycloalkyl, wherein at least on of the groups $R^{221}$, $R^{222}$, or $R^{223}$ is aryl, or heteroaryl;

$R^{224}$ and $R^{225}$ are independently of each other alkyl, cycloalkyl, heterocycloalkyl, aryl, heteroaryl, a group $A^{200}$, or a group having donor, or acceptor characteristics;

n2 and m2 are independently of each other 0, 1, 2, or 3;

$R^{206}$ and $R^{207}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and $R^{208}$, $R^{209}$, $R^{210}$, $R^{211}$, $R^{212}$, $R^{213}$, $R^{214}$ and $R^{215}$ are independently of each other aryl, heteroaryl, alkyl, cycloalkyl, or heterocycloalkyl. Compounds of formula X, such as, for example,

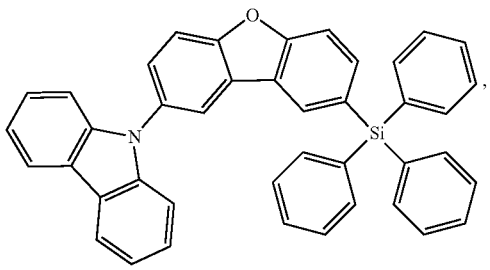
(SH-4)

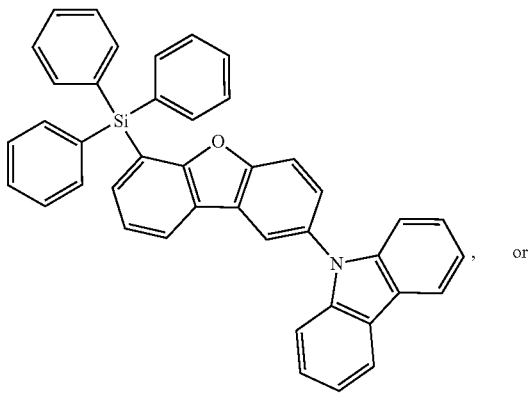
(SH-5)

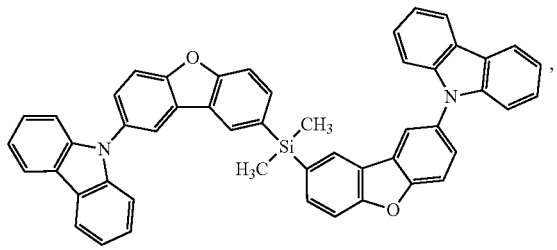
(SH-6)

are described in WO2010079051 (in particular pages on 19 to 26 and in tables on pages 27 to 34, pages 35 to 37 and pages 42 to 43).

Additional host materials on basis of dibenzofurane are, for example, described in US2009066226, EP1885818B1, EP1970976, EP1998388, EP2034538 and European patent application no. 14160197.1. Examples of particularly preferred host materials are shown below:

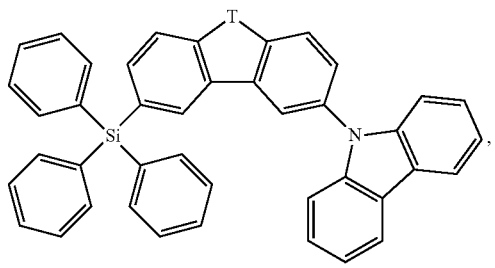

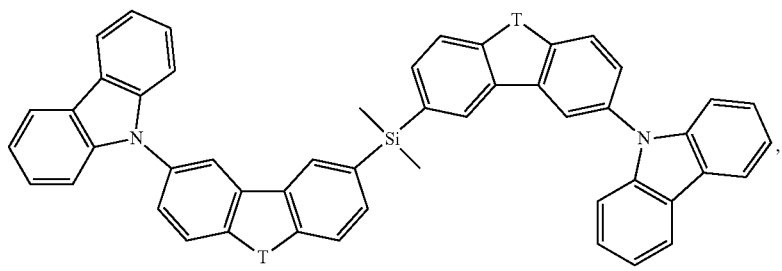

-continued
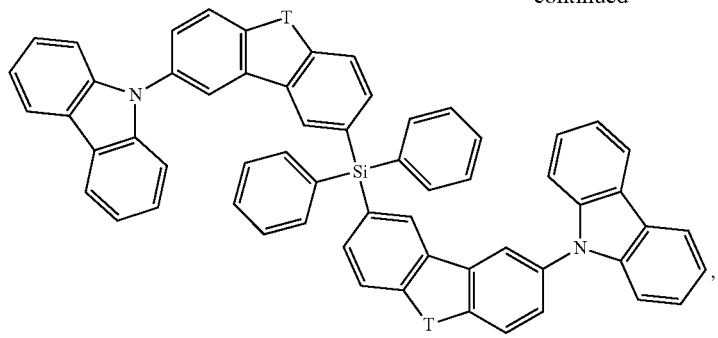
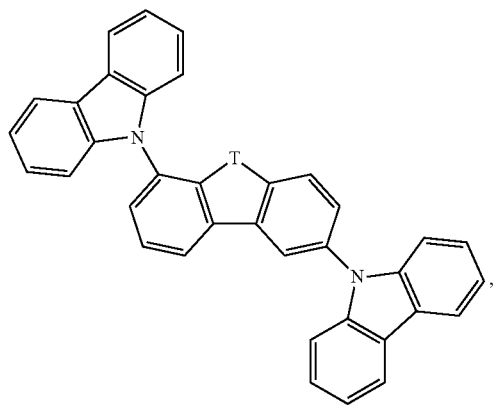
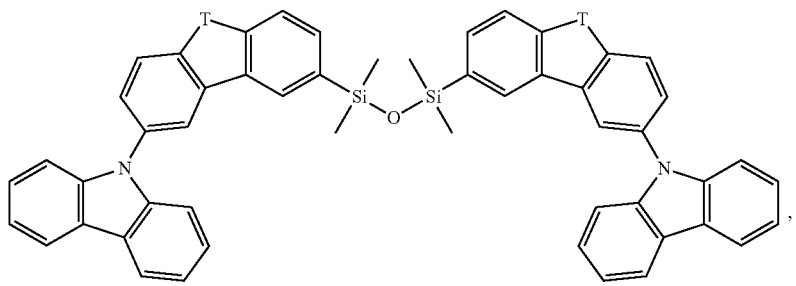
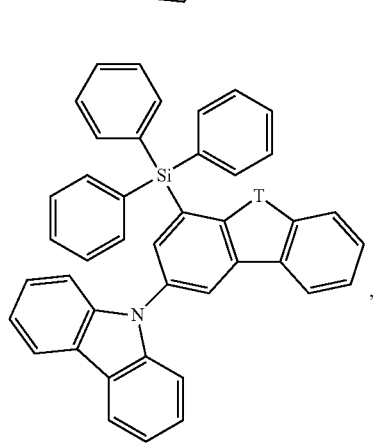
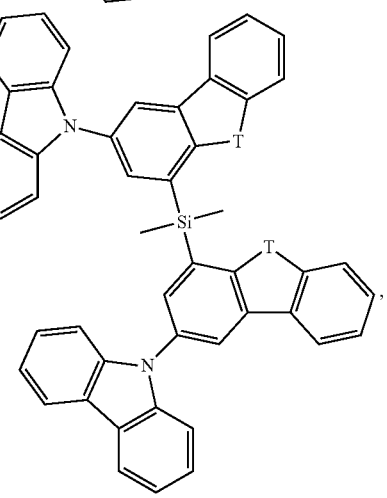

-continued
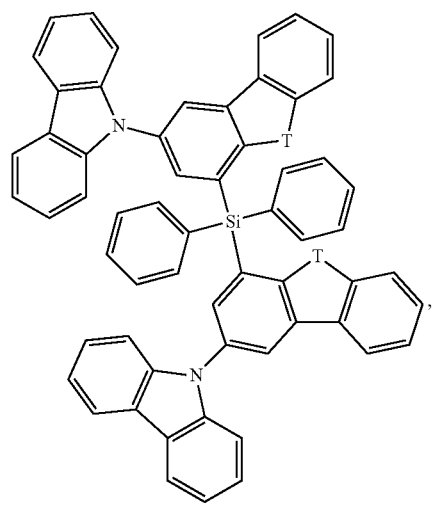
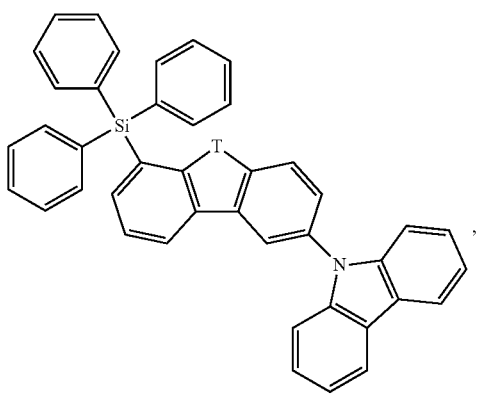
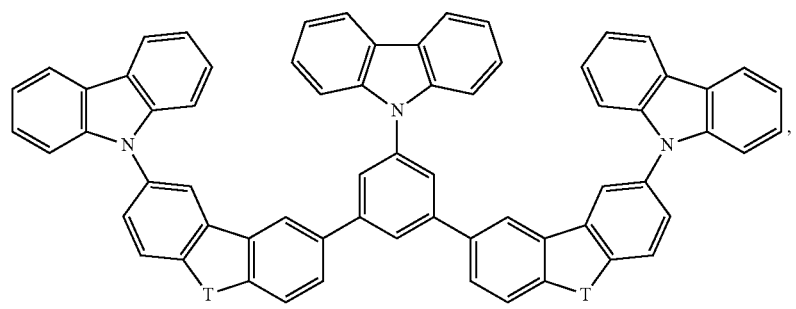
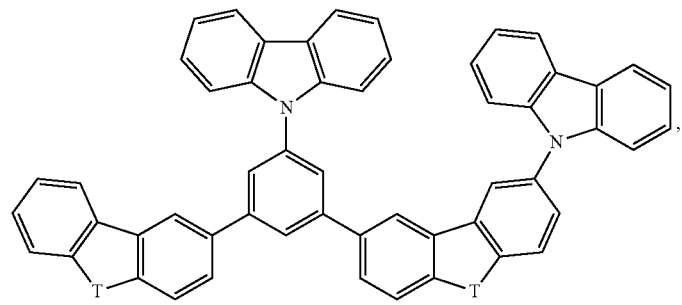
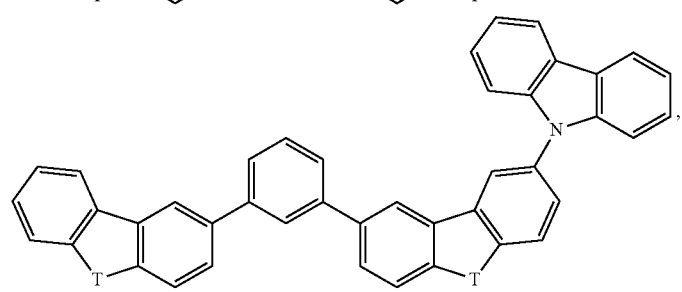
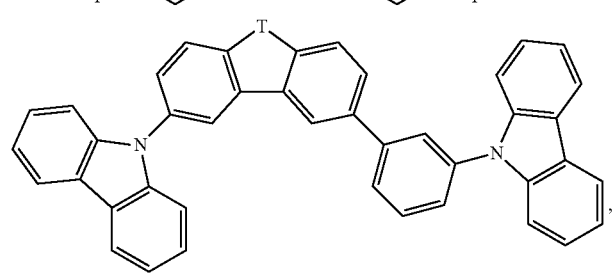

-continued
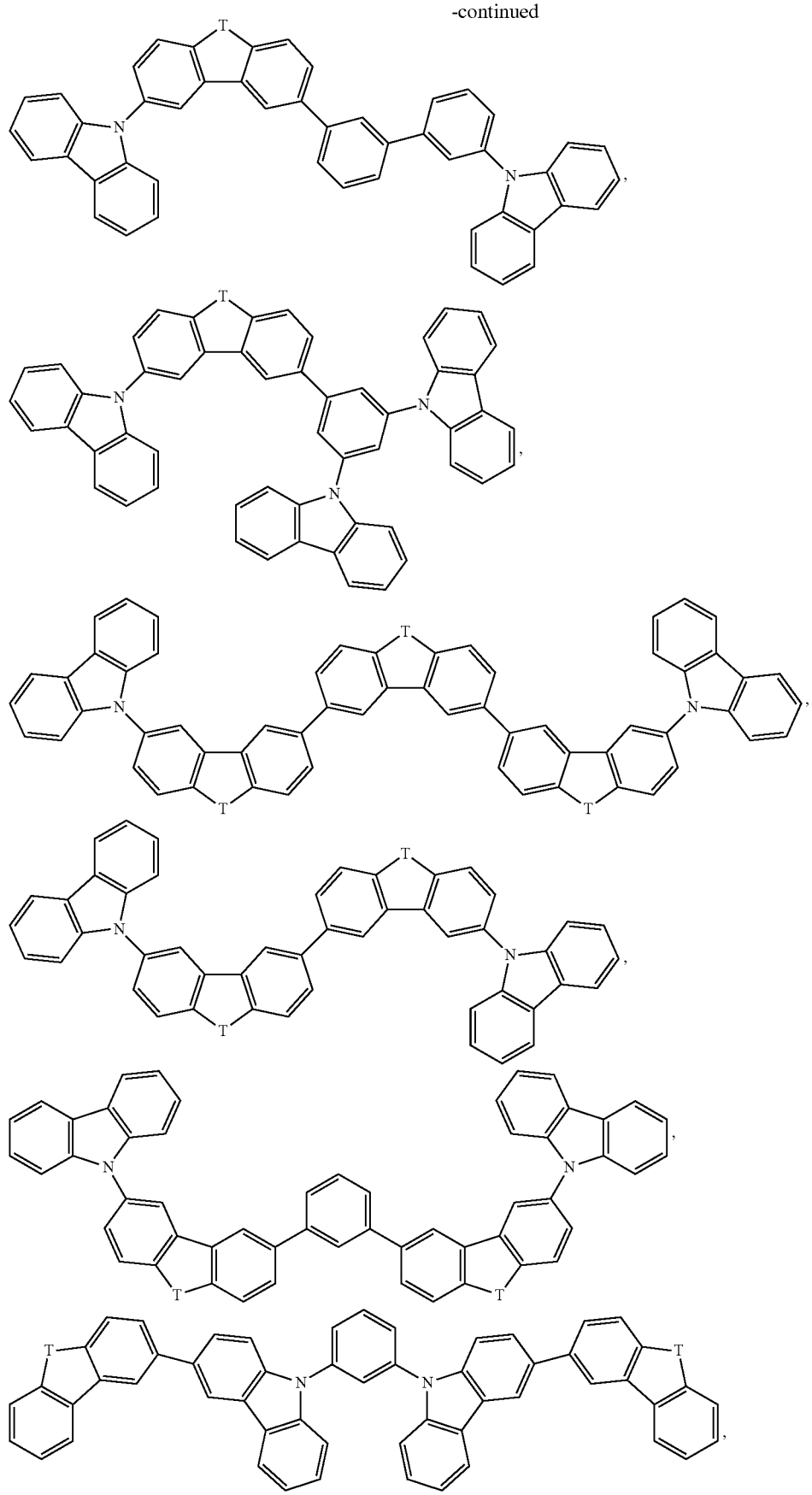

-continued
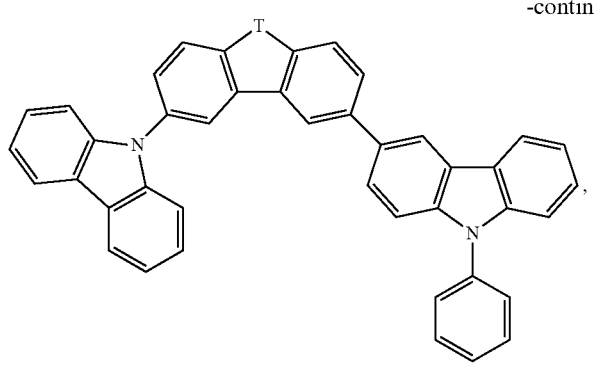
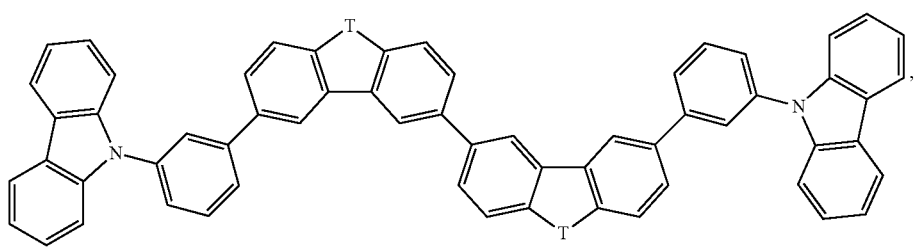
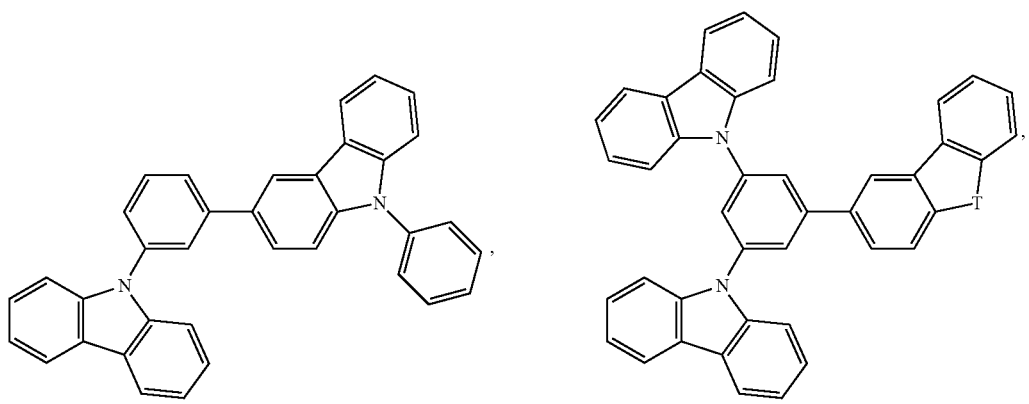
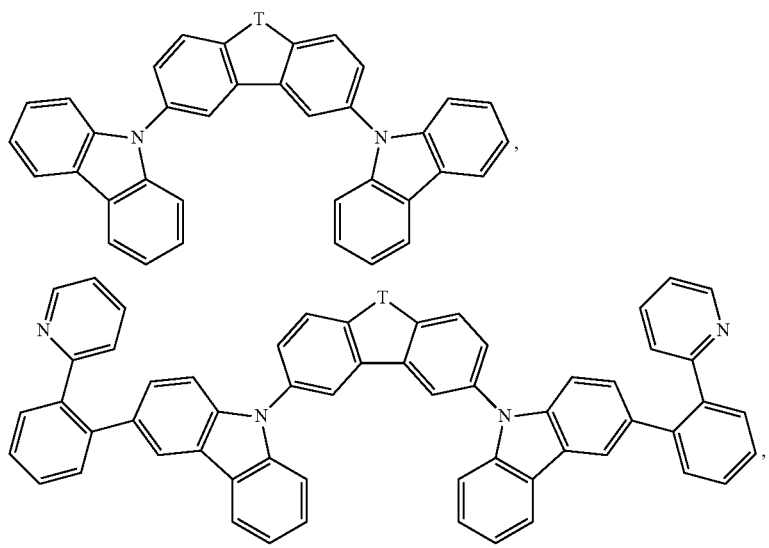

-continued
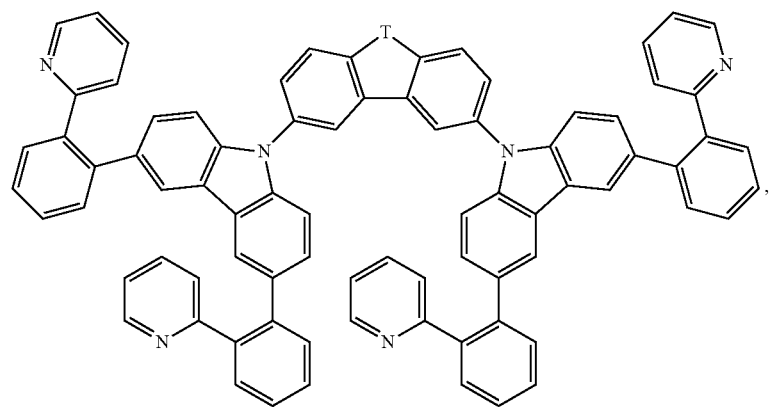
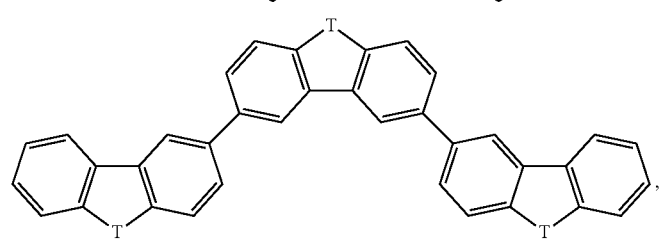
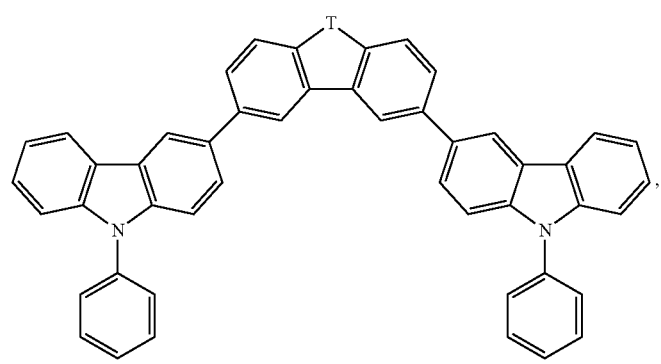
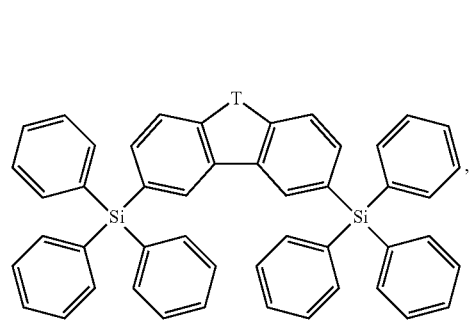
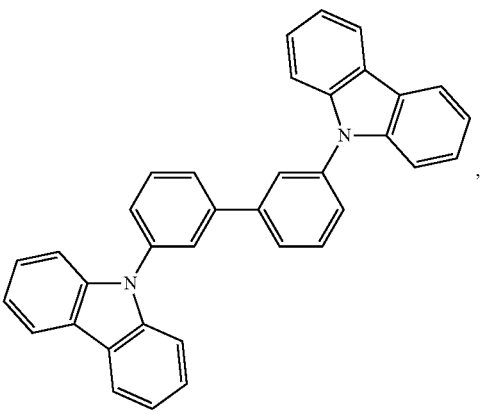
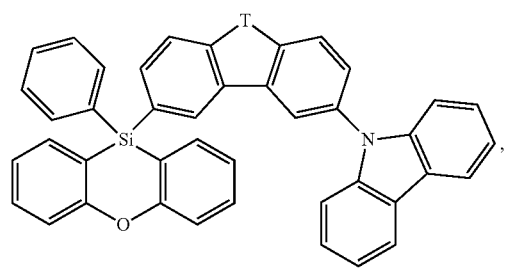
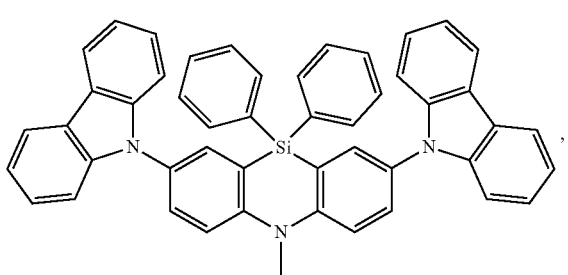

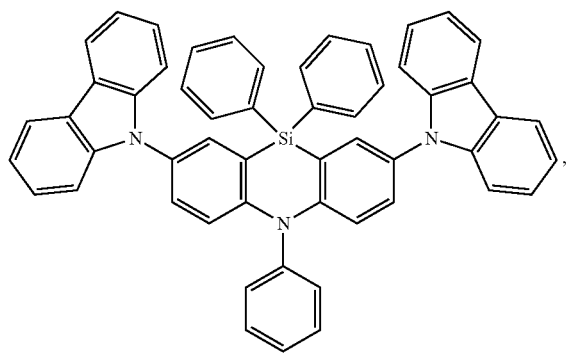
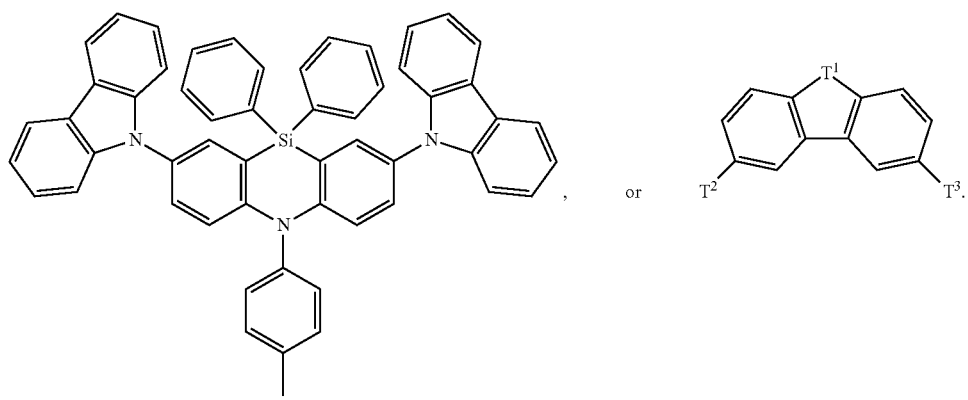
In the above-mentioned compounds T is O, or S, preferably O. If T occurs more than one time in a molecule, all groups T have the same meaning. $T^1$ is O, or S, preferably O. $T^1$ and $T^2$ are independently of each other
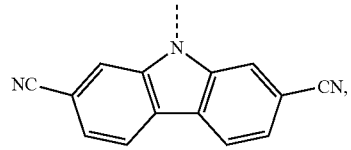
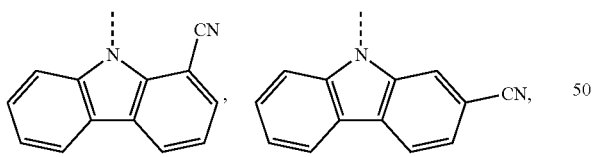
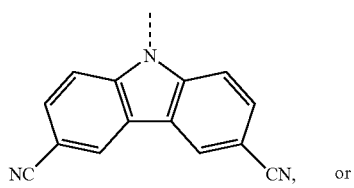
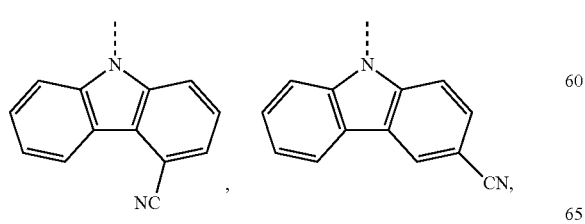
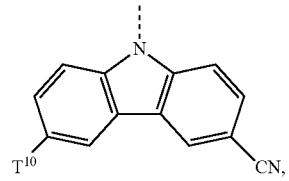
wherein $T^{10}$ is a $C_1$-$C_{25}$ alkyl group.

Compounds
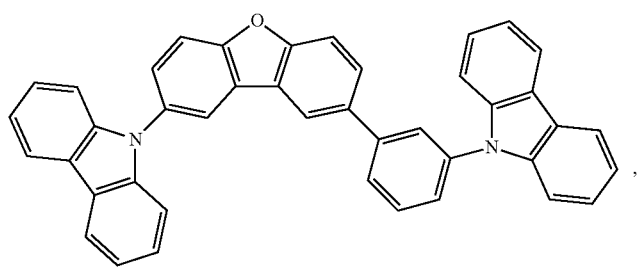
(SH-1)
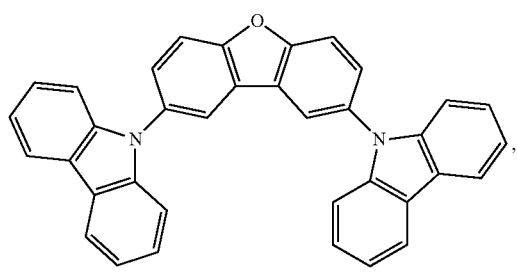
(SH-2)
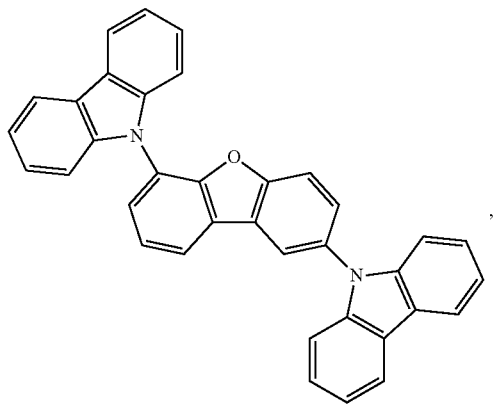
(SH-3) SH-4 SH-5 SH-6
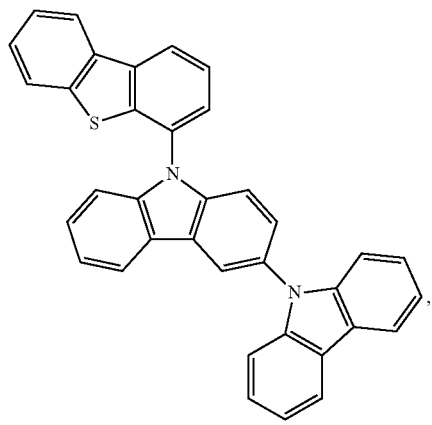
(SH-7)
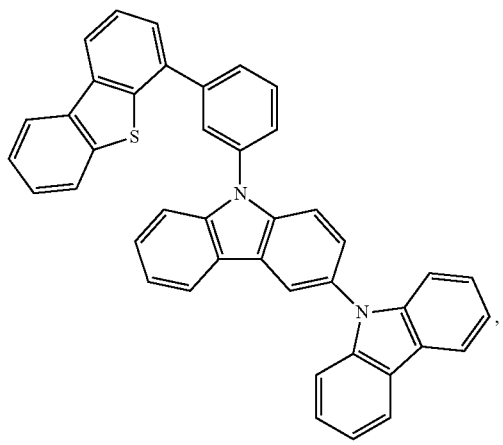
(SH-8)
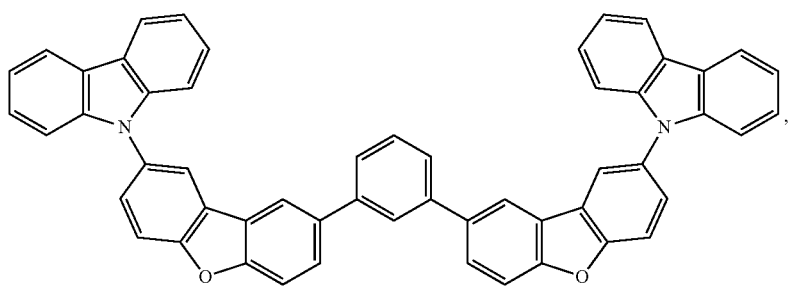
(SH-9)

(SH-10)

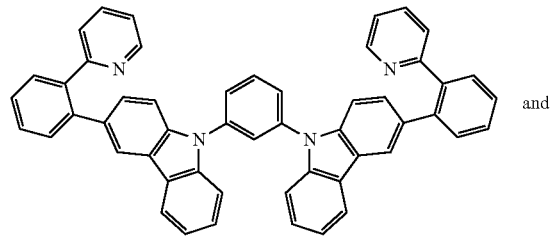

and (SH-11)

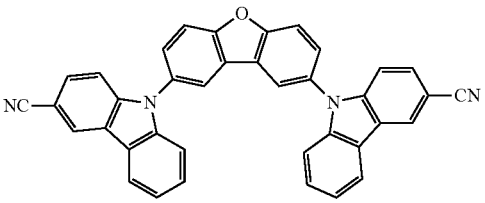

are most preferred.

Hole/Exciton Blocking Layer (f):

Blocking layers may be used to reduce the number of charge carriers (electrons or holes) and/or excitons that leave the emissive layer. The hole blocking layer may be disposed between the emitting layer (e) and electron transport layer (g), to block holes from leaving layer (e) in the direction of electron transport layer (g). Blocking layers may also be used to block excitons from diffusing out of the emissive layer.

Additional hole blocker materials typically used in OLEDs are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-transport material. Further suitable hole blockers and/or electron conductor materials are 2,2',2"-(1,3,5-benzenetriyl)tris(1-phenyl-1-H-benzimidazole), 2-(4-biphenylyl)-5-(4-tert-butylphenyl)-1, 3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di (naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl)borane, 2,9-bis (naphthalene-2-yl)-4,7-diphenyl-1,10-phenanthroline, 1-methyl-2-(4-(naphthalene-2-yl)phenyl)-1H-imidazo[4,5-f][1,10]phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO2009/003919 and WO2009003898 and disilyl compounds as disclosed in WO2008/034758, as a blocking layer for holes/excitons (f).

In another preferred embodiment compounds (SH-1), (SH-2), (SH-3), SH-4, SH-5, SH-6, (SH-7), (SH-8), (SH-9), (SH-10) and (SH-11) may be used as hole/exciton blocking materials.

In another preferred embodiment of the present invention, at least one compound of the formula I, especially a compound of formula (Ib-1), or (Ib-2), very especially a compound of the formula (Ib-1a), or (Ib-2a), such as, for example, compound (E-3), is used as hole/exciton blocker material.

Electron Transport Layer (g):

Electron transport layer may include a material capable of transporting electrons. Electron transport layer may be intrinsic (undoped), or doped. Doping may be used to enhance conductivity. Suitable electron-transporting materials for layer (g) of the inventive OLEDs comprise metals chelated with oxinoid compounds, such as tris(8-hydroxyquinolato)aluminum (Alq$_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

It is likewise possible to use mixtures of at least two materials in the electron-transporting layer, in which case at least one material is electron-conducting. Preferably, in such mixed electron-transport layers, at least one phenanthroline compound is used, preferably BCP, or at least one pyridine compound according to the formula (VIII) below, preferably a compound of the formula (VIIIaa) below. More preferably, in mixed electron-transport layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII). Reference is made to WO2011/157779.

The electron-transport layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transport layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, Cs$_2$CO$_3$, with alkali metal complexes, for example 8-hydroxyquinolatolithium (Liq), and with Y, Ce, Sm, Gd, Tb, Er, Tm, Yb, Li$_3$N, Rb$_2$CO$_3$, dipotassium phthalate, W(hpp)$_4$ from EP1786050, or with compounds described in EP1837926B1, EP1837927, EP2246862 and WO2010132236.

In a preferred embodiment, the electron-transport layer comprises at least one compound of the general formula (VII)

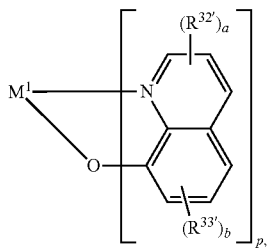

in which $R^{32'}$ and $R^{33'}$ are each independently F, $C_1$-$C_8$-alkyl, or $C_6$-$C_{14}$-aryl, which is optionally substituted by one or more $C_1$-$C_8$-alkyl groups, or two $R^{32'}$ and/or $R^{33'}$ substituents together form a fused benzene ring which is optionally substituted by one or more $C_1$-$C_8$-alkyl groups;

a and b are each independently 0, or 1, 2 or 3, $M^1$ is an alkaline metal atom or alkaline earth metal atom, p is 1 when $M^1$ is an alkali metal atom, p is 2 when $M^1$ is an earth alkali metal atom.

A very particularly preferred compound of the formula (VII) is

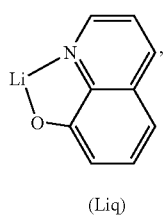

(Liq)

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transport layer comprises at least one compound of the formula (VIII),

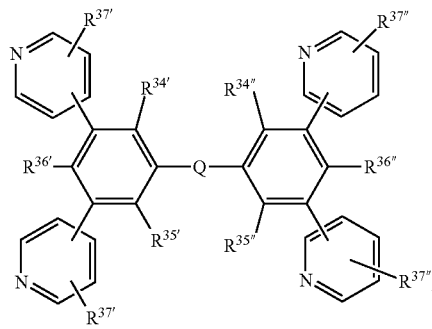

(VIII)

in which $R^{34''}$, $R^{35''}$, $R^{36''}$, $R^{37''}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E' and/or interrupted by D', $C_6$-$C_{24}$-aryl, $C_6$-$C_{24}$-aryl which is substituted by G', $C_2$-$C_{20}$-heteroaryl or $C_2$-$C_{20}$-heteroaryl which is substituted by G', Q is an arylene or heteroarylene group, each of which is optionally substituted by G';

D' is —CO—; —COO—; —S—; —SO—; —SO$_2$—; —O—; —NR$^{40'}$—; —SiR$^{45'}$R$^{46'}$—; —POR$^{47'}$—; —CR$^{38'}$=CR$^{39'}$—; or —C≡C—;

E' is —OR$^{44'}$; —SR$^{44'}$; —NR$^{40'}$R$^{41'}$; —COR$^{43'}$; —COOR$^{42'}$; —CONR$^{40'}$R$^{41'}$; —CN; or F;

G' is E', $C_1$-$C_{18}$-alkyl, $C_1$-$C_{18}$-alkyl which is interrupted by D', $C_1$-$C_{18}$-perfluoroalkyl, $C_1$-$C_{18}$-alkoxy, or $C_1$-$C_{18}$-alkoxy which is substituted by E' and/or interrupted by D', in which $R^{38'}$ and $R^{39'}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;

$R^{40'}$ and $R^{41'}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or $R^{40'}$ and $R^{41'}$ together form a 6-membered ring;

$R^{42'}$ and $R^{43'}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{44'}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{45'}$ and $R^{46'}$ are each independently $C_1$-$C_{18}$-alkyl, $C_6$-$C_{18}$-aryl or $C_6$-$C_{18}$-aryl which is substituted by $C_1$-$C_{18}$-alkyl, $R^{47'}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa)

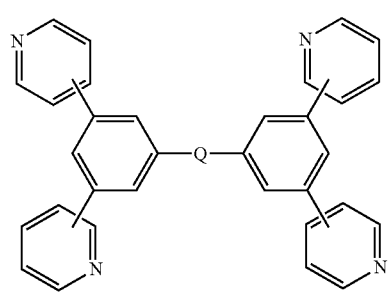

(VIIIa)

in which Q is:

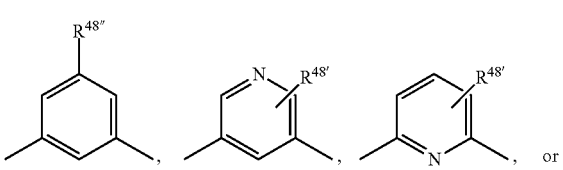

, , or

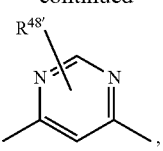

$R^{48'}$ is H or $C_1$-$C_{18}$-alkyl and
$R^{48''}$ is H, $C_1$-$C_{18}$-alkyl or

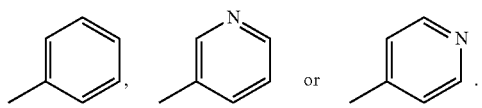

Particular preference is given to a compound of the formula

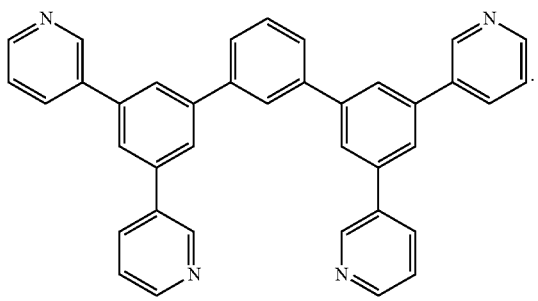

(ETM-2)

In a further, very particularly preferred embodiment, the electron-transport layer comprises a compound Liq and a compound ETM-2.

In a preferred embodiment, the electron-transport layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008/127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transport layer. Reference is made to WO2011/157790. Dibenzofuran compounds A-1 to A-36 and B-1 to B-22 described in WO2011/157790 are preferred, wherein dibenzofuran compound

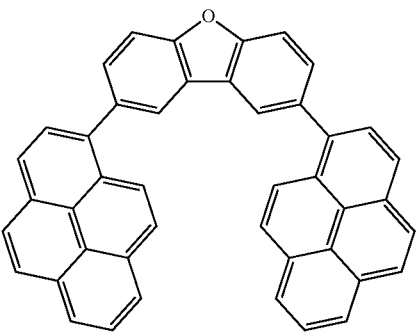

(A-10; = ETM-1)

is most preferred.

In a preferred embodiment, the electron-transport layer comprises Liq in an amount of 99 to 1% by weight, preferably 75 to 25% by weight, more preferably about 50% by weight, where the amount of Liq and the amount of the dibenzofuran compound(s), especially ETM-1, adds up to a total of 100% by weight.

In a preferred embodiment, the electron-transport layer comprises at least one phenanthroline derivative and/or pyridine derivative.

In a further preferred embodiment, the electron-transport layer comprises at least one phenanthroline derivative and/or pyridine derivative and at least one alkali metal hydroxyquinolate complex.

In a further preferred embodiment, the electron-transport layer comprises at least one of the dibenzofuran compounds A-1 to A-36 and B-1 to B-22 described in WO2011/157790, especially ETM-1.

In a further preferred embodiment, the electron-transport layer comprises a compound described in WO2012/111462, WO2012/147397, WO2012014621, such as, for example, a compound of formula

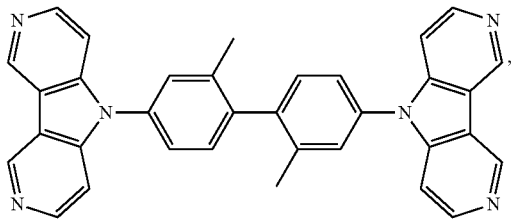

(ETM-3)

US2012/0261654, such as, for example, a compound of formula

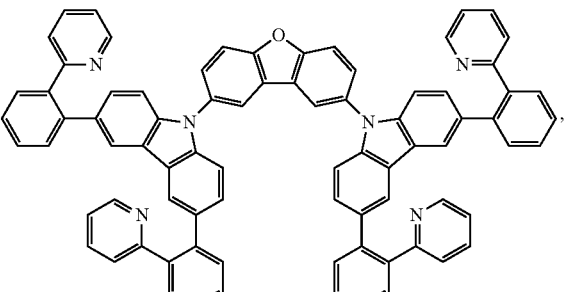

(ETM-4)

and WO2012/115034, such as for example, such as, for example, a compound of formula

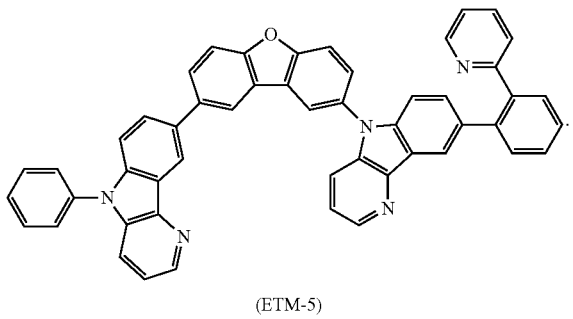 [SMILES: c1ccc(-n2c3ccc(-c4ccc5oc6ccc(-n7c8ccc(-c9ccccc9-c9ccccn9)cc8c8ncccc87)cc6c5c4)cc3c3ncccc32)cc1]

(ETM-5)

Electron Injection Layer (h):

The electron injection layer may be any layer that improves the injection of electrons into an adjacent organic layer. Lithium-comprising organometallic compounds such as 8-hydroxyquinolatolithium (Liq), CsF, NaF, KF, $Cs_2CO_3$ or LiF may be applied between the electron transport layer (g) and the cathode (i) as an electron injection layer (h) in order to reduce the operating voltage.

Cathode (i):

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

In general, the different layers, if present, have the following thicknesses:

anode (a): 500 to 5000 Å (ångström), preferably 1000 to 2000 Å;

hole injection layer (b): 50 to 1000 Å, preferably 200 to 800 Å, hole-transport layer (c): 50 to 1000 Å, preferably 100 to 800 Å, exciton blocking layer (d): 10 to 500 Å, preferably 50 to 100 Å, light-emitting layer (e): 10 to 1000 Å, preferably 50 to 600 Å, hole/exciton blocking layer (f): 10 to 500 Å, preferably 50 to 100 Å, electron-transport layer (g): 50 to 1000 Å, preferably 200 to 800 Å, electron injection layer (h): 10 to 500 Å, preferably 20 to 100 Å, cathode (i): 200 to 10 000 Å, preferably 300 to 5000 Å.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

Use of the compounds of the formula I in at least one layer of the OLED, preferably in the light-emitting layer (preferably as a matrix material), charge transport layer and/or in the charge/exciton blocking layer makes it possible to obtain OLEDs with high efficiency and with low use and operating voltage. Frequently, the OLEDs obtained by the use of the compounds of the formula I additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, can be used. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

Example 1

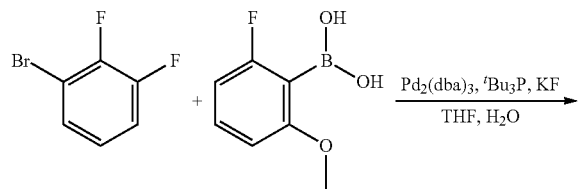

(C-1)

a) 1-Bromo-2,3-difluorobenzene (3.00 g, 15.45 mmol) and 2-fluoro-6-methoxybenzeneboronic acid (3.96 g, 23.32 mmol) were dissolved in THF (78 mL). To this solution potassium fluoride (2.71 g, 46.64 mmol) dissolved in water (8 mL) was added. To this solution tris(dibenzylideneacetone)dipalladium (0) (Pd$_2$(dba)$_3$) (711 mg, 0.78 mmol) and 1 M tri-tert-butylphosphine ($^t$Bu$_3$P) in toluene (1.55 mL) were added, and then the mixture was stirred at 60° C. for 18 h. After the reaction mixture was cooled to room temperature, a solid was removed by filtration. To the filtrate was water added, and the aqueous layer was extracted with tert-butyl methyl ether. The combined organic layer was washed with brine. After drying over MgSO$_4$, the solvent was removed under reduced pressure to give yellowish oil. The crude product was purified by column chromatography on silica gel eluting with a mixed solvent of heptane and tert-butyl methyl ether (95:5) to yield 2.33 g (63%) of 1,2-difluoro-3-(2-fluoro-6-methoxy-phenyl)benzene (C-1) as a yellow oil.

$^1$H-NMR (300 MHz, CDCl$_3$): δ 7.40-7.33 (m, 2H), 7.25-7.10 (m, 3H), 6.85-6.80 (m, 2H), 3.82 (s, 3H)

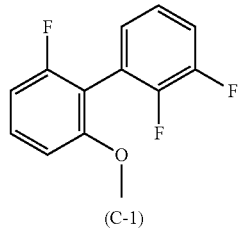

(C-1)     (C-2)

b) Compound C-1 (5.27 g, 22.1 mmol) was dissolved in CH$_2$Cl$_2$ (75 mL), and the solution was cooled at −78° C. To the solution was 1 M boron tribromide in heptane (26.5 mL, 26.5 mmol) added dropwise under N$_2$ atmosphere, and then the mixture was stirred overnight. The reaction mixture was poured into ice-water, and the aqueous layer was extracted with CH$_2$Cl$_2$. The combined organic layer was washed with water. After drying over MgSO$_4$, the solvent was removed under reduced pressure to give dark brown oil. The crude product was purified by column chromatography on silica gel eluting with a mixed solvent of heptane and ethyl acetate (6:1) to yield 5.10 g (97%) of 2-(2,3-difluorophenyl)-3-fluoro-phenol C-2 as brown resin. Compound C-2 was used for the next reaction without further purification.

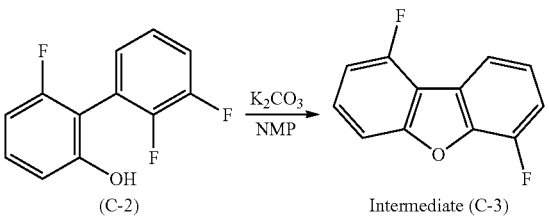

(C-2)     Intermediate (C-3)

c) Compound C-2 (11.43 g, 51.0 mmol) was dissolved in N-methylpyrrolidone (NMP) (101 mL). To the solution potassium carbonate (14.09 g, 102.0 mmol) was added, and the mixture was stirred at 150° C. overnight. After the reaction mixture was cooled at room temperature, it was diluted with 300 mL of water to give a solid. It was collected by filtration, and it was purified by column chromatography on silica gel eluting with heptane to yield 6.96 g of 1,6-difluorodibenzofuran (C-3) as a white solid.

$^1$H-NMR (300 MHz, CDCl$_3$): δ 7.86 (dd, J=7.6, 1.3 Hz, 1H), 7.52-7.44 (m, 2H), 7.37-7.23 (m, 2H). 7.13-7.05 (m, 1H)

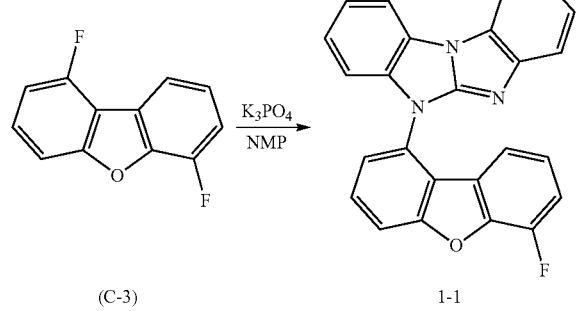

(C-3)     1-1 c) Intermediate C-3 (2.23 g, 10.9 mmol), benzimidazolo[1,2-a]benzimidazole (2.26 g, 10.9 mmol), and potassium phosphate (2.78 g, 13.1 mmol) were suspended in NMP (66 mL). The mixture was stirred at 150° C. for 48 h. After the reaction mixture was cooled at room temperature, 66 mL of EtOH and 244 mL of water were added there to give a solid. This solid was collected by filtration, and it was purified by column chromatography on silica gel eluting with a mixed solvent of heptane and CHCl$_3$ to yield 1.74 g (41%) of compound 1-1 as a white solid. LC-MS (m/z) 391

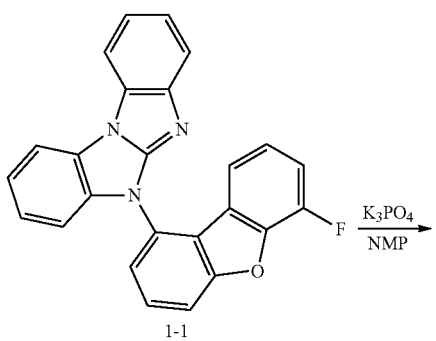

1-1

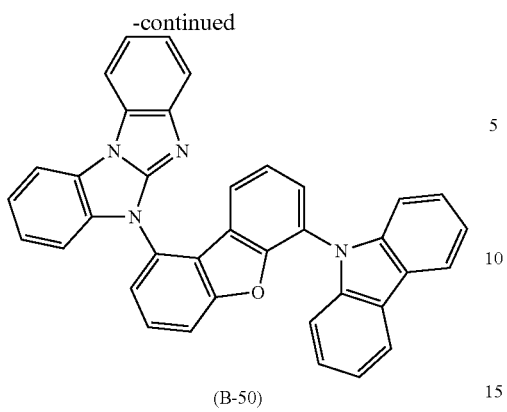

(B-50)

d) Compound 1-1 (1.7 g, 4.3 mmol), carbazole (762 mg, 4.5 mmol), and potassium phosphate (1.94 g, 9.1 mmol) were suspended in NMP (22 mL). The mixture was stirred at 190° C. overnight. After the reaction mixture was cooled at room temperature, 90 mL of water was added to the reaction mixture to give a solid. It was collected by filtration, and it was purified by column chromatography on silica gel eluting with a mixed solvent of heptane and CHCl$_3$ to yield B-50 (1.83 g (78%)) as a white solid.

$^1$H-NMR (300 MHz, CDCl$_3$): δ 8.26-8.22 (m, 2H), 8.03-7.96 (m, 2H), 7.82-7.79 (m, 1H), 7.72-7.63 (m, 4H), 7.52-7.33 (m, 8H), 7.30-7.23 (m, 4H), 7.08 (dd, J=7.9, 1.1 Hz, 1H) LC-MS (m/z) 538

Example 2

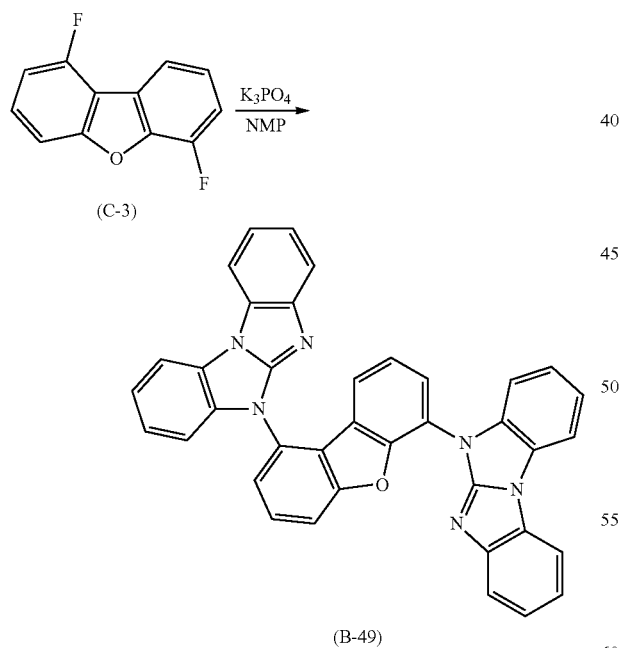

(C-3)

(B-49)

a) Intermediate C-3 (2.5 g, 12.0 mmol) and benzoimidazolo[1,2-a]benzimidazole (6.0 g, 29 mmol) were entered in N-methylpyrrolidone (35 mL). To the mixture was potassium phosphate (12.4 g, 58.1 mmol) added, and the mixture was stirred at 190° C. for 32 h. After the reaction mixture was cooled at room temperature, 50 mL of water was poured into the reaction mixture to give a brown solid. The crude product was purified by column chromatography on silica gel eluting with a mixed solvent of ethyl acetate and CH$_2$Cl$_2$ to yield compound B-49 (3.9 g (56%)) as a white solid. LC-MS (m/z) 579 (M+1).

$^1$H-NMR (300 MHz, CDCl$_3$): δ 7.98-7.96 (m, 2H), 7.91-7.90 (m, 2H), 7.83 (d, J=8.5 Hz, 1H), 7.78-7.68 (m, 4H), 7.48-7.24 (m, 11H), 7.14 (d, J=7.8 Hz, 1H), 7.04 (d, J=8.5 Hz, 1H)

Example 3

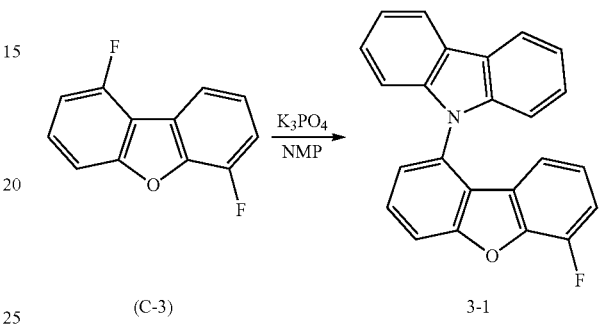

(C-3)                    3-1 a) Intermediate C-3 (1.55 g, 4.4 mmol), carbazole (762 mg, 4.5 mmol), and potassium phosphate (1.94 g, 9.1 mmol) were suspended in NMP (22 mL). The mixture was stirred at 190° C. overnight. After the reaction mixture was cooled at room temperature, 90 mL of water was added to the reaction mixture to give a solid. It was collected by filtration, and it was purified by column chromatography on silica gel eluting with a mixed solvent of heptane and CHCl$_3$ to yield 1.83 g (78%) of 3-1 as a white solid.

$^1$H-NMR (300 MHz, CDCl$_3$): δ 8.29-8.23 (m, 2H), 7.83 (dd, J=1.0, 8.3 Hz, 1H), 7.77-7.71 (m, 1H), 7.57 (dd, J=1.0, 7.6 Hz, 1H), 7.41-7.32 (m, 4H), 7.18-7.10 (m, 3H), 6.89-6.82 (m, 1H), 6.23 (dd, J=1.0, 8.0 Hz, 1H)

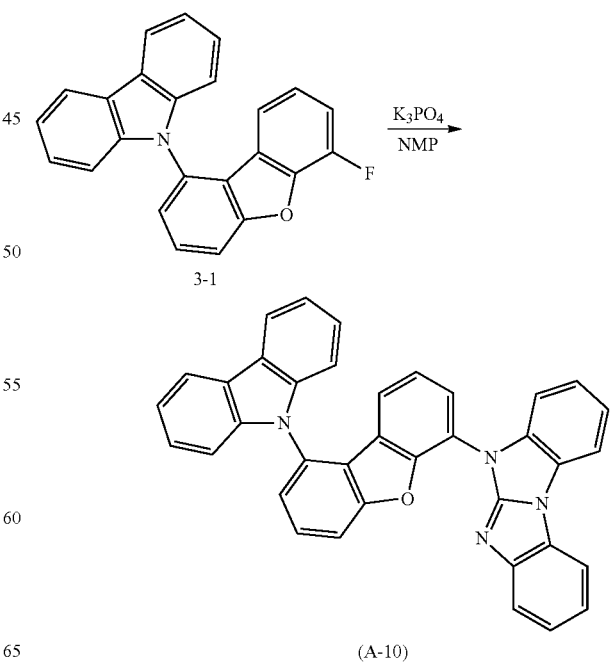

3-1

(A-10)

b) Compound 3-1 (1.55 g, 4.4 mmol), benzimidazolo[1,2-a]benzimidazole (960 mg, 4.6 mmol), and potassium phosphate (1.97 g, 9.3 mmol) were suspended in NMP (22 mL). The mixture was stirred at 190° C. for 18.5 h. After the reaction mixture was cooled at room temperature, 44 mL of EtOH and 22 mL of water were added to the reaction mixture to give a solid. It was collected by filtration, and it was purified by column chromatography on silica gel eluting with a mixed solvent of toluene and CHCl$_3$. The product was further purified by recrystallization with toluene and cyclohexane to result in compound A-10 (yield: 1.55 g (65%)) as a white solid. LC-MS (m/z) 538.

$^1$H-NMR (300 MHz, DMSO-d6): δ 8.42-8.39 (m, 2H), 8.32-8.25 (m, 2H), 7.95-7.82 (m, 3H), 7.72 (dd, J=1.2, 7.6 Hz, 1H), 7.61-7.58 (m, 1H), 7.50-7.32 (m, 9H), 7.25 (t, J=7.9 Hz, 1H), 7.20-7.17 (m, 2H), 6.38 (dd, J=1.1, 8.0 Hz, 1H)

Example 4

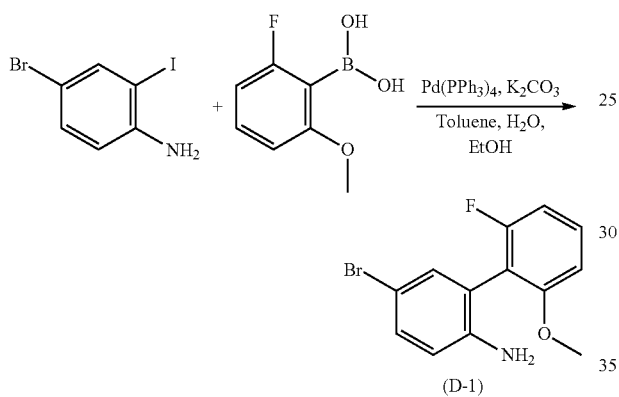

a) 5.3 g of 4-Bromo-2-iodoaniline and 3.63 g of 6-fluoro-2-methoxyphenyl boronic acid were dissolved in 346 mL of toluene and 201 mL of ethanol. Separately, 7.38 g of potassium carbonate was dissolved in 56 mL of water, and the solution was added there. After 616 mg of Pd(PPh$_3$)$_4$ was added there, the mixture was stirred at 80° C. for 48 h. After the reaction mixture was cooled at room temperature, the reaction mixture was partly evaporated, and diluted with water and toluene. The aqueous layer was extracted with toluene. The organic layers were washed with brine, dried with Na$_2$SO$_4$. After Na$_2$SO$_4$ was removed by filtration and evaporated to give 6.38 g of dark-brown oil. The product was purified by column chromatography on silica gel eluting with a mixed solvent of heptane and ethyl acetate (3:1) to yield 4.25 g (81%) 4-bromo-2-(2-fluoro-6-methoxy-phenyl)aniline (D-1) as a light brown resin.

$^1$H-NMR (300 MHz, CDCl$_3$): δ 7.39-7.28 (m, 2H), 7.22 (d, J=7.2 Hz, 1H), 6.87-6.80 (m, 2H), 6.71 (d, J=6.7 Hz, 1H), 3.82 (s, 3H)

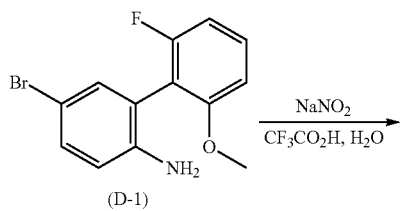

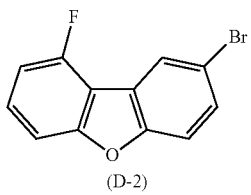

b) Compound D-1 (12.3 g, 41.54 mmol) was dissolved in trifluoroacetic acid (69 mL), and the solution was cooled at 0° C. Sodium nitrite (3.44 g, 49.84 mmol) dissolved in water (6.9 mL) was added dropwise there. After completion of the addition, the mixture was stirred at 70° C. for 2 h. After the reaction mixture was cooled at room temperature, it was diluted with 70 mL of ethanol to give a solid. The solid was collected by filtration, and the crude product was purified by column chromatography on silica gel eluting with cyclohexane to yield 7.09 g (58%) of 2-bromo-8-fluorodibenzofuran (D-2) as a white solid.

$^1$H-NMR (300 MHz, CDCl$_3$): δ 8.21 (dd, J=0.5, 2.0 Hz, 1H), 7.61 (dd, J=2.0, 8.7 Hz, 1H), 7.50-7.37 (m, 3H), 7.11-7.05 (m, 1H)

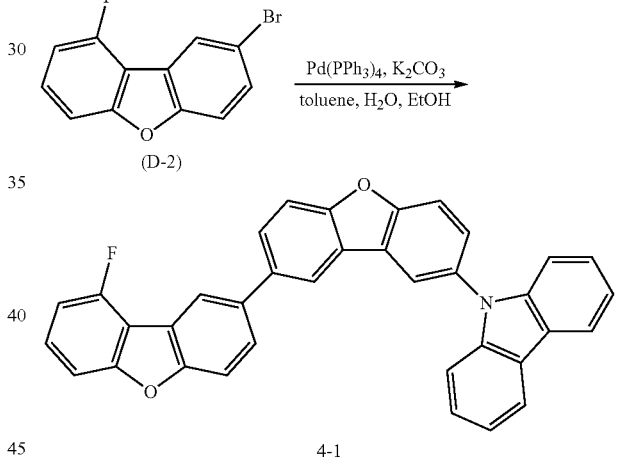

c) Intermediate D-2 (2.1 g, 7.9 mmol) and 9-[8-(4,4,5,5-tetramethyl-1,3,2-dioxaborolan-2-yl)dibenzofuran-2-yl]carbazole (4 g, 8.7 mmol) were dissolved in 103 mL of toluene and 53 mL of EtOH. To the solution was potassium carbonate (3.28 g, 23.8 mmol) dissolved in 18 mL of water added. After Pd(PPh$_3$)$_4$ (274 mg, 0.24 mmol) was added there, the mixture was stirred at 80° C. for 48 h. After the reaction mixture was cooled at room temperature, it was diluted with water and toluene. Then, the aqueous layer was extracted with toluene. The organic layer was washed with brine, and dried with Na$_2$SO$_4$. After removal of Na$_2$SO$_4$ by filtration, the filtrate was concentrated to give a white solid. The crude product was purified by column chromatography on silica gel eluting with a mixed solvent of cyclohexane and toluene to yield 4.26 g (99%) of compound 4-1 as a white solid. LC-MS (m/z) 517.

$^1$H-NMR (300 MHz, CDCl$_3$): δ 8.35-8.34 (m, 1H), 8.25-8.19 (m, 4H), 7.89-7.76 (m, 4H), 7.70-7.67 (m, 2H), 7.47-7.42 (m, 6H), 7.37-7.31 (m, 2H), 7.12-7.06 (m, 1H)

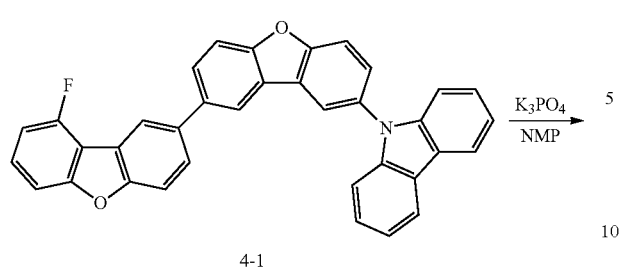

4-1

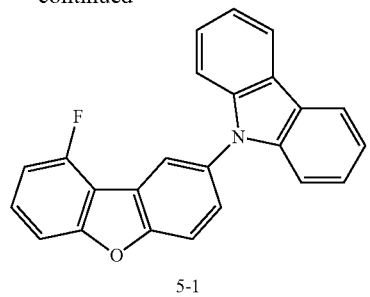

5-1 a) Intermediate D-2 (2.12 g, 8.0 mmol), carbazole (1.34 g, 8.0 mmol) and sodium tert-butoxide (1.08 g 11.2 mmol) were added to toluene (40 mL). To the suspension were $^{t}Bu_{3}P$—$HBF_{4}$ (185 mg, 0.64 mmol) and $Pd_{2}(dba)_{3}$ (146 mg, 0.16 mmol) added, and the mixture was refluxed for 48 h. After the reaction mixture was cooled at room temperature, it was diluted with 40 mL of cyclohexane. The solid was removed by filtration, and the filtrate was concentrated to give compound 5-1 as a colorless resin. LC-MS (m/z) 517.

$^{1}$H-NMR (300 MHz, $CDCl_{3}$): δ 8.27 (dd, J=0.5, 2.1 Hz, 1H), 8.22-8.19 (m, 2H), 7.81 (dd, J=0.5, 8.7 Hz, 1H), 7.68 (dd, J=2.1, 8.7 Hz, 1H), 7.55-7.39 (m, 6H), 7.36-7.31 (m, 2H), 7.14-7.08 (m, 1H)

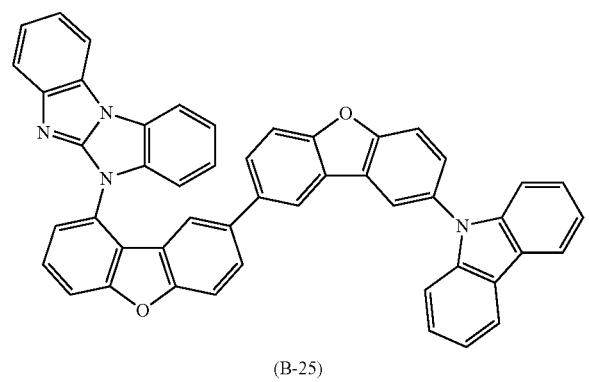

(B-25)

d) Compound 4-1 (3 g, 5.8 mmol), benzimidazolo[1,2-a]benzimidazole (1.26 g, 6.1 mmol), and potassium phosphate (2.58 g, 12.2 mmol) were suspended in NMP (29 mL). The mixture was stirred at 190° C. for 48 h. After the reaction mixture was cooled at room temperature, 58 mL of EtOH and 29 mL of water were added to the reaction mixture to give a solid. It was collected by filtration, and it was purified by column chromatography on silica gel eluting with a mixed solvent of toluene and $CHCl_{3}$. Then, the product was recrystallized with toluene and heptane. The formed solid was collected by filtration and dried in vacuum to yield 2.39 g (59%) of compound (B-25) as a white solid. LC-MS (m/z) 704.

$^{1}$H-NMR (300 MHz, DMSO-d6): δ 8.39-8.36 (m, 2H), 8.15-8.12 (m, 1H), 8.01-7.72 (m, 9H), 7.61-7.25 (m, 13H), 7.01 (d, J=1.4 Hz, 1H), 7.54 (td, J=7.5, 1.2 Hz, 1H), 6.57 (td, J=7.5, 1.2 Hz, 1H)

Example 5

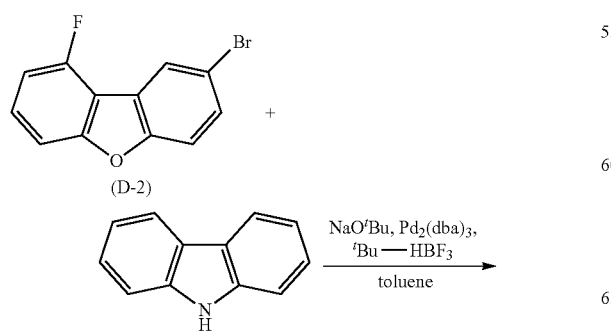

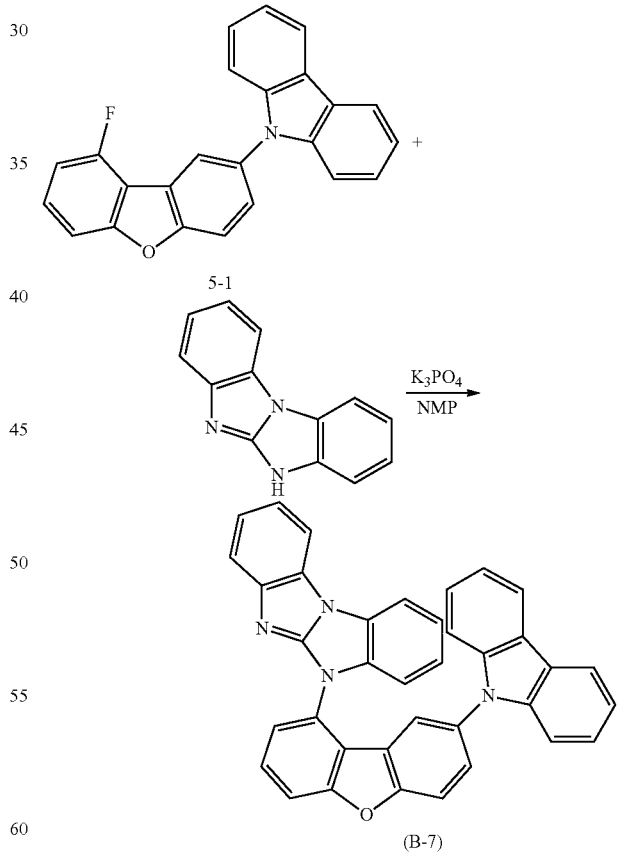

b) Compound 5-1 (321 mg, 0.9 mmol), benzimidazolo[1,2-a]benzimidazole (199 mg, 0.96 mmol), and potassium phosphate (407 g, 1.92 mmol) were added to NMP (5 mL). The mixture was stirred at 190° C. overnight. After reaction mixture was cooled at room temperature, it was diluted with 10 mL of EtOH and 5 mL of water to give a solid. The solid was collected by filtration. The crude product was purified by column chromatography on silica gel eluting with a mixed solvent of toluene and CH$_2$Cl$_2$ to yield 489 mg (99%) of compound B-7 as a white solid. LC-MS (m/z) 539 [M+H]$^+$

Example 6

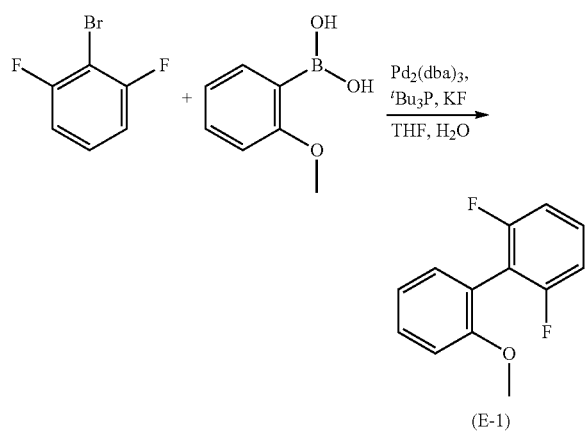

a) 2-bromo-1,3-difluoro-benzene (11.52 g, 59.7 mmol), (2-methoxyphenyl)boronic acid (11.52 g, 75.8 mmol), potassium fluoride (10.94 g, 188.3 mmol), THF (240 mL), and water (24 mL) were entered into a flask. To this solution Pd$_2$(dba)$_3$ (2.76 g, 3.01 mmol) and 1 M $^t$Bu$_3$P in toluene (6 mL) were added, and then the mixture was refluxed for 48 h. After cooling down to room temperature, the reaction mixture was poured into water. The aqueous layer was extracted with ethyl acetate (AcOEt) and the combined organic layer was washed with brine. After drying over MgSO$_4$, the solvent was removed under reduced pressure to give yellowish liquid. The crude product was purified by column chromatography on silica gel eluting with a mixed solvent of heptane and AcOEt (10:1) to yield 12.24 g (81%) of 1,3-difluoro-2-(2-methoxyphenyl)benzene (E-1) as a beige solid.

$^1$H-NMR (300 MHz, CDCl$_3$): δ 7.49-7.43 (m, 1H), 7.36-7.26 (m, 2H), 7.09-6.95 (m, 4H), 3.83 (s, 3H)

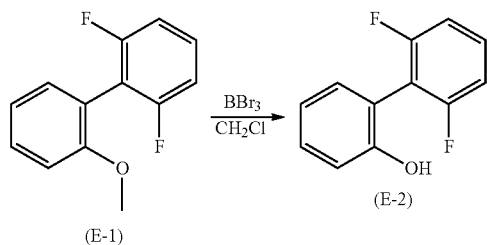

b) Compound E-1 (12.24 g, 55.6 mmol) was dissolved in CH$_2$Cl$_2$ (200 mL), and the solution was cooled at −78° C. To the solution was 1 M boron tribromide in heptane (89 mL, 89 mmol) added dropwise under N$_2$ atmosphere, and then the mixture was stirred overnight. The reaction mixture was poured into ice-water, and the aqueous layer was extracted with CH$_2$Cl$_2$. The combined organic layer was washed with water. After drying over MgSO$_4$, the solvent was removed under reduced pressure to give 2-(2,6-difluorophenyl)phenol E-2 as yellowish liquid (11.42 g, 99%).

$^1$H-NMR (300 MHz, CDCl$_3$): δ 7.43-7.33 (m, 2H), 7.29-7.26 (m, 1H), 7.08-7.00 (m, 4H), 4.93 (br, 1H)

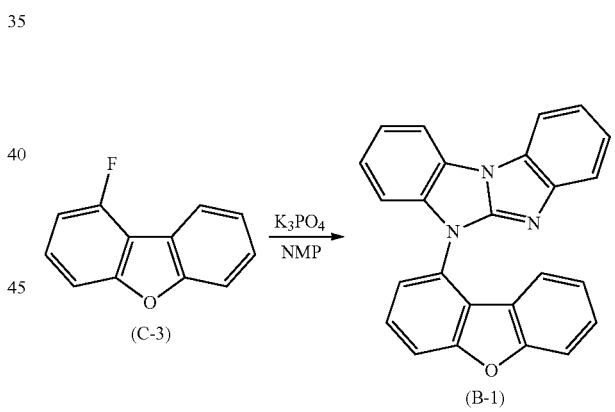

c) Compound E-2 (12.08 g, 65 mmol) was dissolved in N-methylpyrrolidone (80 mL). To the solution was potassium carbonate (18.02 g, 130 mmol) added. Then, the mixture was stirred at 180° C. for 5 h. After the reaction mixture was cooled at room temperature, it was poured into water to give a solid. The solid was collected by filtration, washed with water, and dried over into a vacuum oven to give 10.8 g (99%) of 1-fluorodibenzofuran (E-3) as a white solid.

$^1$H-NMR (300 MHz, CDCl$_3$): δ 8.10 (dq, J=7.7, 0.8 Hz, 1H), 7.60 (dq, J=8.3, 0.7 Hz, 1H), 7.51 (td, J=8.3, 1.5 Hz, 1H), 7.49-7.38 (m, 3H), 7.10-7.04 (m, 1H)

d) Intermediate (E-3) (1.3 g, 7.0 mmol) and benzoimidazolo[1,2-a]benzimidazole (1.52 g, 7.3 mmol) were entered in N-methylpyrrolidone (20 mL). To the mixture was potassium phosphate (3.12 g, 14.7 mmol) added, and the mixture was stirred at 180° C. for 40 h. After the reaction mixture was cooled at room temperature, 50 mL of water was poured into the reaction mixture to give a grey solid. The solid was collected by filtration, and washed with water and ethanol. The crude product was purified by column chromatography on silica gel eluting with CH$_2$Cl$_2$ to yield 1.87 g (71%) of compound (B-1) as a white solid.

$^1$H-NMR (300 MHz, CDCl$_3$): δ 7.98-7.95 (m, 2H), 7.81-7.73 (m, 4H), 7.63 (dt, J=0.8, 8.3 Hz, 1H), 7.45-7.35 (m, 4H), 730-7.26 (m, 1H), 7.12 (dt, J=0.8, 8.0 Hz, 1H), 7.04 (td, J=0.9, 7.6 Hz, 1H), 6.91 (dq, J=0.6, 1.5, 7.9 Hz, 1H)

Example 7

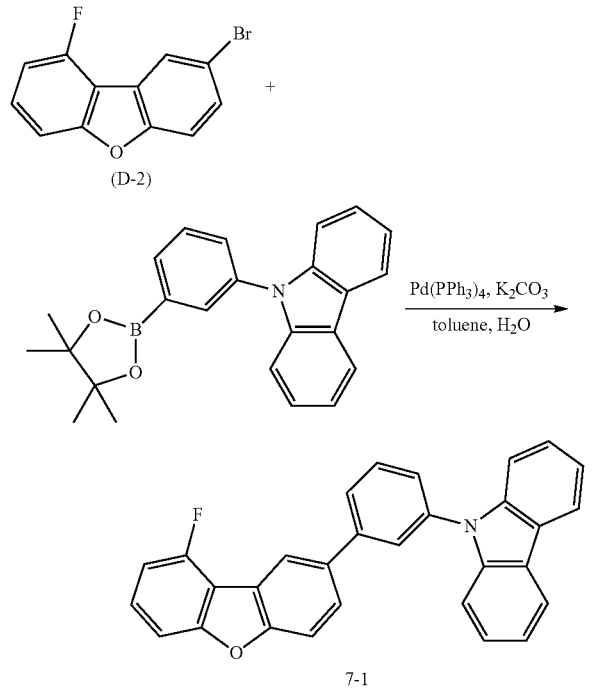

a) Intermediate (D-2) (2.8 g, 10.6 mmol) and 9-[3-(4,4,5,5-tetramethyl-1,3,2-dioxaborolan-2-yl)phenyl]carbazole (4.6 g, 15.6 mmol) were dissolved in 50 mL of toluene. To the solution was potassium carbonate (3.28 g, 23.8 mmol) dissolved in 16 mL of water added. After Pd(PPh$_3$)$_4$ (610 mg, 5.3 mmol) was added there, the mixture was stirred at 85° C. for 2 h. After the reaction mixture was cooled at room temperature, it was diluted with water and toluene. Then, the aqueous layer was extracted with toluene. The organic layer was washed with brine, and dried with Na$_2$SO$_4$. After removal of Na$_2$SO$_4$ by filtration, the filtrate was concentrated to give a white solid. The crude product was purified by column chromatography on silica gel eluting with toluene to yield 5.4 g (97%) of compound 7-1 as a white solid.

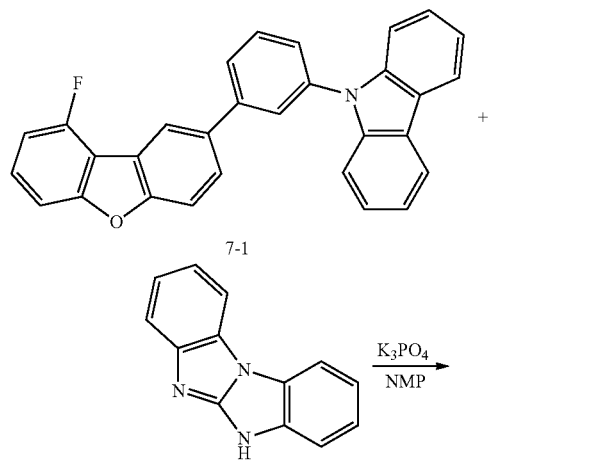

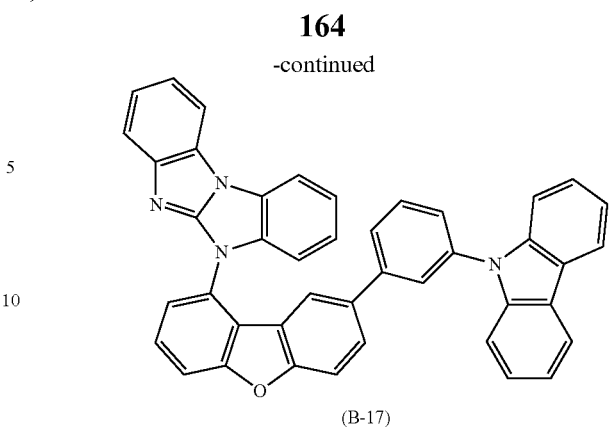

b) Compound 7-1 (3.0 g, 7.0 mmol), benzimidazolo[1,2-a]benzimidazole (1.8 g, 8.4 mmol), and potassium phosphate (3.6 g, 29.8 mmol) were added to NMP (35 mL). The mixture was stirred at 190° C. for 8 h. After reaction mixture was cooled at room temperature, it was diluted with 40 mL of water to give a solid. The solid was collected by filtration, and it was washed with 100 mL of water. The crude product was purified by column chromatography on silica gel eluting with toluene to yield 2.5 g (58%) of compound B-17 as a white solid. LC-MS (m/z) 615 [M+H]$^+$

Example 8

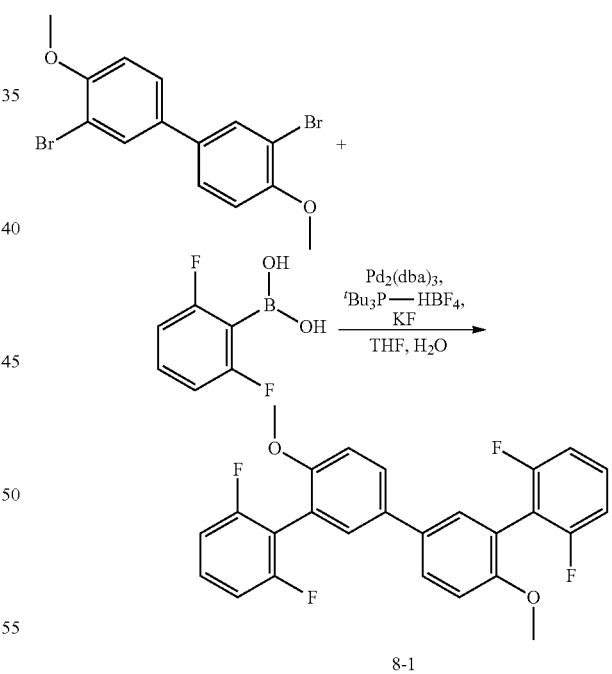

a) 2-bromo-4-(3-bromo-4-methoxy-phenyl)-1-methoxybenzene (30.7 g, 82.5 mmol) and 2-fluoro-6-methoxybenzeneboronic acid (31.3 g, 198 mmol) were dissolved in THF (300 mL) and water (30 mL). To this solution Pd$_2$(dba)$_3$ (7.55 g, 8.25 mmol), $^t$Bu$_3$P—HBF$_4$ (4.79 g, 16.5 mmol), potassium fluoride (28.8 g, 195 mmol) were added, and then the mixture was stirred at 60° C. for 8 h. After the reaction mixture was cooled to room temperature, the solvent was removed by evaporation. The crude product was dissolved in 1.5 L of CH$_2$Cl$_2$, and it was purified by column chromatography on silica gel eluting with CH$_2$Cl$_2$. The obtained product was suspended in 90 mL of toluene, and the suspension was stirred at 90° C. for 1 h. After it was cooled at room temperature, the solid was collected by filtration, and washed with hexane to yield 33.6 g (93%) of compound 8-1 as a white solid.

$^1$H-NMR (300 MHz, CDCl$_3$): δ 7.61 (dd, J=2.4, 8.8 Hz, 2H), 7.48 (d, J=2.4 Hz, 2H), 7.31-7.25 (m, 2H), 7.06 (d, J=8.8 Hz, 2H), 6.98-6.94 (m, 4H), 3.83 (s, 6H)

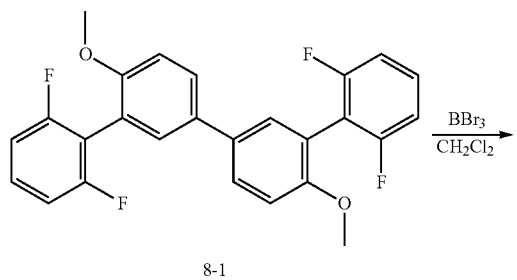

8-1 b) Compound 8-1 (18.8 g, 42.9 mmol) was dissolved in CH$_2$Cl$_2$ (600 mL), and the solution was cooled at −78° C. To the solution was 1 M boron tribromide in CH$_2$Cl$_2$ (129 mL, 129 mmol) added dropwise under N$_2$ atmosphere, and then the mixture was stirred 4 h. The reaction mixture was cooled at −60° C., and 60 mL of MeOH was added there. After the reaction mixture was warmed at room temperature, 240 mL of water was added there. The aqueous layer was extracted with CH$_2$Cl$_2$. The combined organic layer was washed with water. After drying over MgSO$_4$, the solvent was removed under reduced pressure to give compound 8-2 as yellowish liquid (17.3 g, 98%).

$^1$H-NMR (300 MHz, CDCl$_3$): δ 7.53 (dd, J=2.3, 8.6 Hz, 2H), 7.44 (d, J=2.3 Hz, 2H), 7.38-7.33 (m, 6H), 7.07-7.01 (m, 6H), 4.90 (s, 2H)

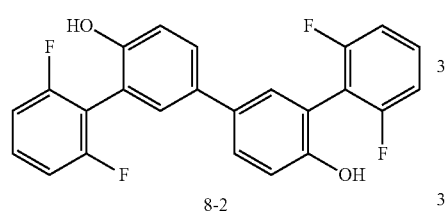

8-2

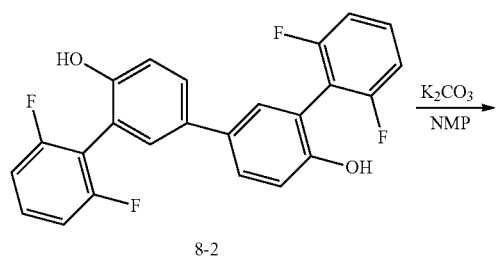

8-2

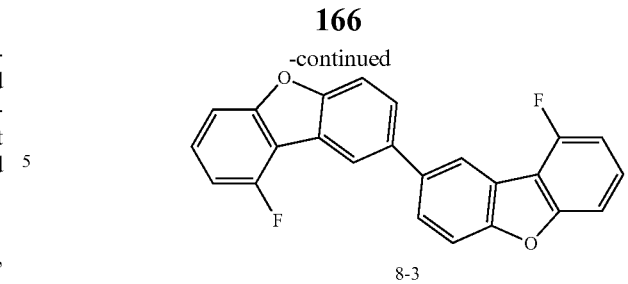

8-3 c) Compound 8-2 (17.3 g, 42.16 mmol) was dissolved in N-methylpyrrolidone (410 mL). To the solution was potassium carbonate (23.3 g, 168 mmol) added. Then, the mixture was stirred at 190° C. for 2 h. After the reaction mixture was cooled at room temperature, 600 mL of water was added to the reaction mixture. The solid was collected by filtration, washed with MeOH and hexane, and dried over into a vacuum oven to give 15.7 g (99%) of compound 8-3 as a white solid.

$^1$H-NMR (300 MHz, CDCl$_3$): δ 8.32 (d, J=1.9 Hz, 2H), 7.80 (dd, J=2.1, 8.1 Hz, 2H), 7.67 (d, J=8.6 Hz, 2H), 7.46-7.39 (m, 4H), 7.10-7.06 (m, 2H)

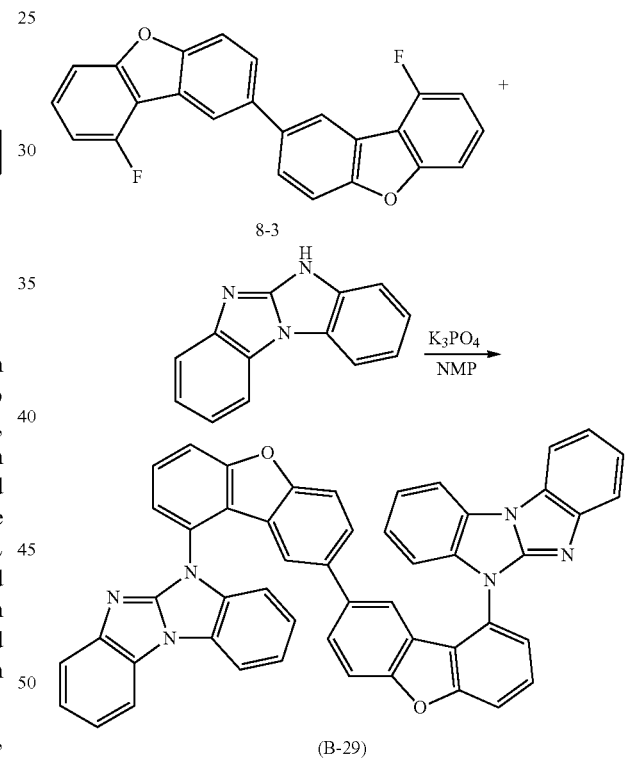

(B-29)

d) Compound 8-3 (3.0 g, 8.10 mmol), benzimidazolo[1,2-a]benzimidazole (1.85 g, 8.91 mmol), and potassium phosphate (1.96 g, 16.2 mmol) were added to NMP (30 mL). The mixture was stirred at 190° C. for 17 h. In addition, potassium phosphate (3.92 g, 32.4 mmol) was added there, and the mixture was stirred at the same temperature for 27 h. After reaction mixture was cooled at room temperature, it was diluted with water to give a solid. The solid was collected by filtration, and it was washed with 300 mL of MeOH. The crude product was purified by column chromatography on silica gel eluting with CH$_2$Cl$_2$ to yield 4.7 g (78%) of compound (B-29) as a white solid. LC-MS (m/z) 745.

Comparative Application Example 1

A glass substrate with 120 nm-thick indium-tin-oxide (ITO) transparent electrode used as an anode is first cleaned with isopropanol in an ultrasonic bath for 10 min. To eliminate any possible organic residues, the substrate is exposed to an ultraviolet light and ozone for further 30 min. This treatment also improves the hole injection properties of the ITO. The cleaned substrate is mounted on a substrate holder and loaded into a vacuum chamber. Thereafter, the organic materials specified below are applied by vapor deposition to the ITO substrate at a rate of approx. 0.2-1 Å/sec at about $10^{-6}$-$10^{-8}$ mbar. As a hole injection layer, compound

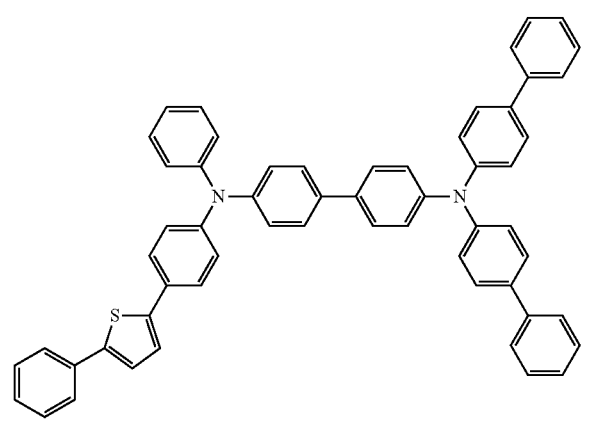 [SMILES: c1ccc(-c2ccc(N(c3ccc(-c4ccccc4)cc3)c3ccc(-c4ccc(N(c5ccccc5)c5ccc(-c6ccc(-c7ccccc7)s6)cc5)cc4)cc3)cc2)cc1]

with 30 nm thickness is applied. Then compound

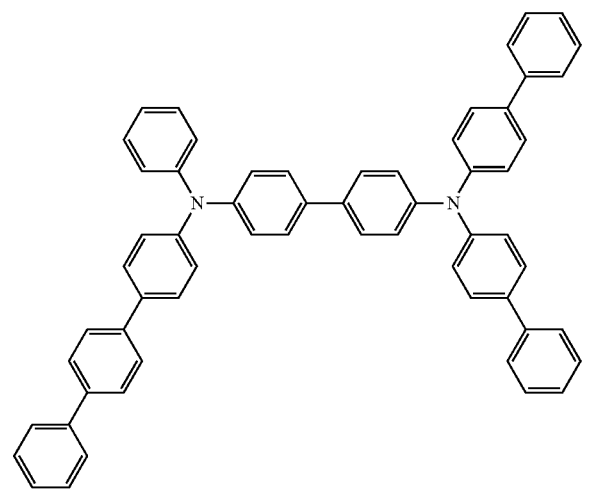 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]

with 60 nm thickness is applied as a hole transporting layer.

As an exciton and electron blocker, compound

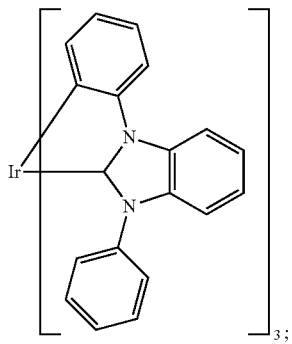

(HTM-1)

for preparation, see Ir complex (7) in the application WO2005/019373) is then applied with a thickness of 10 nm.

Subsequently, a mixture of 20% by weight of emitter compound,

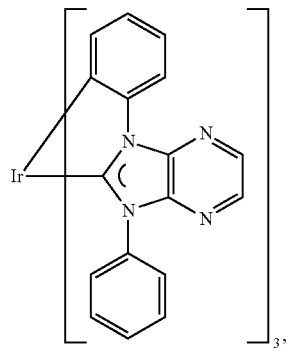

(BE-1)

15% by weight of compound (HTM-1) and 65% by weight of host

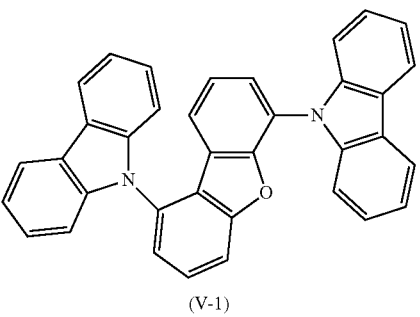

(V-1)

are applied by vapor deposition in a thickness of 40 nm. Subsequently, material (V-1) is applied by vapour deposition with a thickness of 5 nm as an exciton and hole blocker.

Thereafter, compound

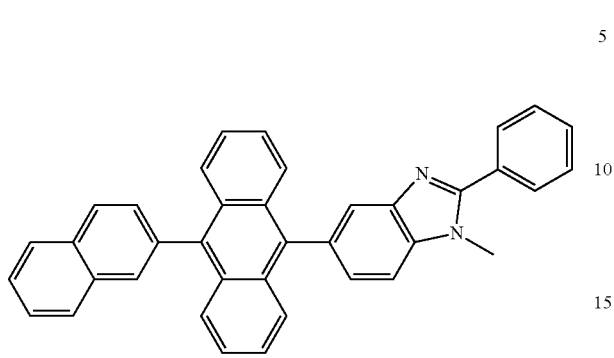

with 20 nm thickness is deposited as an electron transport layer. Finally, 1 nm-thick LiF is deposited as an electron injection layer and 80 nm-thick Al is then deposited as a cathode to complete the device. The device is sealed with a glass lid and a getter in an inert nitrogen atmosphere with less than 1 ppm of water and oxygen OLED Characterization To characterize the OLED, electroluminescence spectra are recorded at various currents and voltages. In addition, the current-voltage characteristic is measured in combination with the luminance to determine luminous efficiency and external quantum efficiency (EQE). Driving voltage U and EQE are given at luminance (L)=1000 cd/m². Furthermore, 50% lifetime (LT50), the time spent until the initial luminance of 40'000 cd/m² is reduced to 50% (2'000 cd/m²), is recorded. EQE and LT50 of the Comparative Application Examples are set to 100 and EQE and LT50 of the Application Examples are specified in relation to those of the Comparative Application Examples.

Application Examples 1 and 2

Comparative Application Example 1 is repeated except that the host (V-1) and the exciton and hole blocker (V-1) are replaced by compound

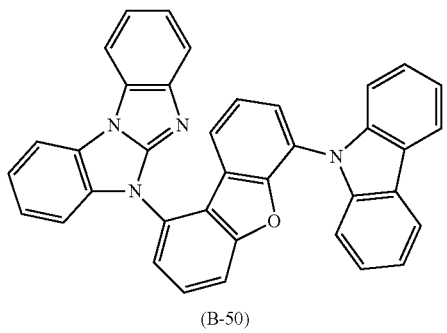

(B-50)

and

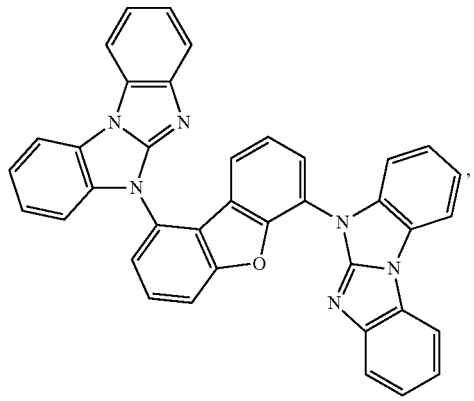

(B-49)

respectively. The device results are shown in Table 1.

TABLE 1

| Appl. Ex. | Host | HBL | U [V] | EQE [%] | LT50 [%] @4k nit |
|---|---|---|---|---|---|
| 1 | (B-50) | (B-50) | 5.16 | 95 | 172 |
| 2 | (B-49) | (B-49) | 5.25 | 96 | 200 |
| Comp. Appl. Ex. 1 | (V-1) | (SH-1) | 4.89 | 100 | 100 |

As shown in Table 1, it is found that the LT50 is improved by replacing the reference compound (V-1) with the compound (B-49) and (B-50), respectively as a host.

Comparative Application Example 2

Comparative Application Example 1 is repeated except that the exciton and hole blocker (V-1) is replaced by compound

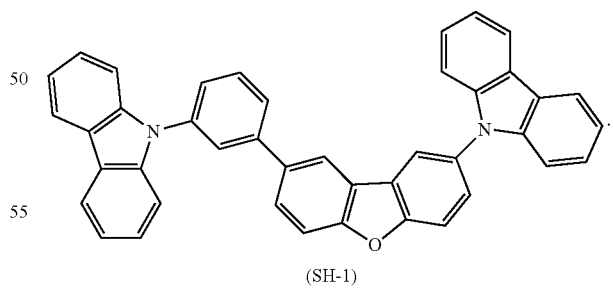

(SH-1)

Application Examples 3 and 4

Comparative Application Example 2 is repeated except that the host (V-1) is replaced by compound (B-50) and (B-49), respectively. The device results are shown in Table 2.

TABLE 2
| Appl. Ex. | Host | HBL | U [V] | EQE [%] | LT50 [%] @4k nit |
|---|---|---|---|---|---|
| 3 | (B-50) | (SH-1) | 5.36 | 95 | 168 |
| 4 | (B-49) | (SH-1) | 5.67 | 96 | 208 |
| Comp. Appl. Ex. 2 | (V-1) | (SH-1) | 4.98 | 100 | 100 |
As shown in Table 2, it is found that the LT50 is improved by replacing the reference compound (V-1) with the compound (B-50) and (B-49), respectively as host.
The invention claimed is:
1. A compound of formula (Ia-1) or (Ia-2)
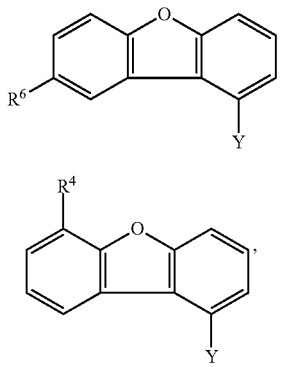
(Ia-1)
(Ia-2)
wherein
$R^4$ and $R^6$ are H, a group of formula
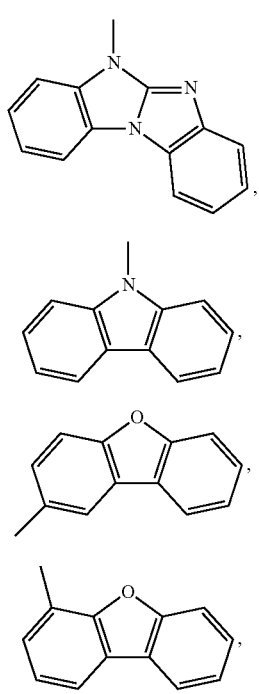
(XIa)
(XIb)
(XIc)
(XId)
(XIe)
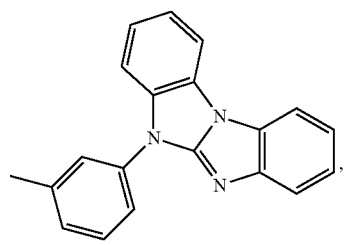
(XIf)
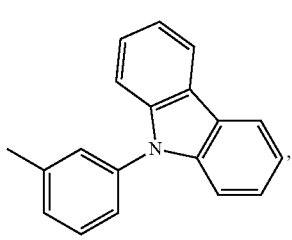
(XIg)
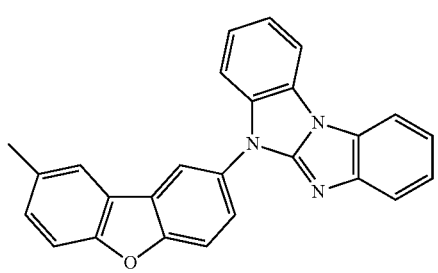
(XIj)
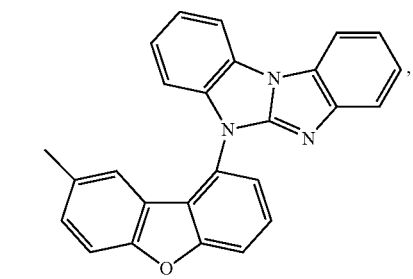
(XIk)
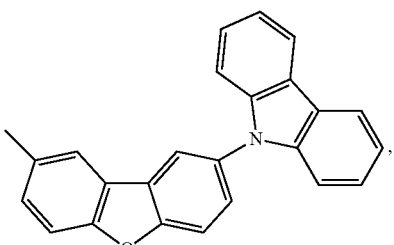
(XIn)
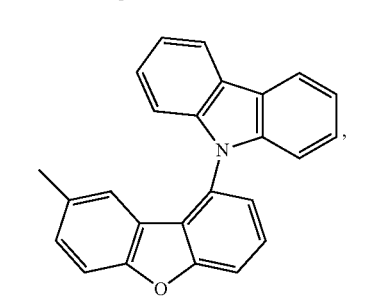

-continued
(XIo)
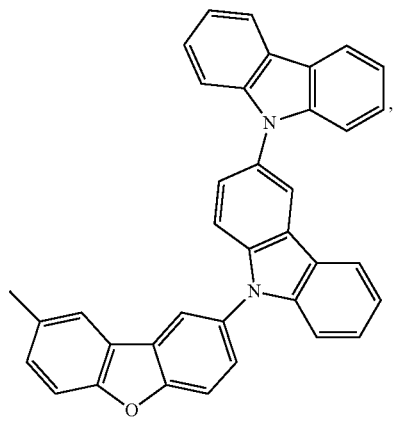
(XIs)
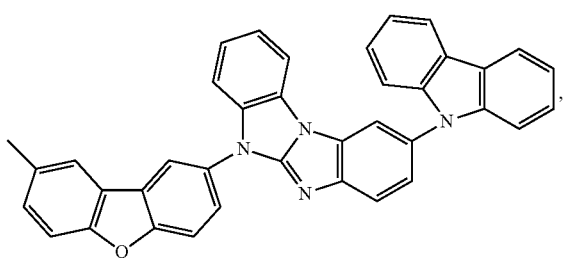
(XIw)
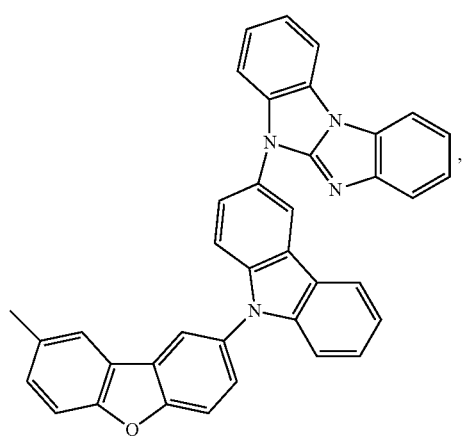
(XIIa)
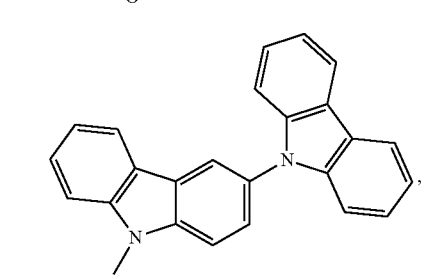
(XIIb)
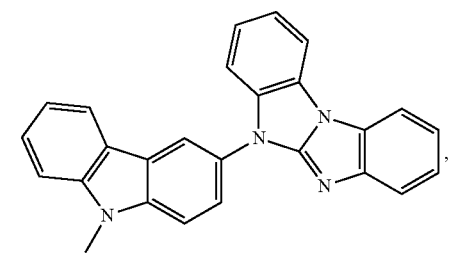
(XIIc)
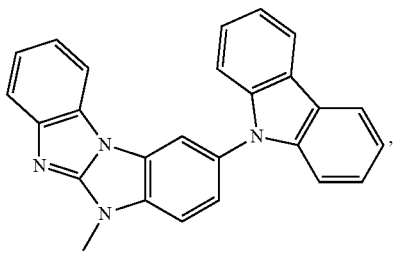
(XIIe)
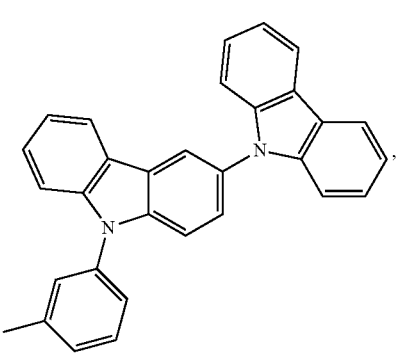
(XIIf)
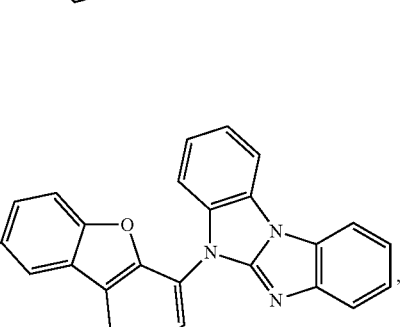, or
(XIIg)
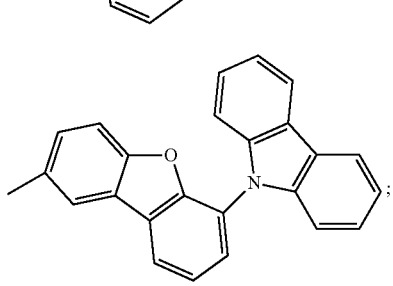;
Y is a group of formula
(Xa-1)
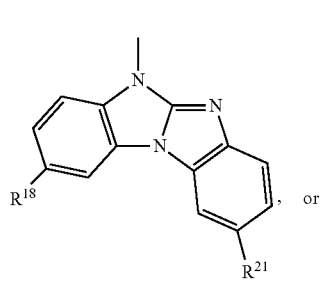, or -continued

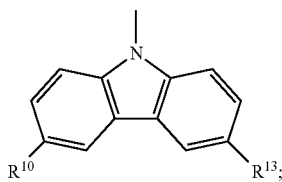
(Xb-1)

wherein

R¹⁰ is H, or a group of formula

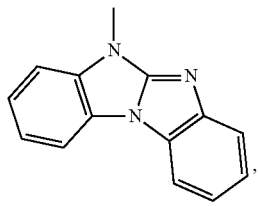 [SMILES: Cn1c2ccccc2n2c3ccccc3nc12]

R¹⁸ is H, or a group of formula

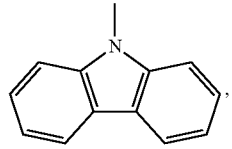

and

R¹³ and R²¹ are H, with the proviso that in case Y is a group of formula (Xb-1), R⁴ and R⁶ are a group of formula (XIa), (XIe), (XIg), (XIj), (XIs), (XIw), (XIIb), (XIIc), or (XIIf).

2. An electronic device, comprising the compound according to claim 1.

3. The electronic device according to claim 2, which is an electroluminescent device.

4. A charge transport layer, a charge/exciton blocker layer, or an emitting layer comprising the compound according to claim 1.

5. The emitting layer according to claim 4, comprising the compound as host material in combination with a phosphorescent emitter.

6. An apparatus selected from the group consisting of stationary visual display units; mobile visual display units; illumination units; keyboards; items of clothing; furniture; wallpaper, comprising the organic electronic device according to claim 2.

7. An electrophotographic photoreceptor, a photoelectric converter, an organic solar cell, a switching element, an organic light emitting field effect transistor, an image sensor, a dye laser, or an electroluminescent device comprising the compound according to claim 1.

8. A process for preparing a compound of formula (I),

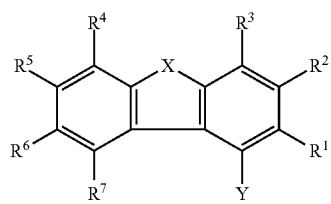
(I)

comprising:

a) reacting a compound of formula (XIV)

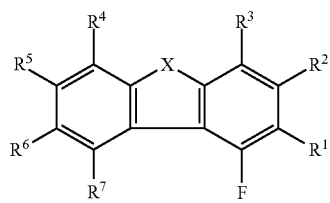
(XIV)

with a compound of formula (XVI) or (XVII)

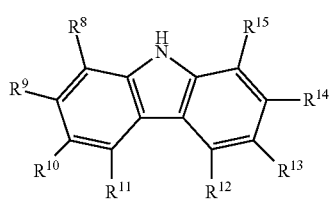
(XVI)

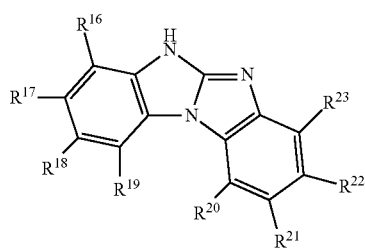
(XVII)

in the presence of a base in a solvent at room temperature to reflux temperature of the solvent, wherein X is O or S;

Y is a group of formula —[Ar¹]$_a$—[Ar²]$_b$—[Ar³]$_c$-A¹;

A¹ is a group of formula

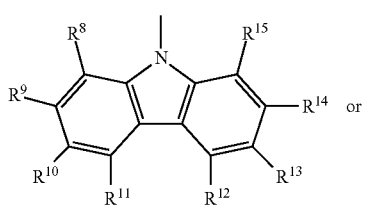
(Xa)

or

-continued

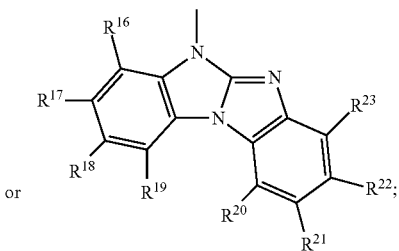

(Xb)

wherein
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are independently of each other H, F, CN, $NO_2$, $Si(R^{24})(R^{25})(R^{26})$, $P(O)(R^{27})(R^{28})$, $N(R^{30})(R^{31})$, a $C_1$-$C_{25}$alkyl group, which can optionally be substituted by E, and or interrupted by D, a $C_3$-$C_{18}$cycloalkyl group, which can optionally be substituted by G, or a group of formula —$[Ar^4]_d$—$[Ar^5]_e$—$[Ar^6]_f$-$A^2$, a is 0, or 1, b is 0, or 1, c is 0, or 1, d is 0, or 1, e is 0, or 1, f is 0, or 1, $Ar^1$, $Ar^2$, $Ar^3$, $Ar^4$, $Ar^5$ and $Ar^6$ are independently of each other a $C_6$-$C_{24}$arylene group, which can optionally be substituted by G, a $C_2$-$C_{30}$heteroarylene group, which can optionally be substituted by G, $A^2$ is H, F, CN, $NO_2$, $Si(R^{24})(R^{25})(R^{26})$, $P(O)(R^{27})(R^{28})$, $N(R^{30})(R^{31})$, a $C_1$-$C_{25}$alkyl group, which can optionally be substituted by E, and or interrupted by D, a $C_3$-$C_{18}$cycloalkyl group, which can optionally be substituted by G, a $C_6$-$C_{24}$aryl group, which can optionally be substituted by G, a $C_2$-$C_{30}$heteroaryl group, which can optionally be substituted by G;

$R^{24}$, $R^{25}$, $R^{26}$, $R^{27}$, and $R^{28}$ are independently of each other a $C_1$-$C_{25}$alkyl group, a $C_6$-$C_{24}$aryl group, which can optionally be substituted by G, or a $C_2$-$C_{30}$heteroaryl group, which can optionally be substituted by G;

$R^{30}$ and $R^{31}$ are independently of each other a $C_6$-$C_{24}$aryl group, which can optionally be substituted by G, or a $C_2$-$C_{30}$heteroaryl group, which can optionally be substituted by G;

D is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—,

E is —$OR^{69}$, —$SR^{69}$, —$NR^{65}R^{66}$, —$COR^{68}$, —$COOR^{67}$, —$CONR^{65}R^{66}$, —CN, F, or $NO_2$;

G is E, or a $C_1$-$C_{18}$alkyl group, a $C_3$-$C_{18}$cycloalkyl group, a $C_6$-$C_{24}$aryl group, a $C_6$-$C_{24}$aryl group, which is substituted by F, —CN, $C_1$-$C_{18}$alkyl, or $C_1$-$C_{18}$alkyl which is interrupted by O; a $C_2$-$C_{50}$heteroaryl group, or a $C_2$-$C_{50}$heteroaryl group, which is substituted by F, —CN, $C_1$-$C_{18}$alkyl, $C_1$-$C_{18}$alkyl which is interrupted by O;

$R^{63}$ and $R^{64}$ are independently of each other H, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring;

$R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{68}$ is H; a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—;

$R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl;

with the proviso that in case $A^1$ is a group of formula (Xa), at least one of $R^1$, $R^2$, $R^3$, $R^4$, $R^5$, $R^6$ and $R^7$ is a group of formula —$[Ar^4]_d$—$[Ar^5]_e$—$[Ar^6]_f$-$A^2$, wherein $A^2$ is a group of formula (Xb).

* * * * *